US012333412B1

(12) United States Patent
Mazed

(10) Patent No.: US 12,333,412 B1
(45) Date of Patent: *Jun. 17, 2025

(54) INTELLIGENT (SELF-LEARNING) SUBSYSTEM IN ACCESS NETWORKS

(71) Applicant: Mohammad A. Mazed, Yorba Linda, CA (US)

(72) Inventor: Mohammad A. Mazed, Yorba Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/831,206

(22) Filed: Sep. 14, 2024

Related U.S. Application Data

(63) Continuation-in-part of application No. 18/445,647, filed on Dec. 9, 2023, now Pat. No. 12,101,609, (Continued)

(51) Int. Cl.
| | |
|---|---|
| *G06N 3/0455* | (2023.01) |
| *G06N 3/006* | (2023.01) |
| *G06N 3/065* | (2023.01) |
| *G06N 3/086* | (2023.01) |
| *G06V 10/764* | (2022.01) |
| *G06V 10/82* | (2022.01) |
| *G10L 15/16* | (2006.01) |
| *G10L 15/18* | (2013.01) |
| *G10L 15/22* | (2006.01) |
| *G10L 15/30* | (2013.01) |
| *G16H 40/67* | (2018.01) |
| *G16H 80/00* | (2018.01) |
| *H01L 25/16* | (2023.01) |
| *H04R 1/02* | (2006.01) |
| *H04R 17/00* | (2006.01) |

(52) U.S. Cl.
CPC ........... *G06N 3/0455* (2023.01); *G06N 3/006* (2013.01); *G06N 3/065* (2023.01); *G06N 3/086* (2013.01); *G06V 10/764* (2022.01); *G06V 10/82* (2022.01); *G10L 15/16* (2013.01); *G10L 15/18* (2013.01); *G10L 15/22* (2013.01); *G10L 15/30* (2013.01); *G16H 40/67* (2018.01); *G16H 80/00* (2018.01); *H01L 25/167* (2013.01); *H04R 1/028* (2013.01); *H04R 17/00* (2013.01); *H04R 2499/15* (2013.01)

(58) Field of Classification Search
CPC .... H01S 3/101; H01S 5/0265; H01S 5/06256; H01S 5/06258; H04B 10/272; H04B 10/5161; H04J 14/0223; H04J 14/0256; H04J 14/0282; H04Q 11/0005; H04Q 11/0067; H04Q 2011/0016; H04Q 2011/0032; H04Q 2011/0064
See application file for complete search history.

(56) References Cited

U.S. PATENT DOCUMENTS

| | | | |
|---|---|---|---|
| 10,634,851 B2* | 4/2020 | Steinbrecher | G02B 6/3542 |
| 2009/0180747 A1* | 7/2009 | Schrauwen | B82Y 20/00 |
| | | | 385/129 |

(Continued)

*Primary Examiner* — Omar S Ismail

(57) ABSTRACT

An intelligent (self-learning) sensor-aware and/or context-aware subsystem comprising (i) a System-on-a-Chip (SoC), (ii) a radio transceiver, (iii) a microphone, (iv) a voice processing module, (v) a (bio-inspired) neuromorphic event camera or a hyperspectral camera, (vi) a first set of computer implemental instructions in artificial neural networks (ANN) (which may include a transformer model/diffusion model or Poisson flow generative model++ (PFGM++)), (vii) a second set of computer implementable instructions to analyze and interpret contextual data and (viii) an autonomous artificial intelligence (AI) agent is disclosed.

62 Claims, 18 Drawing Sheets

Related U.S. Application Data which is a continuation-in-part of application No. 17/803,388, filed on Jun. 15, 2022, now Pat. No. 11,892,746, which is a continuation-in-part of application No. 17/300,477, filed on Jul. 14, 2021, now Pat. No. 11,885,887, said application No. 18/445,647 is a continuation-in-part of application No. 17/300,394, filed on Jun. 15, 2021, now Pat. No. 11,843,903, which is a continuation-in-part of application No. 16/974,218, filed on Nov. 16, 2020, now Pat. No. 11,178,474, said application No. 17/300,477 is a continuation-in-part of application No. 16/602,404, filed on Sep. 28, 2019, now Pat. No. 11,320,588.

(60) Provisional application No. 63/103,048, filed on Jul. 14, 2020.

(56) References Cited

U.S. PATENT DOCUMENTS

| | | | |
|---|---|---|---|
| 2010/0278479 A1* | 11/2010 | Bratkovski | G02B 6/12007 359/315 |
| 2010/0285082 A1* | 11/2010 | Fernandez | A61B 5/024 506/13 |
| 2011/0099142 A1* | 4/2011 | Karjalainen | H04M 1/72448 707/600 |
| 2012/0011092 A1* | 1/2012 | Tang | G11C 11/54 706/33 |
| 2012/0059780 A1* | 3/2012 | Kononen | H04M 1/72454 706/14 |
| 2014/0311350 A1* | 10/2014 | Campbell | B01D 46/46 96/417 |
| 2014/0380425 A1* | 12/2014 | Lockett | G06F 21/00 726/4 |
| 2015/0333480 A1* | 11/2015 | Santis | H01S 5/2231 372/45.01 |
| 2016/0034809 A1* | 2/2016 | Trenholm | G06F 18/214 706/20 |
| 2016/0161691 A1* | 6/2016 | Hayakawa | G02B 6/29382 250/227.27 |
| 2016/0261091 A1* | 9/2016 | Santis | H01S 5/1032 |
| 2017/0116514 A1* | 4/2017 | Abel | G06N 3/0675 |
| 2017/0316487 A1* | 11/2017 | Mazed | G06Q 30/0241 |
| 2018/0054257 A1* | 2/2018 | Witzens | H04B 10/07955 |
| 2018/0351652 A1* | 12/2018 | Ashrafi | H04W 28/02 |
| 2019/0370652 A1* | 12/2019 | Shen | G06N 3/08 |
| 2020/0110992 A1* | 4/2020 | Hosseinzadeh | G06N 3/04 |
| 2021/0173238 A1* | 6/2021 | Hosseinzadeh | H04B 10/5161 |

* cited by examiner

INTELLIGENT (SELF-LEARNING) SUBSYSTEM IN ACCESS NETWORKS

CROSS REFERENCE TO RELATED APPLICATIONS

The present application is
a continuation-in-part (CIP) of patent application of (a) U.S. Non-Provisional patent application Ser. No. 18/445,647 entitled "INTELLIGENT (SELF-LEARNING) SUBSYSTEM IN ACCESS NETWORKS", filed on Dec. 9, 2023, wherein (a) is a continuation-in-part (CIP) patent application of (b) U.S. Non-Provisional patent application Ser. No. 17/803,388 entitled "SUPER SYSTEM ON CHIP", filed on Jun. 15, 2022 (which resulted in a U.S. Pat. No. 11,892,746, issued on Feb. 6, 2024), wherein (b) is a continuation-in-part (CIP) patent application of (c) U.S. Non-Provisional patent application Ser. No. 17/300,477 entitled "IMAGING SUBSYSTEM", filed on Jul. 14, 2021, (which resulted in a U.S. Pat. No. 11,885,887, issued on Jan. 30, 2024), wherein (c) claims priority to (d) U.S. Provisional Patent Application No. 63/103,048 entitled "SYSTEM AND METHOD OF AMBIENT/PERVASIVE USER/HEALTHCARE EXPERIENCE", filed on Jul. 14, 2020, wherein (c) is a continuation-in-part (CIP) patent application of (e) U.S. Non-Provisional patent application Ser. No. 16/602,404 entitled "SUPER SYSTEM ON CHIP", filed on Sep. 28, 2019, (which resulted in a U.S. Pat. No. 11,320,588, issued on May 3, 2022), wherein (a) is a continuation-in-part (CIP) patent application of (f) U.S. Non-Provisional patent application Ser. No. 17/300,394 entitled "INTELLIGENT SUBSYSTEM IN ACCESS NETWORKS", filed on Jun. 15, 2021, (which resulted in a U.S. Pat. No. 11,843,903, issued on Dec. 12, 2023), wherein (f) is a continuation-in-part (CIP) patent application of (g) U.S. Non-Provisional patent application Ser. No. 16/974,218 entitled "INTELLIGENT SUBSYSTEM IN ACCESS NETWORKS", filed on Nov. 16, 2020 (which resulted in a U.S. Pat. No. 11,178,474, issued on Nov. 16, 2021).

The entire contents of all (i) U.S. Non-Provisional Patent Applications, (ii) U.S. Provisional Patent Applications, as listed in the previous paragraph and (iii) the filed (Patent) Application Data Sheet (ADS) are hereby incorporated by reference, as if they are reproduced herein in their entirety.

FIELD OF THE INVENTION

Bandwidth demand and total deployment cost (capital cost and operational cost) of an advanced optical access communication system are increasing, while a return on investment (ROI) is decreasing. This has created a significant business dilemma.

More than ever before, we have become more mobile and global. Intelligent pervasive and always-on internet access via convergence of all (e.g., an electrical/optical/radio/electromagnetic/sensor/biosensor) communication networks can provide connectivity at anytime, from anywhere, to anything is desired.

The present invention is related to a dynamic bidirectional optical access communication system with an intelligent subscriber subsystem that can connect/couple/interact (via one/more/all the networks as listed hereinafter: electrical/optical/radio/electromagnetic/sensor/biosensor communication network(s)) with an object and an intelligent appliance, utilizing internet protocol version 6 (IPv6) and its subsequent versions.

An intelligent subscriber subsystem and/or an object and/or an intelligent appliance includes one/more of the following: (a) modules (wherein a module is an integration of critical electrical/optical/radio/sensor components, circuits and algorithms needed to achieve a desired property of a module): a laser, a photodiode, a modulator, a demodulator, a phase-to-intensity converter, an amplifier, a wavelength combiner/decombiner, an optical power combiner/decombiner, a cyclic arrayed waveguide router, a micro-electrical-mechanical-system (MEMS) space switch, an optical switch, an optical circulator, an optical filter, an optical intensity attenuator, a processor, a memory, a display component, a microphone, a camera, a sensor, a biosensor, a radio, a near-field-communication (NFC), a scanner, a power source, (b) an embedded and/or a cloud based operating system software module (wherein a software module is an integration of critical algorithms/computer implementable instructions needed to achieve a desired property of a software module) and/or (c) an embedded and/or a cloud based intelligence rendering software module.

Furthermore, an intelligent subscriber subsystem and/or an intelligent appliance can include a (personal) artificial intelligence (AI) based self-learning assistant that may be coupled with a Super System on Chip (SSoC), which can be either non-optically enabled (that may include memristors/super memristors) or optically enabled (that may include Mach-Zehnder interferometers, wherein an input or an output of the (optically enabled) Super System on Chip can be coupled with the Mach-Zehnder interferometers). An intelligent subscriber subsystem and/or an intelligent appliance can be a user cloud based subsystem or a cloud based subsystem. It should be noted that a super memristor can include (i) a resistor, (ii) a capacitor and (iii) a memristor (e.g., a phase transition/phase change material based memristor). Furthermore, a Super System on Chip or a (optically enabled) Super System on Chip or a System-on-a-Chip (SoC) can be integrated on a wafer scale for higher performance and higher computing functionality. It should be noted that HfOx and/or TaOx material (e.g., Ag/TiN/HfOx/HfOy/HfOx/TiN/Ag memristor with sub-nanoseconds switching speed and $10^{10}$ on/off ratio) based memristors may be compatible with complementary metal-oxide-semiconductor (CMOS) integrated circuit manufacturing process.

Furthermore, an object can sense/measure/collect/aggregate/compare/map and connect/couple/interact (via one/more/all the networks as listed hereinafter: electrical/optical/radio/electromagnetic/sensor/biosensor communication network(s)) with another object, an intelligent subscriber subsystem and an intelligent appliance, utilizing internet protocol version 6 (IPv6) and its subsequent versions. Generally, a (connected) network of intelligent subscriber subsystems and/or intelligent appliances and/or objects may be considered as a system.

SUMMARY OF THE INVENTION

A dynamic intelligent bidirectional optical access communication system utilizes two critical optical modules: a phase modulator and an intensity modulator at an intelligent subscriber subsystem. Together, these two critical optical modules can reduce the Rayleigh backscattering effect on the propagation of optical signals.

The reduced Rayleigh backscattering effect can enable a longer-reach optical access communication network (longer-reach than a currently deployed optical access communication network) between an intelligent subscriber subsystem and a super node (e.g., many neighboring nodes collapsed into a preferred super node). Such a longer-reach optical access communication network can eliminate significant costs related to a vast array of middle equipment (e.g., a router/switch), which otherwise would be needed between a standard node (without a super node configuration) and many remote nodes, according to a currently deployed optical access communication network.

In one embodiment of the present invention, a bidirectional optical access communication system can be configured to be capable of a longer-reach optical access communication network.

In another embodiment of the present invention, a bidirectional optical access communication system can be configured to be capable of dynamically providing wavelength on-demand and/or bandwidth on-demand and/or service on-demand.

In another embodiment of the present invention, fabrication and construction of a wavelength tunable laser component/module are described.

In another embodiment of the present invention, an optical signal can be routed to an intended destination securely by extracting an intended destination from a destination marker optical signal.

In another embodiment of the present invention, fabrication/construction and applications of an object are described.

In another embodiment of the present invention, an object can sense/measure/collect/aggregate/compare/map and connect/couple/interact (via one/more/all the networks as listed hereinafter: electrical/optical/radio/electromagnetic/sensor/biosensor communication network(s)) with another object, an intelligent subscriber subsystem and an intelligent appliance, utilizing internet protocol version 6 (IPv6) and its subsequent versions.

In another embodiment of the present invention, an intelligence rendering software module allows a subscriber subsystem to adapt/learn/relearn a user's interests/preferences/patterns, thereby rendering intelligence to a subscriber subsystem.

In another embodiment of the present invention, an intelligence rendering software module allows an appliance to adapt/learn/relearn a user's interests/preferences/patterns, thereby rendering intelligence to an appliance.

In another embodiment of the present invention, fabrication and construction of a near-field communication enabled micro-subsystem/intelligent appliance is described.

In another embodiment of the present invention, a portfolio of applications (e.g., an intelligent, location based and personalized social network and direct/peer-to-peer marketing) also described.

In another embodiment of the present invention, a Super System on Chip including memristors/super memristors is described.

In another embodiment of the present invention, a (optically enabled) Super System on Chip including a Mach-Zehnder interferometer (MZI) is described.

In another embodiment of the present invention, a (personal) artificial intelligence based self-learning assistant (which may be a user cloud based subsystem or a cloud based subsystem) interfaced with an intelligent subsystem, that can be coupled with a wireless network and/or an optical access communication network is also described.

The present invention can be better understood in the description below with accompanying drawings.

DETAILED DESCRIPTION OF THE PREFERRED EMBODIMENTS

Figure 1:
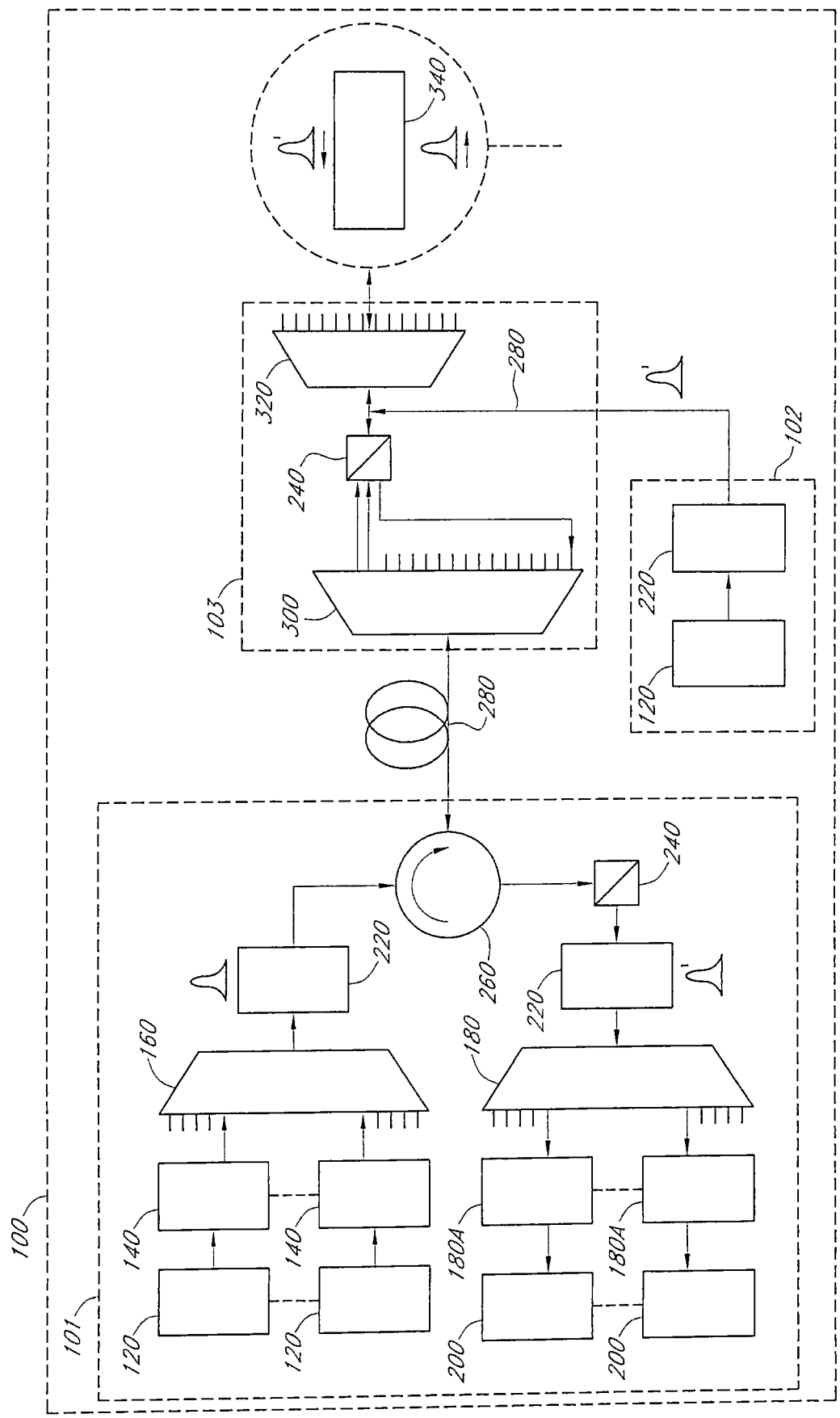
FIG. 1 illustrates a block diagram configuration of a bidirectional optical access communication network 100, according to one embodiment of the present invention.

FIG. 1 illustrates a block diagram configuration of a bidirectional optical access communication network 100, which includes a super node 101, many distant local nodes 102 and many distant remote nodes 103. The distance between the super node 101 and the remote node 103 is greater than the distance between the super node 101 and the local node 102. However, many local nodes 102 can collapse/reside within the super node 101 to enable a bidirectional optical access communication network 100, without a roadside electrical power requirement at the local node 102.

A bidirectional optical access communication network 100 is connected/coupled/interacted with the super node 101, many local nodes 102, many remote nodes 103 and many intelligent subscriber subsystems 340s (located at homes/businesses) over a dispersion-compensated single-mode optical fiber 280. At the super node 101, several laser modules (high power fast wavelength switching-wavelength tunable semiconductor laser modules are preferred) 120s provide a first set of downstream wavelengths, where each downstream wavelength is modulated at 10 Gb/s or higher Gb/s, by a corresponding intensity modulator module (an electro-absorption/Mach-Zehnder intensity modulator module is preferred) 140 to provide optical signals. These modulated downstream wavelengths (embedded with the optical signals) are combined by a wavelength combiner module 160 and amplified by an erbium-doped fiber amplifier (EDFA) module 220. These amplified downstream wavelengths are passed through a 3-port circulator module 260 and transmitted over the dispersion-compensated single-mode optical fiber (with a distributed Raman amplifier is preferred) 280 to the remote node 103. A distributed Raman amplifier can provide distributed amplification of the optical signal over the dispersion-compensated single-mode optical fiber 280 by nonlinear coupling/interaction between the optical signal and an optical pump signal, thereby effectively increasing the reach of an optical access communication network more than a currently deployed optical access communication network. At the remote node 103, the modulated downstream wavelengths from the super node 101, are decombined by an integrated wavelength combiner/decombiner module 300, filtered by a bandpass optical filter module (a wavelength switching-wavelength tunable bandpass optical filter module is preferred) 240, are power split by an integrated optical power combiner/decombiner module 320 and are transmitted to several intelligent subscriber subsystems 340s. However, all the optical modules at the remote node 103 must be temperature insensitive to operate within a wide temperature range at the remote node 103, as there may not be an option of electrical power at the remote node 103. The downstream wavelengths from the super node 101 to the number of intelligent subscriber subsystems 340s can be transmitted and correspondingly received by photodiode modules 200s at the intelligent subscriber subsystems 340s, utilizing a time division multiplexed statistical bandwidth allocation and/or a broadcasting method.

The local node 102 includes the laser module 120, which is connected/coupled/interacted with the erbium-doped fiber amplifier (EDFA) module 220 to provide an upstream wavelength from the intelligent subscriber subsystems 340s, which is offset in wavelength with respect to the first set of downstream wavelengths generated at the super node 101. The upstream wavelength power splits through the integrated optical power combiner/decombiner module 320 at the remote node 103 and is transmitted to the number of intelligent subscriber subsystems 340s for further optical processing by an optical processing micro-subsystem 360. An optically processed upstream wavelength (embedded with the optical signals) by the optical processing micro-subsystem 360 (within the intelligent subscriber subsystem 340) is looped/returned back through the integrated optical power combiner/decombiner module 320, the bandpass optical filter module 240 and the integrated wavelength combiner/decombiner module 300 at the remote node 103. The optically processed upstream wavelength is transmitted over the dispersion-compensated single-mode optical fiber 280 and passed through the 3-port circulator module 260 at the super node 101. The 3-port circulator module 260 provides the upstream wavelengths from a number of intelligent subscriber subsystems 340s to the bandpass optical filter 240, the erbium-doped fiber amplifier (EDFA) module 220, the wavelength decombiner module 180, a number of external fiber-optic interferometer modules 180As (to convert a phase modulation signal into an intensity modulation signal) and the photodiode modules 200s at the super node 101, wherein each photodiode module 200 is detecting the distinct upstream wavelength. Furthermore, each photodiode module 200 includes one or more of the following optical/electronic components: a 10 Gb/s or higher Gb/s linear photodiode chip, a 10 Gb/s or higher Gb/s mesa-type/waveguide-type avalanche photodiode chip (APD), a 10 Gb/s or higher Gb/s burst-mode transimpedance amplifier, a 10 Gb/s or higher Gb/s clock and data recovery (CDR), the bandpass optical filter 240 and a semiconductor optical amplifier 380 (if the semiconductor optical amplifier 380 is needed for optical gain in conjunction with a 10 Gb/s or higher Gb/s linear photodiode chip). The upstream wavelength from several intelligent subscriber subsystems 340s to the super node 101 can be transmitted and correspondingly received by the photodiode modules 200s at the super node 101, utilizing a time division multiplexed statistical bandwidth allocation and/or a broadcasting method.

Figure 2:
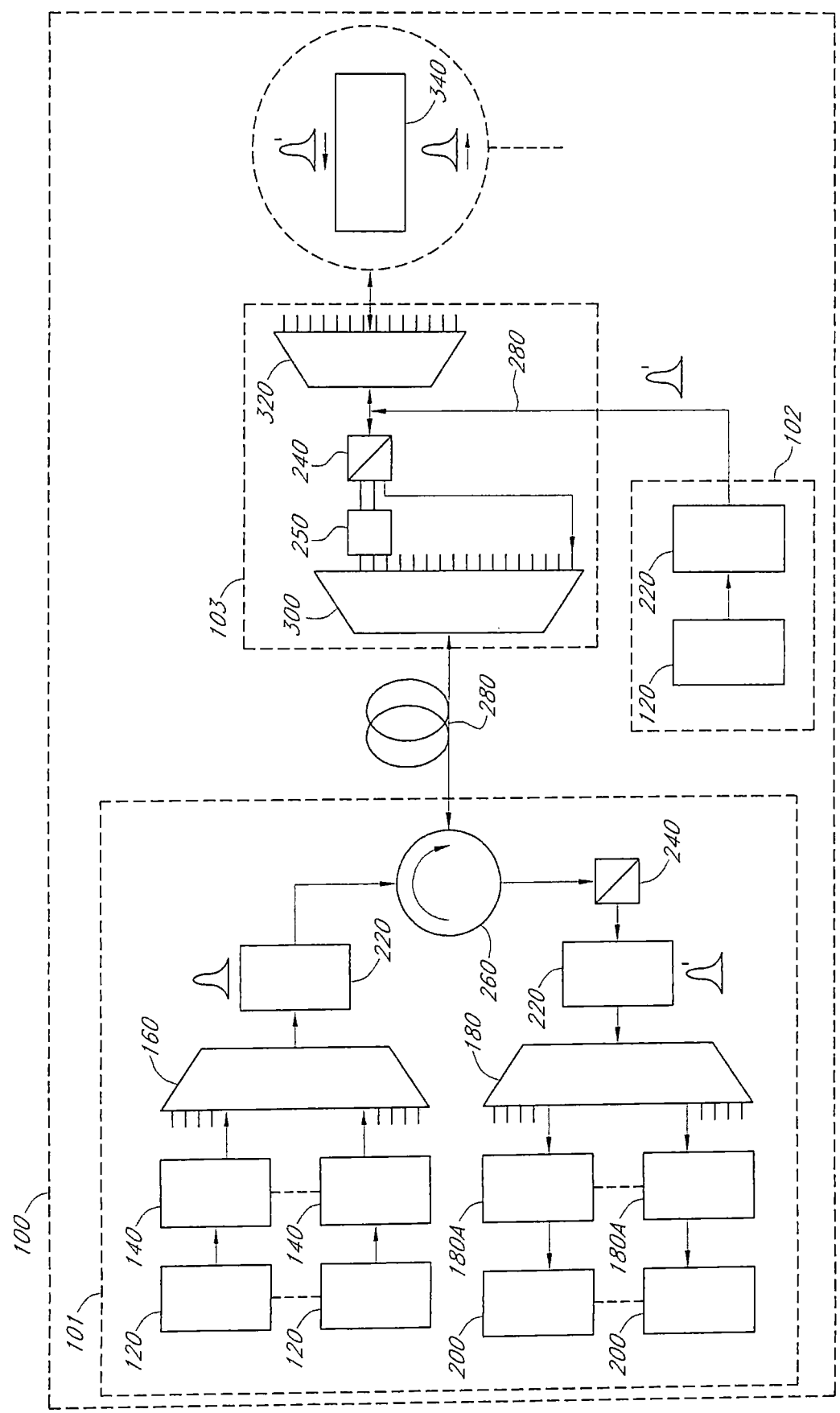
FIG. 2 illustrates a block diagram configuration of a dynamic bidirectional optical access communication network 100, according to another embodiment of the present invention.

FIG. 2 illustrates a block diagram configuration of a dynamic bidirectional optical access communication network 100, where any wavelength to the intelligent subscriber subsystem 340 can be dynamically varied on-demand by utilizing an M:M cyclic wavelength arrayed waveguide grating router module (a fast wavelength switching-wavelength tunable programmable M:M cyclic wavelength arrayed waveguide grating router module is preferred) 250 at the remote node 103. All possible switched output downstream wavelengths are arranged at the M outputs of the M:M cyclic wavelength arrayed waveguide grating router module 250 because of the free spectral range periodic property of the M:M cyclic wavelength arrayed waveguide grating router module. This configuration offers the flexibility of dynamically routing/delivering one or more downstream wavelengths with different modulation rates (e.g., 10 Gb/s or higher Gb/s) provided by the corresponding intensity modulator module 140, to the intelligent subscriber subsystem 340 for wavelength on-Demand, bandwidth on-Demand and service on-Demand, significantly increasing a return on investment. Thus, each dynamically routed wavelength with a specific modulation rate can provide a distinct bandwidth-specific service on-Demand (e.g., an ultra-high definition movie on-Demand) to the specific intelligent subscriber subsystem 340.

A method of providing bandwidth-specific service on-Demand can be realized by including at least steps: (a) the user requesting a specific service (e.g., an ultra-high definition movie on-Demand) at the specific intelligent subscriber subsystem 340, (b) delivering the specific service over a wavelength by the laser module 120 from the super node 101, (c) modulating the wavelength at a required modulation rate (e.g., 10 Gb/s or higher Gb/s) by the intensity modulator module 140 at the super node 101 and (d) then dynamically routing the said wavelength (embedded with the user requested specific service) by the M: M cyclic wavelength arrayed waveguide grating router module 250 at the remote node 103 and to the specific intelligent subscriber subsystem 340.

Furthermore, rapid wavelength routing (in space, wavelength and time) by the M:M cyclic wavelength arrayed waveguide grating router module 250 can be fabricated/constructed as an optical packet/interconnect router between many printed circuit boards/integrated circuits/processors.

Additionally, outputs of the M:M cyclic wavelength arrayed waveguide grating router module 250 at the remote node 103 can be connected/coupled/interacted with inputs of a large-scale N:N (e.g., a 1000:1000) micro-electrical-mechanical-system space switch module at the remote node 103 to provide much greater flexibility of wavelength routing.

An input-output echelle grating module and/or a negative-index photonic crystal super-prism module can be utilized as alternatives to the wavelength combiner module 160, the wavelength decombiner module 180 and the integrated wavelength combiner/decombiner module 300. A multi-mode interference (MMI) module and/or a Y-combiner module can be utilized as alternatives to the integrated optical power combiner/decombiner module 320 and the optical power combiner module 320A.

Figure 3:
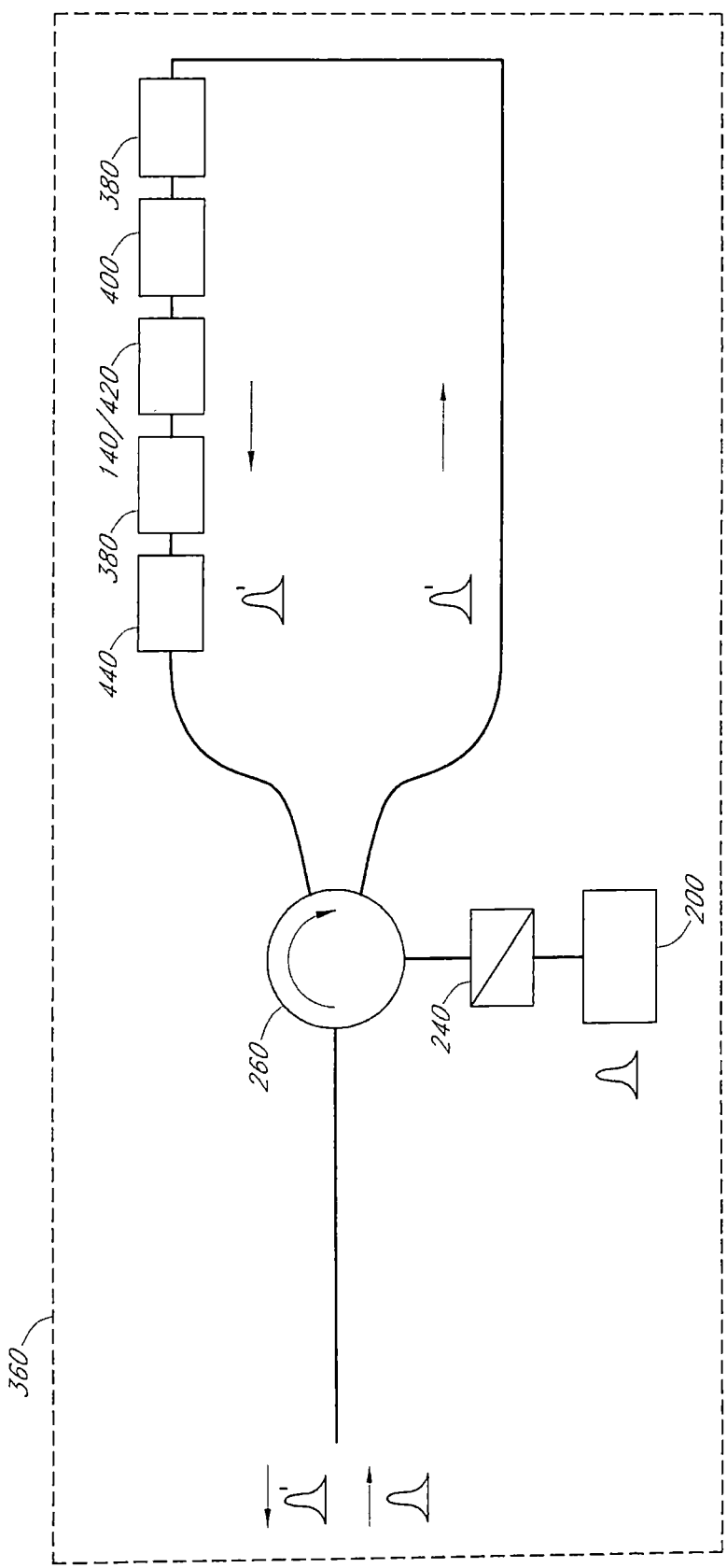
FIG. 3 illustrates a block diagram fabrication and construction of an optical processing micro-subsystem 360 (within an intelligent subscriber subsystem), according to another embodiment of the present invention.

FIG. 3 illustrates a block diagram construction of the optical processing micro-subsystem 360, wherein a downstream wavelength is passed through the 3-port circulator 260, the bandpass optical filter module 240 and the photodiode module 200. A wavelength from the laser module 120 at the local node 102 is passed through the 3-port circulator module 260 within the optical processing micro-subsystem 360 and this wavelength is amplified by the semiconductor optical amplifier module 380, modulated in phase by a phase modulator module 400, modulated at a bit-rate (e.g., 10 Gb/s or higher Gb/s, but a variable modulation bit-rate is preferred) in intensity by an intensity modulator module 420, amplified by the semiconductor optical amplifier module 380, transmitted through a variable optical intensity attenuator module 440 (if needed) and looped/returned back to create the upstream wavelength (embedded with an optical signal from the intelligent subscriber subsystem 340) and transmitted to the super node 101.

Furthermore, the generic intensity modulator module 140 can be replaced by an electro-absorption intensity modulator module 420, which is designed for integration with the semiconductor optical amplifier module 380, the phase modulator module 400 and the variable optical intensity attenuator module 440 on a monolithic photonic integrated circuit (PIC) and/or an active-passive hybrid planar lightwave circuit (PLC) technology.

Numerous permutations (e.g., modulating a CW optical signal from the laser module 120 at the local node 102 by the intensity modulator 140/420 and then by the phase modulator 400) of all optical modules within the optical processing micro-subsystem 360 are possible to create an optimum quality of the upstream wavelength for an intended reach. Use of the phase modulator module 400 and the intensity modulator module 420 together can reduce the Rayleigh backscattering effect on the propagation of optical signals, enabling a longer-reach optical access communication network between the super node 101 and the remote node 103, thus eliminating a vast array of middle equipment such as routers and switches, which would otherwise be needed between a standard node (without the super node configuration) and a large number of the remote nodes 103s, according to a currently deployed optical access communication network.

According to another embodiment of the present invention, an upstream second set of wavelengths (which are offset in wavelengths with respect to the first set of wavelengths transmitted from the super node 101) can be internally generated by a wavelength tunable laser module within the intelligent subscriber subsystem 340, without the need for external wavelength generation by the laser module 120 at the local node 102. Generation of the upstream wavelength (fast switching-widely tunable laser module is preferred) within the intelligent subscriber subsystem 340 simplifies fabrication and construction of a dynamic bidirectional optical access communication network 100.

According to another embodiment of the present invention, a single-mode/mode-hopp free wavelength tunable (about 32 nm) laser module can be constructed by utilizing an ultra-low anti-reflection coated (both facets) semiconductor optical amplifier (a quantum dot semiconductor optical amplifier is preferred) and a triple-ring resonator waveguide on a planar lightwave circuit platform. The front facet of the triple-ring resonator waveguide has an ultra-low anti-reflection coating, while the back facet of that has a high-reflection coating. The anti-reflection coated back facet of the semiconductor optical amplifier and the anti-reflection coated front facet of the triple-ring resonator waveguide are intimately attached ("butt-coupled") to each other. The phases of a triple-ring resonator waveguide can be controlled by a metal strip heater along a straight segment of the triple-ring resonator waveguide. Furthermore, the semiconductor optical amplifier 380 can be monolithically integrated with the electro-absorption (EAM)/Mach-Zehnder intensity modulator.

Figure 3A:
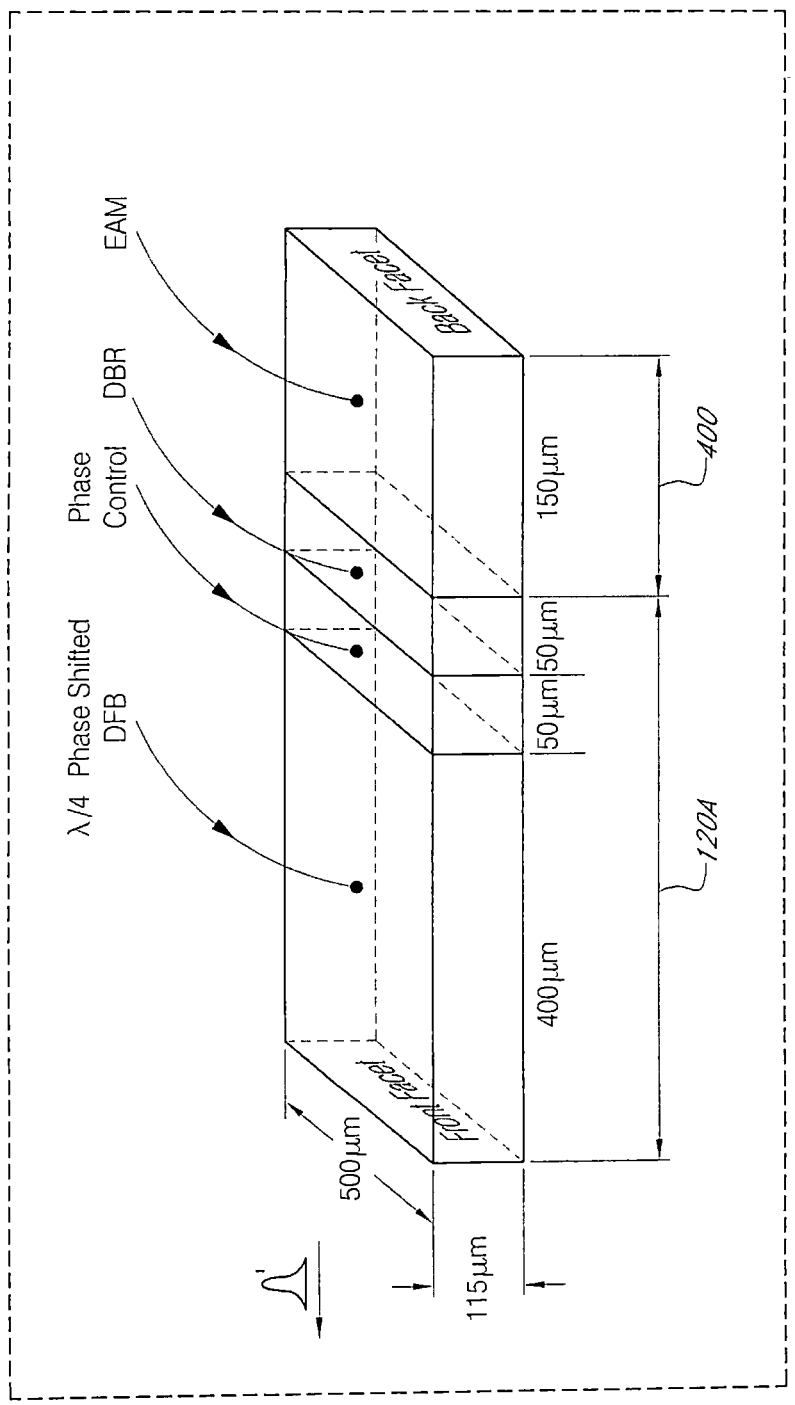
FIG. 3A illustrates a block diagram fabrication and construction of a wavelength tunable (narrowly) laser component, according to another embodiment of the present invention.

FIG. 3A illustrates a block diagram fabrication and construction of a single-mode/mode-hopp free wavelength tunable (narrow) laser component, including an electro-absorption modulator segment 400 (about 150 microns long), which can be integrated ("butt-coupled") with the back facet of a λ/4 phase shifted DR laser (λ/4 phase shifted distributed feedback (DFB) section (about 400 microns long)+phase control section (without any gratings/about 50 microns long)+distributed Bragg reflector. (DBR) section (about 50 microns long)) 120A. Laser multi-quantum-well (MQW) layers can be stacked on top of electro-absorption intensity modulator multi-quantum-well layers. An electro-absorption intensity modulator can be processed by etching away the laser multi-quantum-well layers. Higher laser output (exit power) can be achieved by incorporating distributed phase shifts and/or chirped grating across the length of a distributed feedback section. An injection current to a phase control section can produce a change in distributed feedback laser wavelength. Reverse-voltage to the electro-absorption intensity modulator 420 can change in a refractive index by Quantum Confined Stark Effect (QCSE). The advantages of this tunable laser design are (1) high single-mode stability due to a distributed feedback section, (2) higher output (exit) power due to a distributed Bragg reflector section and (3) rapid wavelength tuning by an injection current to a phase control section and/or reverse voltage to the electro-absorption intensity modulator 420.

A stacked multi-quantum well cross-sectional layer design of the electro-absorption modulator with the DR laser is illustrated in Table 1 below.

TABLE 1

| | Thickness (nm) | N-/P- Doping (10^18/cm^3) | Composition In(1-x)Ga(x)As(y)P(1-y) | Bandgap Wavelength (nm) | Strain (%) | Material Index |
|---|---|---|---|---|---|---|
| Substrate | 100 × 10^3 | N 3.0 | X = 0.000<br>Y = 0.000 | 918.6 | 0 | 3.1694 |
| Buffer | 1 × 10^3 | N 1.0 | X = 0.000<br>Y = 0.000 | 918.6 | 0 | 3.1694 |
| 1.15Q | 70 | N 0.5 | X = 0.181<br>Y = 0.395 | 1150 | 0 | 3.3069 |
| 1.20Q | 50 | N 0.5 | X = 0.216<br>Y = 0.469 | 1200 | 0 | 3.3345 |
| 1.10Q | 10 | N 0.001 | X = 0.145<br>Y = 0.317 | 1100 | 0 | 3.2784 |
| EAM Well-1 | 8 | N 0.001 | X = 0.463<br>Y = 0.930 | 1550 | TS0.2 | 3.5533 |
| 1.10Q | 6 | N 0.001 | X = 0.145<br>Y = 0.317 | 1100 | 0 | 3.2784 |
| EAM Well-2 | 8 | N 0.001 | X = 0.463<br>Y = 0.930 | 1550 | TS0.2 | 3.5533 |
| 1.10Q | 6 | N 0.001 | X = 0.145<br>Y = 0.317 | 1100 | 0 | 3.2784 |
| EAM Well-3 | 8 | N 0.001 | X = 0.463<br>Y = 0.930 | 1550 | TS0.2 | 3.5533 |
| 1.10Q | 6 | N 0.001 | X = 0.145<br>Y = 0.317 | 1100 | 0 | 3.2784 |
| EAM Well-4 | 8 | N 0.001 | X = 0.463<br>Y = 0.930 | 1550 | TS0.2 | 3.5533 |
| 1.10Q | 6 | N 0.001 | X = 0.145<br>Y = 0.317 | 1100 | 0 | 3.2784 |
| EAM Well-5 | 8 | N 0.001 | X = 0.463<br>Y = 0.930 | 1550 | TS0.2 | 3.5533 |
| 1.10Q | 6 | N 0.001 | X = 0.145<br>Y = 0.317 | 1100 | 0 | 3.2784 |
| EAM Well-6 | 8 | N 0.001 | X = 0.463<br>Y = 0.930 | 1550 | TS0.2 | 3.5533 |
| 1.10Q | 10 | N 0.001 | X = 0.145<br>Y = 0.317 | 1100 | 0 | 3.2784 |
| Stop-Etch | 50 | N 0.001 | X = 0.000<br>Y = 0.000 | 918.6 | 0 | 3.1694 |
| *1.25Q | 10 | N 0.001 | X = 0.239<br>Y = 0.533 | 1250 | 0 | 3.3588 |
| *DR Well-1 | 5 | N 0.001 | X = 0.239<br>Y = 0.839 | 1642 | CS1.05 | 3.4971 |
| *1.25Q | 10 | N 0.001 | X = 0.239<br>Y = 0.533 | 1250 | 0 | 3.3588 |
| *DR Well-2 | 6 | N 0.001 | X = 0.239<br>Y = 0.839 | 1642 | CS1.05 | 3.4971 |
| *1.25Q | 10 | N 0.001 | X = 0.239<br>Y = 0.533 | 1250 | 0 | 3.3588 |
| *DR Well-3 | 5 | N 0.001 | X = 0.239<br>Y = 0.839 | 1642 | CS1.05 | 3.4971 |
| *1.25Q | 10 | N 0.001 | X = 0.239<br>Y = 0.533 | 1250 | 0 | 3.3588 |
| *DR Well-4 | 6 | N 0.001 | X = 0.239<br>Y = 0.839 | 1642 | CS1.05 | 3.4971 |
| *1.25Q | 10 | N 0.001 | X = 0.239<br>Y = 0.533 | 1250 | 0 | 3.3588 |
| *1.20Q | 50 | P 0.2 | X = 0.216<br>Y = 0.469 | 1200 | 0 | 3.3345 |
| **Grating: 1.15Q | 50 | P 0.2 | X = 0.181<br>Y = 0.395 | 1150 | 0 | 3.3069 |
| Cladding | 1.5 × 10^3 | P 0.2~P 2.0 | X = 0.000<br>Y = 0.000 | 918.6 | 0 | 3.1694 |
| 1.30Q | 50 | P 5.0 | X = 0.280<br>Y = 0.606 | 1300 | 0 | 3.3871 |
| Cap | 200 | P 30 | X = 0.468<br>Y = 1.000 | 1654 | 0 | 3.5610 |

EAM: Electro-absorption modulator
DR: Laser
TS: Tensile
CS: Compressive

*These laser layers must be removed in EAM section and be replaced/re-grown with InP layer of total thickness of ~172 nm.
**λ/4 phase shifted gratings (at the DFB section of DR laser) are fabricated on this layer with 50% duty cycle at 40 nm grating etch depth.

Figure 3B:
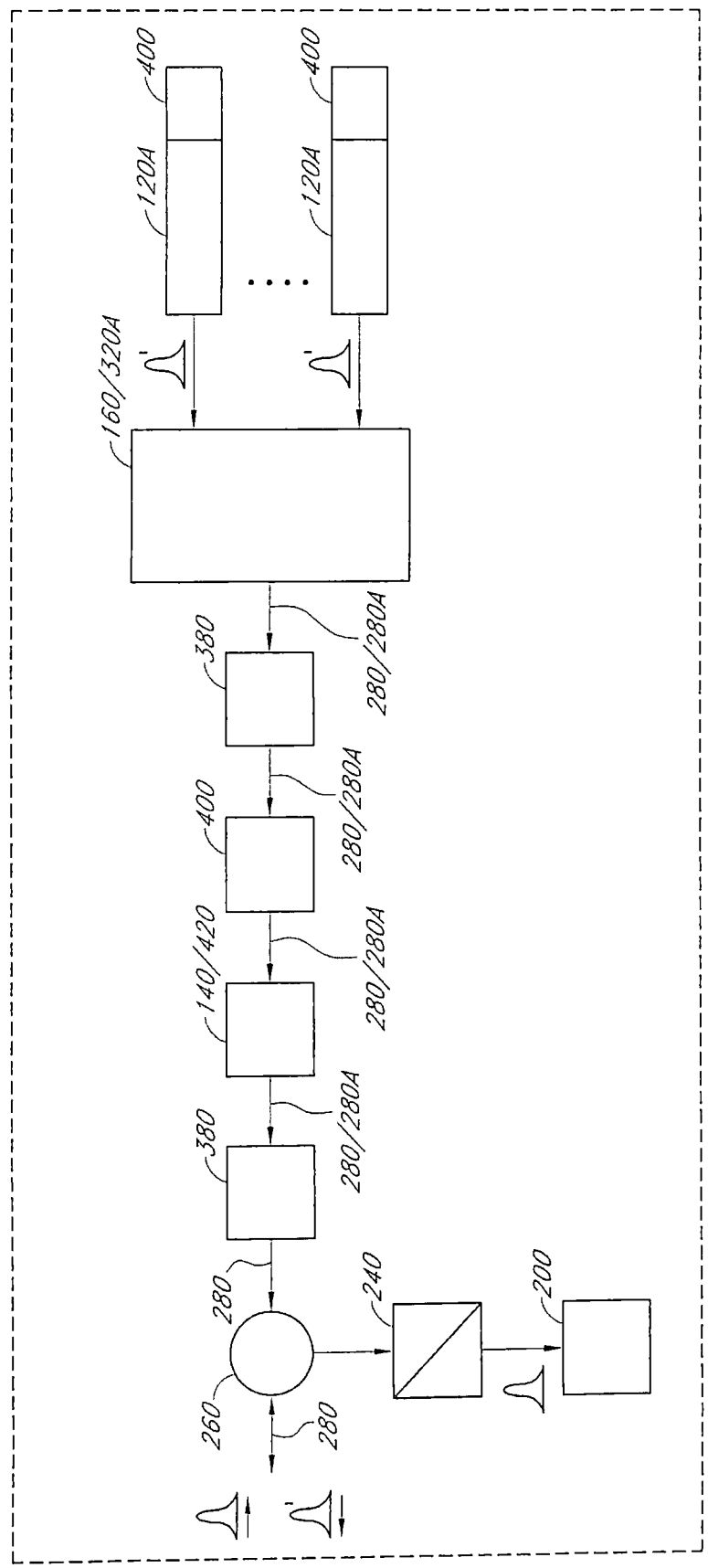
FIG. 3B illustrates a block diagram fabrication and construction of a wavelength tunable (widely) laser array module, according to another embodiment of the present invention.

FIG. 3B illustrates a block diagram fabrication and construction of a single-mode/mode-hopp free wavelength tunable (widely) laser array, which can be integrated with the wavelength combiner 160 or the Y/multi-mode interference optical power combiner 320A, the tilted/curved semiconductor optical amplifier 380, the phase modulator 400 (if needed), the intensity modulator 140/420 and the tilted/curved semiconductor optical amplifier 380 via a waveguide 280A/single-mode fiber 280. The back facet of the electro-absorption modulator segment 400 has a low anti-reflection coating, while the front facet of the last optical amplifier 380 has an ultra-low anti-reflection coating. The upstream wavelength (embedded with an optical signal) generated utilizing the tunable laser module at the intelligent subscriber subsystem 340, is passed through the 3-port circulator module 260 at the remote node 103 and transmitted to the super node 101. The downstream wavelength from the super node 101, is passed through the 3-port circulator 260, the bandpass optical filter module 240 and the photodiode module 200 at the remote node.

According to another embodiment of the present invention, a subset of a second set of wavelengths (which are offset in wavelengths with respect to a first set of wavelengths transmitted from the super node 101) can be modulated at a bit-rate (e.g., 10 Gb/s or higher Gb/s, but a variable modulation bit-rate is preferred) and thus configured to be shared with a number of intelligent subscriber subsystems 340s to generate a symmetric upstream bandwidth/bandwidth on-Demand.

Both downstream and upstream wavelengths can be protected by a 2×2 optical protection switch module and separated via an optical ring-network including redundant/multiple dispersion-compensated single-mode optical fibers 280s.

A pilot tone modulation can be added to the semiconductor optical amplifier module 380 within the optical processing micro-subsystem 360 (within the intelligent subscriber subsystem 340) and to the laser modules 120s (at the super node 101 and the local node 102) to reduce the Rayleigh backscattering effect.

An electronic dispersion compensation circuit and a forward error correction circuit can be added to relax the specifications of the optical and/or electronic modules. Furthermore, all optical single-mode fibers can be polished at an angle (about 7 degree) to reduce any optical back-reflection.

According to another embodiment of the present invention, an upstream wavelength may be shared/transmitted by several of the intelligent subscriber subsystems 340s, utilizing a time division multiplexed statistical bandwidth allocation method. Therefore, a burst mode receiver circuit is needed at the super node 101 to process bursty optical signals embedded in the upstream wavelengths from several of the intelligent subscriber subsystems 340s.

Furthermore, to enable a higher bit-rate, a modulator/demodulator of an advanced modulation format (e.g., differential quadratic phase-shift keying-DQPSK and/or quadratic amplitude modulation-QAM) can be utilized.

Figure 4:
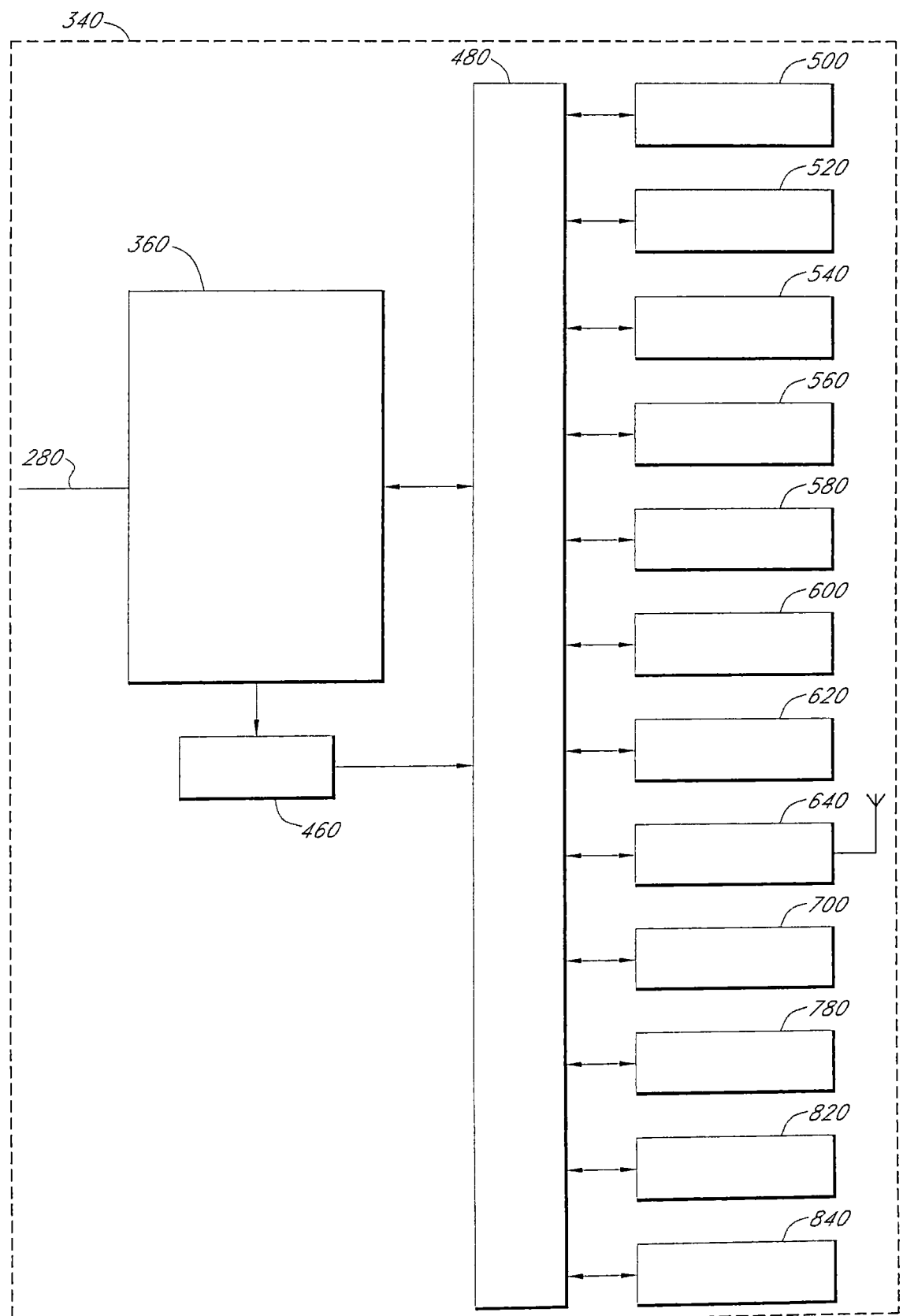
FIG. 4 illustrates a block diagram fabrication and construction of an intelligent subscriber subsystem 340, according to another embodiment of the present invention.

FIG. 4 illustrates a block diagram fabrication and construction of the intelligent subscriber subsystem 340, according to another embodiment of the present invention, wherein the intelligent subscriber subsystem 340 includes the optical processing micro-subsystem 360 (for separating and providing the downstream wavelength to the photodiode module 200 and optically processing the upstream wavelength to the super node 101). The photodiode module 200 within the optical processing micro-subsystem 360 is connected/coupled/interacted with an optical-to-electrical amplifier circuit 460 and a media access controller (with processing, routing and quality of service (QOS) functions) module and module specific software 480. The media access controller module and module specific software 480 are connected/coupled/interacted with one or more of the following: (a) an IP/micro IP/light weight IP address module and module specific software 500, (b) a security module (an internet firewall/spyware/user-specific security control/authentication) and module specific software 520, (c) an in-situ/remote diagnostic module and module specific software 540, (d) a content transfer module and module specific software 560, (e) a time-shift (time-shift is a recording of content to a storage medium for consuming at a later time) module and module specific software 580, (f) a place-shift (place-shift is consuming stored content on a remote appliance/subsystem/system/terminal via the internet) module and module specific software 600, (g) a content (voice-video-multimedia-data) over-IP module and module specific software 620, (h) a radio module (with antenna(s)), wherein the radio module includes one or more of the following modules: RFID (active/passive), Wibree, Bluetooth, Wi-Fi, Zigbee (Zigbee is an IEEE 802.15.4-based specification), ultra-wideband, 60-GHz/millimeter wave, Wi-Max/4G/higher frequency radio and an indoor/outdoor position module (e.g., Bluetooth, Wi-Fi, GPS and an electronic compass) and module specific software 640, (i) a software module 700, which includes one or more of the following: embedded/cloud based operating system software and embedded/cloud based intelligence rendering software (e.g., surveillance software, behavior modeling (e.g., www.choicestream.com), predictive analytics/text/data/pattern mining/natural language processing (NLP) algorithm (e.g., www.sas.com), a fuzzy logic/artificial intelligence/neural network algorithm (e.g., www.nd.com/bliasoft.com), a machine learning/iterative learn-by-doing/natural learning algorithm (e.g., www.saffron.com) and an intelligent agent (e.g., www.cougaarsoftware.com)), (j) a memory/storage module and module specific software 780, (k) a sensor module and module specific software 820 and (l) a battery/solar cell/micro fuel-cell/wired power supply module and module specific software 840. A specific artificial intelligence/neural network algorithm may not be commercially available. However, one or more parts of a specific artificial intelligence/neural network algorithm (e.g., as in FIG. 16) and/or one or more parts of a specific neuro-fuzzy logic algorithm can be realized by integrating one or more above mentioned algorithms in (i).

The intelligent subscriber subsystem 340 can be cloud based interacting with a user. The intelligent subscriber subsystem 340 can be a user cloud based subsystem or a cloud based subsystem.

Furthermore, a System-on-a-Chip integrating a central processor module and module specific software 760 with a graphic processor module, an internet firewall security system, spyware and the user-specific security control/authentication can simplify fabrication and construction of the intelligent subscriber subsystem 340. It should be noted that the System-on-a-Chip can process module specific software 760, coupled with the System-on-a-Chip. Generally, such module specific software 760 can be embedded (and even stored) with the System-on-a-Chip or alternatively, if the electrical power consumption is a problem; such module specific software 760 can be in a remote/cloud server (safer with extensive firewall protection is desired and can be accessed by the System-on-a-Chip over the internet, but latency may be issue).

However, the System-on-a-Chip may include a video encoder, a video decoder, a computer vision processor and it may also include an artificial intelligence/machine learning accelerator—is a specialized hardware accelerator/computer system.

In one embodiment the System-on-a-Chip may include one or more central processors and/or graphic processors, wherein the central processors and/or graphic processors can be stacked in a three-dimensional arrangement for scaling the performance. It should be noted that a three-dimensional arrangement can include a vertical arrangement.

A possible method of a three-dimensional arrangement/vertical arrangement is hybrid bonding.

In hybrid bonding, copper pads can be built on the top face of each (extremely flat via chemical mechanical planarization (CMP)) chip. These copper pads can be surrounded by silicon oxide or silicon carbonitride and these copper pads themselves are slightly (nanoscaled) recessed from the surface of silicon oxide or silicon carbonitride. Two chips (extremely flat) can be pressed together face-to-face, so that the recessed copper pads on each (extremely flat) chip align. This sandwich structure is then slowly heated/annealed at a relatively high temperature (e.g., about 300 degrees centigrade), causing the copper pads to expand across the gap and fuse, connecting the two (extremely flat) chips at about 2 to 5 microns pitch.

Although, the copper pads from two (extremely flat) chips can align/press together to form an electrical connection, copper metal's grain boundaries generally may not easily cross from one side of one (extremely flat) chip to the other side of another (extremely flat) chip to merge as large single grains of copper to form across the boundary to improve electrical conductance and stability.

However, copper can be replaced by a suitable nanocomposite (e.g., consisting of (i) a polystyrene-block-polymethylmethacrylate and iron compounds or (ii) polystyrene and gold nanoparticles or (iii) polymethylmethacrylate and gold nanoparticles).

A central processor has electronic circuits, which can generally execute such as arithmetic, logic, controlling and input/output (I/O) operations. A graphic processor has electronic circuits, which can generally execute such as digital image processing, computer graphics and parallel processing.

Alternatively, central processors and/or graphic processors can be coupled with an optical switch or an optical interface, wherein the optical interface can include light sources and photodiodes.

Alternatively, central processors and/or graphic processors can be a part of a multichip module (MCM), wherein the multichip module (MCM) includes an array of light sources, an array of photodiodes and an array of lenses.

Details of an optical switch/optical interface and a multichip module have been described/disclosed in U.S. Non-Provisional patent application Ser. No. 17/803,388 entitled "SUPER SYSTEM ON CHIP", filed on Jun. 15, 2022 and in its related U.S. non-provisional patent applications (with all benefit provisional patent applications) are incorporated in its entirety herein with this application.

The System-on-a-Chip is designed to accelerate artificial intelligence/machine learning, including artificial neural networks (ANN), machine vision and on-sensor processors (utilizing one or more on-sensor processing circuits e.g., digital signal processing (DSP) circuits), where both input signals and output signals can be encrypted. It can be a high-performance parallel computation machine that is specifically designed for the efficient processing of artificial intelligence/machine learning workloads like artificial neural networks.

In another embodiment the System-on-a-Chip (which can be also coupled with a voice processing module (the voice processing module can consist of one or more electronic components) can include (i) central processors/processor-specific electronic circuits (EICs) and/or (ii) graphic processors/processor-specific electronic circuits and/or (ii) matrix multipliers to multiply (generally a series of) matrices.

Generally, a processor-specific electronic circuit can include one or more central processors and/or one or more graphic processors. A processor-specific electronic circuit can have one or more multipliers of matrices and on-sensor processors. However, a graphic processor may act as a multiplier of matrices. In this case, an image can be split into small patches and each patch can be turned into a row in a matrix. The filters or kernels used in the convolution are represented as columns in another matrix, with each column containing the weights of a kernel. The result is obtained by performing a matrix multiplication between these two matrices.

Furthermore, the System-on-a-Chip can include multiple processing cores (of a central processor) and memory units (e.g., each memory unit can include one or more memory elements. Each memory element can include one or more memory circuits). Also, the multiple processing cores (of a central processor/processor-specific electronic circuit) and multiple memory units (of the same central processor) can be coupled in an intertwined (interwoven/twisted together) geometrical pattern either in a two-dimensional arrangement or a three-dimensional (3-D) arrangement, wherein a memory unit can include one or more memory elements, wherein a memory element can include one or more memory circuits. This arrangement is without a centralized memory (rather it is memory near computation (processing) in a central processor). Such a System-on-a-Chip at least in part may enable non-von Neumann computation architecture including compute-near-memory (CNM) or computer-in-memory (CIM)

Above embodiment of the System-on-a-Chip (enabling non-von Neumann computation architecture) can also include one or more graphic processors and on-sensor processors (utilizing one or more on-sensor processing circuits e.g., digital signal processing circuits), where both input signals and output signals can be encrypted. Furthermore, graphic processors can be stacked in a three-dimensional arrangement for scaling the performance. It should be noted that a three-dimensional arrangement can include a vertical arrangement.

Furthermore, above embodiment of the System-on-a-Chip (enabling non-von Neumann computation architecture) can include one or more multipliers of matrices.

Furthermore, it should be noted that the above System-on-a-Chip (enabling non-von Neumann computation architecture) can process module specific software 760. Generally, such module specific software 760 can be embedded (and even stored) with the above System-on-a-Chip or alternatively, if the electrical power consumption is a problem; such module specific software 760 can be in a remote/cloud server (and can be accessed by the System-on-a-Chip over the internet, but latency may be an issue).

Various combinations (i) central processors/processor-specific electronic circuits and/or (ii) graphic processors/processor-specific electronic circuits and/or (ii) matrix multipliers to multiply (generally a series of) matrices, including module specific software 760 are possible within the context of the above System-on-a-Chip.

Various embodiments of the Super System on Chip (including optically enabled Super System on Chip) and/or the System-on-a-Chip are designed to accelerate artificial intelligence/machine learning, including artificial neural networks (ANN), machine vision and on-sensor processors (utilizing one or more on-sensor processing circuits e.g., digital signal processing circuits), where both input signals and output signals can be encrypted. It can be a high-performance parallel computation machine that is specifically designed for the efficient processing of artificial intelligence/machine learning workloads like artificial neural networks.

Various embodiments of the Super System on Chip (including optically enabled Super System on Chip) and/or the System-on-a-Chip may be augmented with a quantum computing system that includes a quantum processing unit (QPU) of qubits.

For example, the trapped ions are among the most promising systems for practical quantum computing. A quantum processing unit of a chain of single ions in a cryogenic vacuum may also include a chip-scale electronic integrated input/output circuit (EIC-I/O) and a chip-scale photonic integrated input/output circuit (PIC-I/O).

A chain of single ions for a quantum processing unit can be created by local ionization of neutral atoms (e.g., Ca, Ba, Be or Sr). Since ions are charged, they can be controlled by electrical fields or electromagnetic fields in chip-scale ion traps for loading and trapping of ions.

Generally, a chip-scale electronic integrated input/output circuit can include monolithically integrated (i) trench capacitors for electrical filtering, (ii) through substrate vias for electrical connections to route voltage signals around the ion traps and current lines to generate magnetic fields, (iii) on-chip digital-to-analog converters (DACs), (iv) on-chip analog processing circuits, (v) on-chip digital processing circuits and (vi) on-chip avalanche photodiodes to detect fluorescence from the ion traps.

Generally, a chip-scale photonic integrated input/output circuit can include monolithically integrated (i) different and distinct low-loss and smooth edged optical waveguides (e.g., made of silicon nitride ($SiN_x$), gallium nitride (GaN), aluminum nitride (AlN), lithium niobate ($LiNbO_3$) or alumina ($Al2O_3$)) (ii) vertical grating couplers for each distinct wavelength (color) (with inputs from a low-loss optical ring resonator(s) based optical switch and/or an array of modulators and/or an array of semiconductor lasers in UV to visible wavelength (color)) to allow a laser beam of a distinct wavelength (color) through a hole (e.g., fabricated on a metal thin-film) of a chip-scale photonic integrated input/output circuit to reach and manipulate the ion trap, located on top of the hole. The hole can be designed to reduce light diffraction for reduced cross talk. However, an array of semiconductor lasers can be optically coupled with a chip-scale photonic integrated input/output circuit via low-loss spot-size converters (e.g., inverse taper type spot-size converters with knife-edge tapers).

Furthermore, the vertical grating couplers for each distinct wavelength (color) can be located at a fraction of a micron below the ion trap.

Furthermore, an ultrafast optical switch with about nano-seconds optical switching time can be fabricated/constructed utilizing Mach-Zehnder interferometer with a phase transition material (e.g., vanadium dioxide) in UV to visible wavelength (color) range.

The intelligent subscriber subsystem 340 includes a set top box/personal video recorder/personal server component/module. The intelligent subscriber subsystem 340 includes a voice-to-text-to-voice processing module and module specific software. (e.g., Crisp Sound is real-time audio signal processing software for echo cancellation, background noise reduction, speech enhancement and equalization), a video compression module and module specific software, a photo-editing software module and a software module for automatically uploading content to a remote/cloud server.

The intelligent subscriber subsystem 340 has multiple radio modules with multiple antennas. A tunable radio-frequency carbon nanotube (CNT) cavity can tune in between 2 GHz and 3 GHz. The merger of many antennas, utilizing a tunable carbon nanotube cavity and an analog/digital converter can enable a simplified software-defined radio.

The intelligent subscriber subsystem 340 can enable content over-IP, (e.g., Skype service) thus disrupting a traditional carrier controlled fixed telephony business model.

According to another embodiment of the present invention, the secure delivery of a content optical signal to an intended destination can be achieved by utilizing a low bit-rate destination marker optical signal, which is modulated at a different plane with a different modulation format, simultaneously in conjunction with a higher-bit rate content optical signal. The low bit-rate destination marker optical signal is extracted and converted from an optical domain to an electrical domain to determine the intended destination of the content optical signal, while the content optical signal remains in an optical domain until it is delivered to the intended destination—thus both routing and security in the delivery of the content optical signal can be significantly enhanced.

Figure 5:
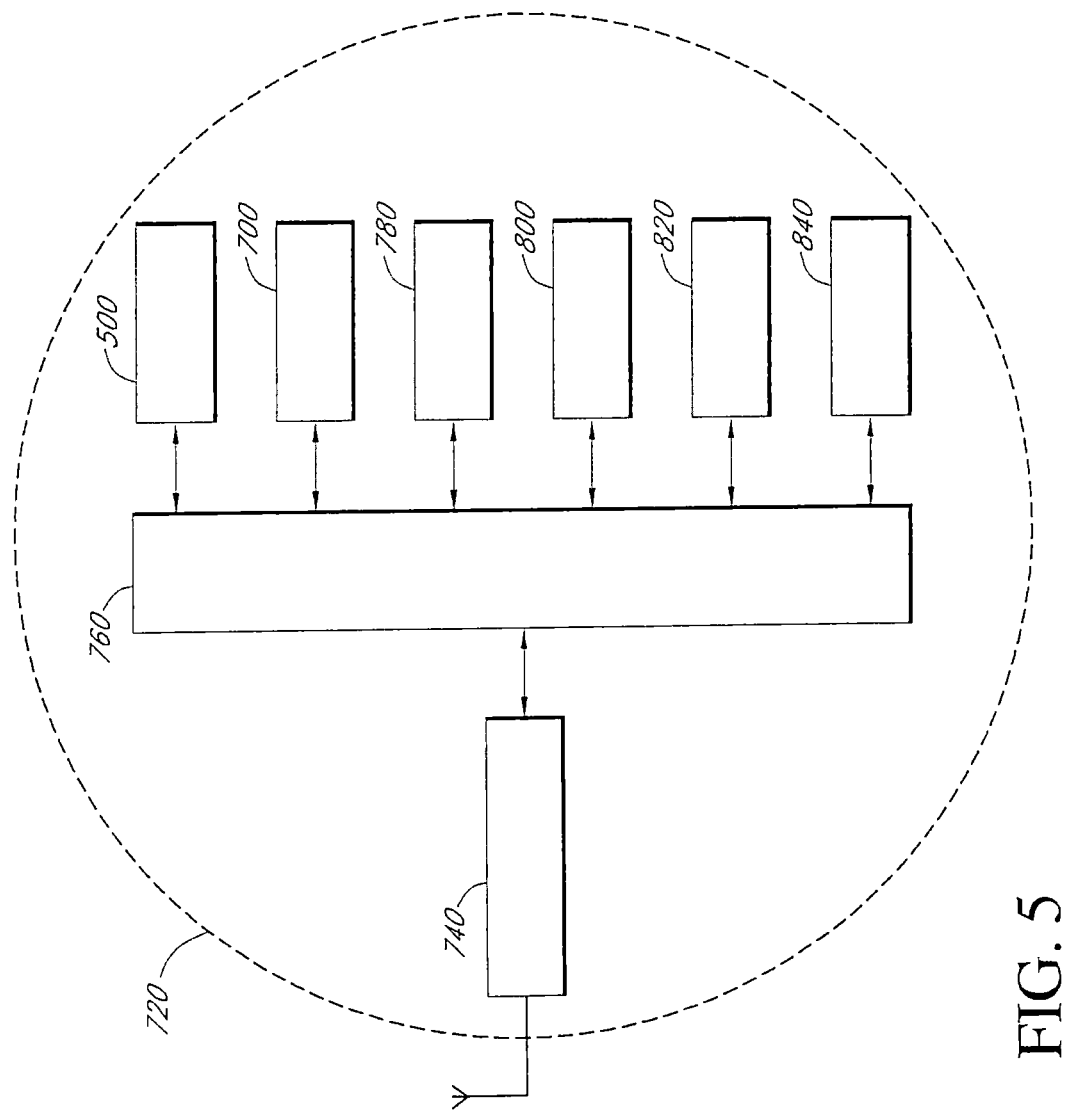
FIG. 5 illustrates a block diagram fabrication and construction of an object 720, according to another embodiment of the present invention.

FIG. 5 illustrates a block diagram fabrication and construction of a microsized (about 15 $mm^3$) object 720, having a processor (e.g., ultra-lower power consumption ARM Cortex™-M3/microcontroller-www.ambiqmicro.com/based on nanoscaled InAs XOI) module and module specific software 760 that is connected/coupled/interacted with one or more of the following: (a) an IP/micro IP/light weight IP address module and module specific software 500, (b) a software module 700 (e.g., a Tiny OS-operating system/IBM mote runner), (c) an "object specific" radio module with antenna(s) (which includes one or more of the following: RFID (active/passive), an ultra-low power radio, Wibree, Bluetooth and near-field communication 740, (d) a memory/storage module and module specific software 780, (e) a camera module (a micro-electrical-mechanical-system based camera is preferred) and module specific software 800, (f) a sensor (e.g., a radio enabled micro-electro-mechanical sensor) module and module specific software 820 and (g) a battery/solar cell/micro fuel-cell wired power supply/wired power supply module and module specific software 840. For example, a microsized object 720 can also be realized utilizing either a conductive paint or spray-on sensor(s) on a wall. Such a wall can be an interactive surface and it may sense human touch, human gestures and interact with other sensors at a home/office.

A battery/solar cell (e.g., silicon)/micro fuel-cell/wired power supply/resonant electromagnetic inductive coupling energy transfer (wireless) power supply module and module specific software 840 can include a thick/thin-film (e.g., 3.6V-12 µAh Cymbet thin-film lithium battery) printed/three-dimensional/nano-engineered battery (e.g., cellulose-a spacer ionic liquid electrolyte, electrically connected/coupled/interacted with a carbon nanotube electrode and a lithium oxide electrode), a nano supercapacitor (e.g., utilizing carbon nanotube ink or operating due to fast ion transport at a nanoscale), a nano-electrical generator of piezoelectric PZT nanowires (e.g., 20,000 n-/p-type zinc oxide nanowires can generate about 2 mW), a nano-electro-mechanical systems (NEMS) cell (e.g., a motor protein cell) and a microbial nano fuel-cell.

A motor protein (macromolecule) named prestin, which is expressed in outer hair cells in the organ of Corti of a human ear and is encoded by the SLC26A5 gene. Prestin converts an electrical voltage into a motion by elongating and contracting outer hair cells. This motion amplifies sound in a human ear. However, prestin can work in a reverse mode, producing an electrical voltage in response to a motion. To increase conductivity, a microbe (e.g., a bacterium Pili) can act as a conducting nanowire to transfer electrons generated by prestin. Each prestin cell can make only nano watts of electricity. A prestin cell (array of prestins connected/coupled/interacted between two electrodes) can electrically charge a battery/micro fuel-cell/wired power supply module. A prestin cell can grow and self-heal, as it is constructed from biological components. Furthermore, a nano-electrical generator of piezoelectric PZT nanowires can be integrated with prestin.

A memristor component can replace both the processor component and/or the memory/storage component. Furthermore, a memristor component and a nano-sized radio component can reduce power consumption of the object 720.

A sensor module and module specific software 820 can include a biosensor (e.g., to monitor/measure body temperature, % oxygen, heart rhythm, blood glucose concentration and a biomarker for a disease parameter).

The object 720 with a biosensor, a transistor, a light emitting diode, a nano-sized radio, a prestin cell (for electrical power) and an object specific software can be incorporated onto a support material (e.g., a silk membrane) to monitor/measure (and transmit) a disease parameter.

Another example of a biosensor sensor can be an assassin protein (macromolecule) perforin, the immune system's weapon of mass destruction. Perforin is encoded by the PRF1 gene. Perforin is expressed in T cells and natural killer (NK) cells. Interestingly, perforin resembles a cellular weapon employed by a bacterium (e.g., anthrax). Perforin can embed itself to form a pore in a cell membrane. The pore by itself may be damaging to a cell and it enables the entry of a toxic enzyme granzyme B, which induces apoptosis (a programmed suicide process) of a diseased cell. However, perforin occasionally misfires-killing the wrong cell (e.g., an insulin producing pancreas) and significantly accelerating a disease like diabetes. Defective perforin leads to an upsurge in cancer malignancy (e.g., leukemia). Upregulation of perforin can be effective against cancer and/or an acute viral disease (e.g., cerebral malaria). The downregulation of perforin can be effective against diabetes. The ramification of a pore-forming macromolecule like perforin is enormous if it can be tailored/tuned to a specific disease.

Like perforin, ultrasonically guided microbubbles can break into a cell membrane. A pore-forming microbubble (ultrasonically guided)/nanovessel (e.g., a cubisome/liposome) encapsulating a suitable chemical(s)/drug(s), a surface modified red fluorescent protein (e.g., E2-Crimson) and perforin (if needed) can be an effective imaging/drug delivery method. A surface coating (e.g., a pegylation) on the microbubble/nano vessel can avoid the immune surveillance of a human body. A surface coating of disease-specific ligand (e.g., an antibody) on a microbubble/nano-vessel can enhance the targeting onto specific disease cells. Furthermore, an encapsulation of magnetic super-paramagnetic nanoparticles within a microbubble/nano-vessel can significantly enhance the targeting to specific disease cells when it is guided by a magnet. The microbubbles/nano-vessels can be incorporated within a silicone micro catheter (coated with silver nanoparticles) tube or a micro-electrical-mechanical-system reservoir/micropump (integrated with an array of silicon microneedles) on a support material.

For utilizing the object 720 within and/or on a human body, all components must be biocompatible (biodissolvable may be preferred).

If a disease parameter measurement is perceived to be abnormal with respect to a reference disease parameter measurement, a biosensor module connects/couples/interacts with the object 720 for a programmed drug delivery. Furthermore, the object 720 can connect/couple/interact (via one/more/all the networks as listed hereinafter: electrical/optical/radio/electromagnetic/sensor/biosensor communication network(s)) with another object 720, the intelligent subscriber subsystem 340 and/or an intelligent appliance 880 for location based/assisted emergency help without human input.

The object 720 can be fabricated/constructed, utilizing a System-on-a-Chip/System-in-a-Package module. The object 720 (SiP)/multi-chip can sense/measure/collect/aggregate/compare/map and connect/couple/interact/share (via one/more/all the networks as listed hereinafter: electrical/optical/radio/electromagnetic/sensor/biosensor communication network(s)) with another object 720), the intelligent subscriber subsystem 340 and the intelligent appliance 880, utilizing internet protocol version 6 (IPv6) and its subsequent versions.

A method of securing information by the object 720, includes at least the following steps: (a) sensing 900, (b) measuring 920, (c) collecting 940, (d) aggregating/comparing/mapping 960, (e) connecting/coupling/interacting/sharing 980 (in real-time) with the plurality of objects 720*s*, intelligent subscriber subsystems 340*s* and intelligent appliances 880*s*, (f) developing a learning algorithm (e.g., a machine learning/iterative learn-by-doing/natural learning algorithm in a software module 700) 1300 from the activities of the plurality of objects 720*s*, intelligent subscriber subsystems 340*s* and intelligent appliances 880*s*, (g) utilizing a learning algorithm 1320 and (h) re-iterating all the previous steps from (a) to (g) in a loop cycle 1340 to enable intelligent decision based on information from the plurality of objects 720*s*, the intelligent subscriber subsystems 340*s* and the intelligent appliances 880*s*.

Figure 6:
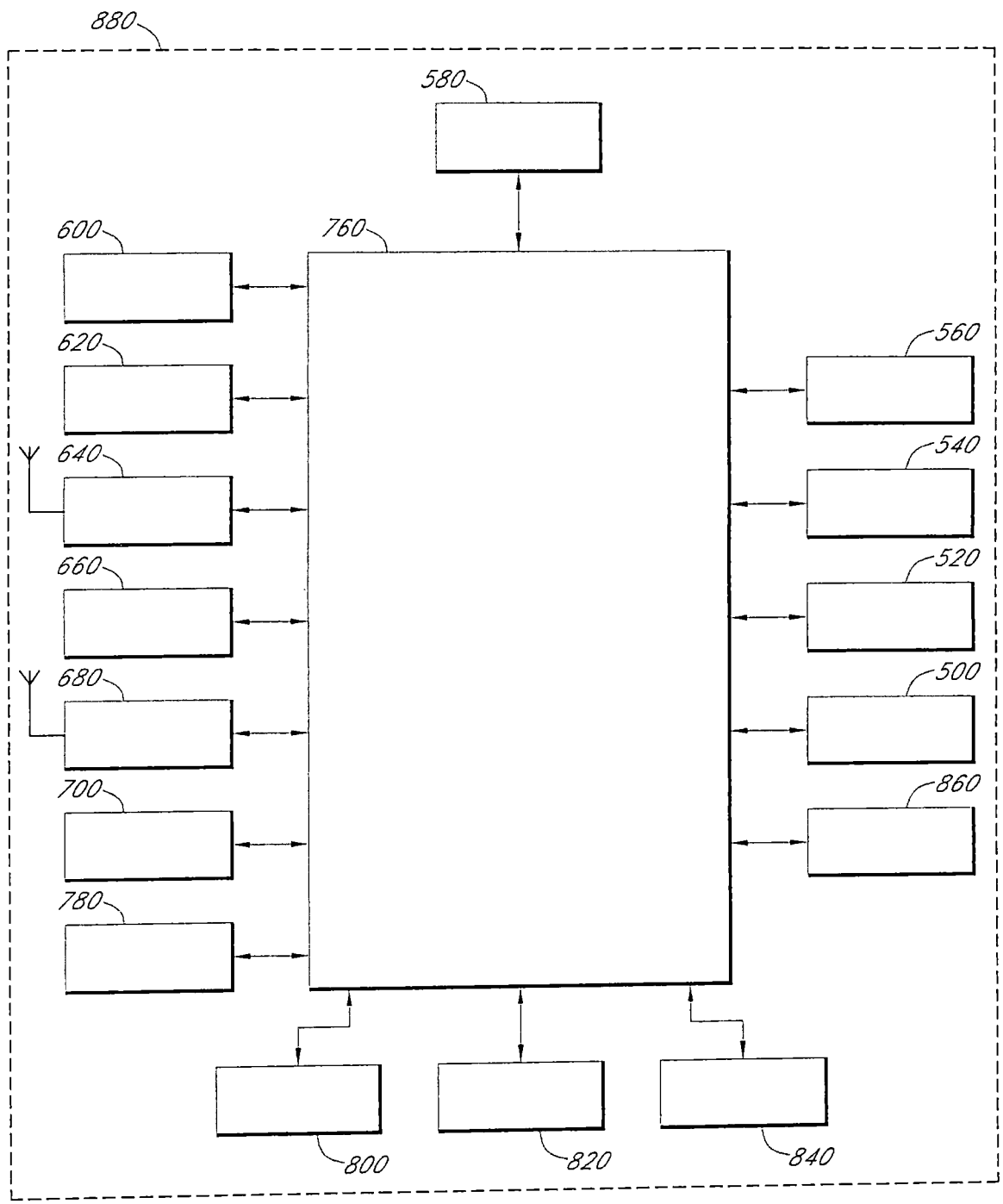
FIG. 6 illustrates a block diagram fabrication and construction of an intelligent appliance 880, according to another embodiment of the present invention.

FIG. 6 illustrates a block diagram fabrication and construction of the intelligent appliance (about 125 mm long, 75 mm wide and 20 mm thick) 880, according to another embodiment of the present invention. A processor (performance at a lower electrical power consumption is desired e.g., graphene based processor) module and module specific software 760 are connected/coupled/interacted (via one/more/all the networks as listed hereinafter: electrical/optical/radio/electromagnetic/sensor/biosensor communication network(s) with another intelligent appliance) with one or more of the following: (a) an IP/micro IP/light weight IP address module and module specific software 500, (b) a security module (an internet firewall/spyware/user-specific security control/authentication) and module specific software 520, (c) an in-situ/remote diagnostic module and module specific software 540, (d) a content transfer module and module specific software 560, (e) a time-shift module and module specific software 580, (f) a place-shift module and module specific software 600, (g) a content (voice-video-multimedia-data) over-IP module and module specific software 620, (h) a radio module (with antenna(s)), wherein the radio module includes one or more of the following modules: RFID (active/passive), Wibree, Bluetooth, Wi-Fi, ultra-wideband, 60-GHz/millimeter wave, Wi-Max/4G/higher frequency radio and an indoor/outdoor position module (e.g., Bluetooth, Wi-Fi, GPS and an electronic compass) and module specific software 640, (i) an one-dimensional/two-dimensional barcode/quick response (QR) code scanner/reader module and module specific software 660, (j) a near-field communication module (with an antenna) and module specific software 680, (k) a software module 700, which includes one or more of the following: embedded/cloud based operating system software and embedded/cloud based intelligence rendering software (e.g., surveillance software, behavior modeling (e.g., www.choicestream.com), predictive analytics/text/data/pattern mining/natural language processing algorithm (e.g., www.sas.com), a fuzzy logic/artificial intelligence/neural network algorithm (e.g., www.nd.com/bliasoft.com), machine learning/iterative learn-by-doing/natural learning algorithm (e.g., www.saffron.com) and an intelligent agent (e.g., www.cougaarsoftware.com)), (l) a memory/storage module and module specific software 780, (m) a camera (a 180 degree-angle rotating camera module is preferred) and module specific software 800, (n) a sensor module and module specific software 820, (o) a battery (e.g., graphene material based battery)/solar cell/micro fuel-cell/wired power supply module and module specific software 840 and (p) a display (a foldable/stretchable display component with a touch sensor or a photonic crystal or a holographic display may be preferred) module and module specific software 860. An intelligent appliance 880 includes a socket (e.g., SIM/SD).

Additionally, a photonic crystal based display component can include one or more nanostructures.

Details of the photonic crystal based display component including one or more nanostructures have been described/disclosed in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

The touch sensor can include microfluidic channels to drive small amounts of liquid into invisible pockets, which can be instantly filled with a clear liquid to enable physically raising the buttons.

The intelligent appliance 880 can be cloud based interacting with a user. The intelligent appliance 880 can be a user cloud based subsystem or a cloud based subsystem.

Furthermore, a camera can include a tunable focal length liquid lens. A sealed transparent (to an optical/viewing axis) optical cell can contain two immiscible (e.g., water and oil) liquids, having equal physical (not optical) densities. A pair of piezoelectric sensors/motors can be mechanically coupled (perpendicular to the optical/viewing axis) with the sealed transparent (optical cell). By applying voltage inputs to each piezoelectric sensor/motor, mechanically coupled with the sealed transparent (optical cell), the geometrical shape of one of the immiscible liquids can be changed rapidly-making a variable/tunable focal length (liquid) lens. Instead of a pair of piezoelectric sensors/motors, a pair of vanadium dioxide based piezoelectric sensors/motors can be used. Vanadium dioxide is an insulator at a room temperature, but abruptly becomes an electrical (but, not thermal) conductor at about 67° C. This temperature driven phase transition from insulator-to-metal (IMT) occurs in a time scale of milliseconds (even nanoseconds). Furthermore, vanadium dioxide (lattice) crystal also undergoes a temperature driven structural phase transition, whereby when heated the crystal rapidly contracts along one axis, while expanding along the other two axes. Thus, vanadium dioxide can enable a miniaturized piezoelectric sensor/motor. The heating of the vanadium dioxide to actuate as a miniaturized piezoelectric sensor/motor can be done with a heating pad. Furthermore, as vanadium dioxide absorbs light, it converts into heat, thus the actuation can be triggered opto-thermally.

Furthermore, a display component can include one or more embedded camera sensors (within a display pixel). The display component can include one or more embedded camera sensors (within a display pixel) that include a transparent conducting material coated with quantum dots (photoconductors) or organic photodiodes. A readout integrated circuit (ROIC) that allows row-by-row readout may reduce any cross talk related issues. The display component embedded with camera sensors (a semitransparent camera) may enable eye tracking (in visible and SWIR wavelengths) and human-computer interface.

Details of the display component including one or more embedded camera sensors (within a display pixel) have been described/disclosed in FIGS. 42A and 42B of U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019.

Further details of the display component including one or more embedded camera sensors (within a display pixel) have been described/disclosed in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

Alternatively, an intelligent (smart) camera identifying an object in the intelligent (smart) camera's field of view can be utilized, where the intelligent (smart) camera can include an (embedded) digital signal processor (DSP), a tunable (short/long) focal length metasurface lens (e.g., utilizing (i) thermally tunable refractive index of a phase transition/phase change material or (ii) fabricated/constructed (utilizing electron beam lithography, DUV lithography or nanoimprint lithography) on a material (e.g., made of a dielectric and/or a semiconductor and/or a metal) patterned structures/meta atoms (e.g., 10 million vertical microscaled/nanoscaled pillars and/or microscaled/nanoscaled disks on or about 0.5 mm×0.5 mm area) with a maximum dimension generally less than 20,000 nm) in a two-dimensional arrangement to manipulate/control light and including a machine learning algorithm or an artificial neural network algorithm. However, meta atoms can be arranged in (i) a regular ordered periodic manner (e.g., a square lattice or a hexagonal lattice) or (ii) a quasi-periodic manner (e.g., like a pattern in a quasi-crystal).

The intelligent (smart) camera can overlay instructions (e.g., driving instructions) directly on the augmented reality (AR) images on a display component in real-time or near real-time, eliminating confusion caused by having to glance elsewhere.

Thus, the intelligent (smart) camera may be required to be coupled with a neuromorphic processor that can include memristors/super memristors. For example, such a neuromorphic processor (that can include memristors/super memristors) may be included in the intelligent appliance 880. Such memristors/super memristors can be electrically coupled/connected with processors/processor-specific electronic circuits in a two-dimensional arrangement or in a three-dimensional arrangement. For example, as illustrated in FIGS. 16A-16D and FIGS. 17A-17C of U.S. Non-Provisional patent application Ser. No. 17/803,388 entitled "SUPER SYSTEM ON CHIP", filed on Jun. 15, 2022.

Details of the neuromorphic processor (that can include memristors/super memristors) as a Super System On Chip have been described/disclosed in U.S. Non-Provisional patent application Ser. No. 17/803,388 entitled "SUPER SYSTEM ON CHIP", filed on Jun. 15, 2022 and in its related U.S. non-provisional patent applications (with all benefit provisional patent applications) are incorporated in its entirety herein with this application.

The intelligent (smart) camera can also include an algorithm to classify an image and another algorithm to translate language (in near real-time/real-time).

Alternatively, the camera sensor can be replaced/augmented by a computational camera sensor, wherein the computational camera sensor includes a laser and a photodiode (e.g., a PIN photodiode/avalanche photodiode/single photon avalanche detector).

Details of the computational camera sensor (e.g., FIGS. 3L-3Z) have been described/disclosed in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

Additionally, a (bio-inspired) neuromorphic event camera or a hyperspectral camera can be integrated with the intelligent subscriber subsystem 340 or with the intelligent appliance 880.

An event camera can be considered as a (bio-inspired) neuromorphic sensor that is distinctly different from a conventional fixed frame camera. Instead of capturing an image at a fixed frame rate, a (bio-inspired) neuromorphic event camera's optoelectronic synapse based light sensors (e.g., an array of detectors) asynchronously measure/detect per-pixel brightness changes and then provide an output as a stream of events that is encoded in time, location and brightness changes. A (bio-inspired) neuromorphic event camera offers attractive properties compared to a fixed frame traditional camera at least in high temporal resolution (in the order of microseconds), very high dynamic range (140 dB vs. 60 dB), low power consumption and high pixel bandwidth (on the order of kHz) resulting in reduced motion blur.

Thus, a (bio-inspired) neuromorphic event camera may have a significant potential for computer vision in challenging scenarios for traditional cameras, such as low-latency, high speed and high dynamic range.

For example, oxide Schottky junction (e.g., graphene/ITO electrodes on Nb (about 1 wt % Nb) doped single crystal $SrTiO_3$) based optoelectronic synapse based light sensors can enable a (bio-inspired) neuromorphic event camera via light field modulation and electric field modulation of the Schottky barrier at the graphene/ITO electrodes/Nb:$SrTiO_3$ interface.

Generally, a hyperspectral camera may require a digital micromirror (DMD), two relay lenses, diffraction gratings and a hyperspectral sensor (a hyperspectral sensor may include an array of photodetectors).

According to one embodiment, to fabricate/construct a large scale (compact) hyperspectral camera, an arrayed waveguide grating (AWG) or Echelle gratings based spectrophotometer integrated with (i) a vertical aperture with a 45-degree angle mirror for light coupling, (ii) an array of photodetectors, (iii) an array of preamplifiers with the array of photodetectors, if needed for gain and (iv) an array of readout circuits can be arranged in a two-dimensional arrangement with an array of lenses/metalenses.

It should be noted that a hyperspectral camera with a pre-selected spectral range can be considered as a multi-spectral camera. A multi-spectral camera is a subset of a hyperspectral camera.

General Optical Components & Imaging of a Hyperspectral Camera

Optical System: Lenses and mirrors that collect light from the scene and focus it onto the dispersive element. The spatial resolution of the captured images can depend on the quality of this optical system.

Dispersive Element: This is typically a prism or a diffraction grating that separates the incoming light into its constituent wavelengths. The dispersive element can play a crucial role in defining the camera's spectral resolution.

Detector Array: Hyperspectral cameras can contain an array of detectors to capture dispersed light. These detectors are sensitive to specific wavelength ranges and are arranged to allow simultaneous capture of multiple spectral bands. Common detector materials include Si (for visible light) and InGaAs or Ge on Si or mercury cadmium tellurium (MCT) or InSb (for infrared wavelengths). Furthermore, an array of detectors can have built-in deposited optical filters for compactness.

Data Acquisition System: This system converts the analog signals from the detector array into a digital format that can be processed by a computer. It typically includes analog-to-digital converters (ADCs) and high-speed data transfer interfaces.

Data Processing Unit: The raw data captured by the detector array is processed to create a hyperspectral data cube. This unit uses advanced algorithms to correct sensor noise, perform calibration, and extract meaningful information from the spectral data.

Light Collection & Dispersion: The optical system collects light from the scene and directs it towards the dispersive element. The dispersive element separates the light into its constituent wavelengths, spreading them across the detector array.

Image Capture: The detector array captures the dispersed light, with each detector element corresponding to a specific wavelength band. This enables simultaneous capture of multiple spectral bands for each pixel in the scene.

Data Cube Formation: The captured data can be organized into a three-dimensional hyperspectral data cube. The data cube has two spatial axes (x and y) corresponding to the scene and one spectral dimension (2) corresponding to the wavelength bands. Each voxel (volumetric pixel) in the data cube contains spectral information for a specific point in the scene.

Calibration & Correction: The raw hyperspectral data is corrected for sensor noise, distortions and environmental factors. This step often involves dark current subtraction, flat-field correction and wavelength calibration to ensure the accuracy and consistency of the spectral data.

Data Analysis & Interpretation: The processed hyperspectral data is analyzed to extract meaningful information.

This process can involve at least key steps. Spectral unmixing converts each pixel's spectral signature into its constituent components, allowing the identification of different materials in a mixed pixel. The pixel spectral signatures are then compared to a library of known spectral signatures to identify and classify materials. Principal component analysis can improve visualization and interpretation by reducing the dimensionality of the hyperspectral data and preserving the most significant spectral information.

Machine Learning Algorithms: Advanced machine learning techniques like support vector machines (and neural networks) can be used to automate and refine hyperspectral data analysis. These algorithms can identify intricate patterns within the spectral data, enhancing the accuracy and efficiency of material identification and classification processes.

Furthermore, a (bio-inspired) neuromorphic event camera or a hyperspectral camera can be coupled with a Super System on Chip or a System-on-a-Chip. A Super System on Chip can be either non-optically enabled or optically enabled. Furthermore, (i) a Super System on Chip (including optically enabled Super System on Chip) and/or (ii) a System-on-a-Chip can be integrated on a wafer scale.

Such a System-on-a-Chip can include one or more multipliers of matrices and/or graphic processors.

Furthermore, in another embodiment a System-on-a-Chip can include one or more central processors, wherein one central processor has one or more (i) processing cores and (ii) memory units, wherein at least one processing core and one memory unit can be coupled in an intertwined pattern in a two-dimensional arrangement or a three-dimensional arrangement, wherein one memory unit can include one or more memory elements, wherein one memory element can include one or more memory circuits.

Such a System-on-a-Chip can also include one or more multipliers of matrices and/or graphic processors.

A holographic display can generate light fields by dynamically modulating the wavefront of a coherent beam of light, utilizing a spatial light modulator (SLM). But its field of view is generally small and the small field of view may be expanded by diffractive optical elements (DOE) or a nanoscaled/nanopatterned metasurface of meta atoms in a two-dimensional arrangement.

However, meta atoms can be arranged in (i) a regular periodic manner (e.g., a square lattice or a hexagonal lattice) or (ii) a quasi-periodic manner (e.g., like a pattern in a quasi-crystal).

Furthermore, a three-dimensional/holographic-like display component can be fabricated/constructed utilizing a two-dimensional array of micropixels (of microLEDs) and an array of microlenses.

Furthermore, an embodiment of a quantum dot-metasurface/metasurface display that includes
  (a) a light source (e.g., (i) an organic light emitting diode or (ii) an organic light emitting diode including quantum dots, or a microLED or a nanoscaled light source) emitting a color in a visible wavelength,
  (b) a layer including one or more three-dimensional nanoscaled optical elements (wherein the above layer absorbs a portion of the color in the visible wavelength from the light source, wherein at least one three-dimensional nanoscaled optical element that includes a dielectric/metal or a tunable material, wherein the tunable material is a phase transition material or a phase change material, wherein at least one three-dimensional nanoscaled optical element has a maximum dimension less than 400 nm) and
  (c) an electrically switchable light valve or an electrically switchable light shutter have been described/disclosed in U.S. Non-Provisional patent application Ser. No. 17/803,388 entitled "SUPER SYSTEM ON CHIP", filed on Jun. 15, 2022 and in its related U.S. non-provisional patent applications (with all benefit provisional patent applications) are incorporated in its entirety herein with this application.

Generally, a phase transition material is a solid material, wherein its lattice structure can change from a particular solid crystalline form to another solid crystalline form, still remaining crystal-graphically solid. Generally, a phase change material is a material, wherein its phase can change from (i) a solid to liquid or (ii) an amorphous to crystalline or (iii) crystalline to amorphous.

Details of a holographic display component have been described/disclosed in FIG. 49 of U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019.

Further details of the holographic display component have been described/disclosed in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

Further details of the holographic display component have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016, (which resulted in a U.S. Pat. No. 9,923,124, issued on Mar. 20, 2018) and in its related U.S. non-provisional patent applications (with all benefit provisional patent applications) are incorporated in its entirety herein with this application.

Furthermore, a System-on-a-Chip, integrating one or more central processor modules and module specific software 760 with one or more graphic processor modules, internet firewall security system, spyware and the user-specific security control/authentication can simplify the construction and fabrication of the intelligent appliance 880.

It should be noted that the central processor modules and/or graphic processor modules can be stacked in a three-dimensional arrangement for scaling the performance. It should be noted that a three-dimensional arrangement can include a vertical arrangement.

Furthermore, a System-on-a-Chip can be replaced by or augmented/added (via co-integration and/or coupling) with a Super System on Chip for fast (or ultrafast) data processing, image processing/image recognition, deep learning/meta-learning and/or self-learning, wherein the Super System on Chip can include:
  (i) a processor-specific electronic integrated circuit, and/or
  (ii) an array or a network of memristors/super memristors for neural processing, and/or
  (iii) a photonic component or a photonic integrated circuit (PIC), wherein the photonic component comprises an optical waveguide,
  wherein the processor-specific electronic integrated circuit in said (i), the array or the network of memristors/super memristors in said (ii) and the photonic component or the photonic integrated circuit in said (iii) of the Super System on Chip can be interconnected or coupled in two-dimensions or in three-dimensions electrically and/or optically. It should be noted that atomically thin metal dichalcogenide/two-dimensional semiconductor material (e.g., $MoS_2$, $WS_2$ and $WSe_2$) with semimetallic bismuth as a contact layer can enable a high performance processor-specific electronic integrated circuit, extending Moore's law.

and/or (iv) (a) an input, or an output of the (optically enabled) Super System on Chip, and
wherein the input or the output of the (optically enabled) Super System on Chip is coupled with a light source (e.g., a laser) and a photodetector, (e.g., FIGS. 12-15),
wherein the input or the output of the (optically enabled) Super System on Chip is further coupled with a Mach-Zehnder interferometer,
wherein the Mach-Zehnder interferometer includes a phase transition material or a phase change material or a lithium niobate material or a polymeric material,
wherein the phase transition material is electrically and/or optically enabled, wherein the phase change material is electrically or optically enabled, wherein the lithium niobate material is electrically controlled,
wherein the Mach-Zehnder interferometer is coupled with a first optical waveguide (in either a two-dimensional or a three-dimensional arrangement, it should be noted that a three-dimensional arrangement can include a vertical arrangement),
wherein the first optical waveguide is coupled with (i) a semiconductor optical amplifier (SOA) or an optical resonator (in either the two-dimensional or the three-dimensional arrangement, it should be noted that a three-dimensional arrangement can include a vertical arrangement) and/or (ii) a second optical waveguide (in either a two-dimensional or a three-dimensional arrangement, it should be noted that a three-dimensional arrangement can include a vertical arrangement), wherein the second optical waveguide includes a nonlinear optical material,
(b) one or more third optical waveguides, coupled with the input or the output of the (optically enabled) Super System on Chip. It should be noted that a light source should consume low electrical power. Thus, a photonic crystal based in-plane edge emitting laser or a vertical cavity surface emitting laser (VCSEL) or a photonic crystal based vertical cavity surface emitting laser may be appropriate for low electrical power consumption. However, optical coupling a vertical cavity surface emitting laser into the (optically enabled) Super System on Chip may require a prism/mirror (placed in a silicon v-groove). It should be noted that all embodiments of the Super System on Chips (as generally described in this paragraph) can include (i) one or more graphic processors and/or (ii) a matrix multiplier to multiply (generally a series of) matrices. In this case, an image is split into small patches and each patch is turned into a row in a matrix. The filters or kernels used in the convolution are represented as columns in another matrix, with each column containing the weights of a kernel. The result is obtained by performing a matrix multiplication between these two matrices. All embodiments of the Super System on Chips are also artificial intelligence/machine learning accelerators, which are specialized hardware accelerators/computer systems (which may include one or more graphic processors) designed to accelerate artificial intelligence/machine learning, including artificial neural networks and machine vision. They are high-performance parallel computation machines specifically designed for the efficient processing of artificial intelligence/machine learning workloads like artificial neural networks. Furthermore, the graphic processors can be stacked in a three-dimensional arrangement for scaling the performance. It should be noted that a three-dimensional arrangement can include a vertical arrangement.

Details of the (optically enabled) Super System on Chip described in the previous sub-paragraph (iv) have been described/disclosed (e.g., FIGS. 28L-28N) in U.S. Non-Provisional patent application Ser. No. 17/803,388 entitled "SUPER SYSTEM ON CHIP", filed on Jun. 15, 2022 and in its related U.S. non-provisional patent applications (with all benefit provisional patent applications) are incorporated in its entirety herein with this application.

In general, all the embodiments (both non-optically enabled and optically enabled) of the Super System on Chips can enable a series of matrix multiplications. For example, an image is split into small patches and each patch is turned into a row in a matrix. The filters or kernels used in the convolution are represented as columns in another matrix, with each column containing the weights of a kernel. The result is obtained by performing a matrix multiplication between these two matrices.

In the case of the (optically enabled) Super System on Chip, a light signal is sent inside of the (optically enabled) Super System on Chip and it goes through a process that generally performs a matrix multiplication using the light signal.

In general, all the embodiments of the Super System on Chips can be designed for a specific task/calculation or can be reprogrammable to perform different tasks/calculations.

In general, all the embodiments of the Super System on Chips can enable back propagation of errors, which is analogous to calculating the delta rule for a multilayer feedforward network. Back propagation of errors involves repeatedly feeding training examples into the Super System on Chip and asking the Super System on Chip to make predictions about the data. Each time, the Super System on Chip measures how far off the prediction is and this error signal is then fed backward through the Super System on Chip.

This error signal can be used to adjust the strength of connections and/or weights within the Super System on Chip to improve the prediction performance of the Super System on Chip. This process can be repeated many times until the Super System on Chip can solve whatever task it has been assigned to.

But there may be a gap between a mathematical model of the back propagation of errors due to an intrinsic physical noise within the Super System on Chip (including optically enabled Super System on Chip) and/or inaccuracy of mathematical model in calculating the error signal.

However, an alternative training algorithm such as a direct feedback alignment (DFA) or an augmented direct feedback alignment may be more appropriate than the back propagation of errors.

Details of the Super System on Chip have been described/disclosed (e.g., FIGS. 15C-28B) in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

Further details of the Super System on Chip have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016, (which resulted in a U.S. Pat. No. 9,923,124, issued on Mar. 20, 2018) and in its related U.S. non-provisional patent applications (with all benefit provisional patent applications) are incorporated in its entirety herein with this application.

If the Super System on Chip (including optically enabled Super System on Chip) and/or the System-on-a-Chip can be coupled with a voice processing module-enabling a neural network/machine learning based voice processing module (a Super Voice Processing Module—that can also include semantic analyzer. Powered by machine learning algorithms and natural language processing, semantic analyzer can understand the context of natural language and/or detect emotion/sarcasm and extract valuable information from unstructured data, achieving human-level accuracy). The Super Voice Processing Module can be used for audio events identification, command detection, keyword spotting, speaker identification and wake word detection. It can also support spoken words and can be programmed to recognize sounds. The Super Voice Processing Module can also enable enhanced surround sound.

Efficient computing and processing by the Super System on Chip and/or System-on-a-Chip may require an effective thermal management. Furthermore, the Super System on Chip and/or System-on-a-Chip may be thermally coupled with a cooler (e.g., an active (mini) cooler or a passive cooler) for thermal management.

An active (mini) cooler is an actively controlled cooler with a miniature (e.g., about 25 mm×25 mm in surface area and 12 mm thick) form factor. A passive cooler is not actively controlled and it can be larger in size compared to the size of the active (mini) cooler.

For example, as discussed in the later paragraphs, an active (mini) cooler can include an array of negative voltage biased tips (e.g., tips fabricated/constructed from boron nanotube/carbon nanotube/amorphous diamond/tungsten), which is placed just below a hole (e.g., about 100 microns in diameter) of positive voltage biased surface (e.g., tungsten/two-dimensional crystal material (e.g., graphene)).

Electrons emitted from the negative voltage biased array of tips can escape through the hole and ionize the gas molecules within the boundaries of a heat sink (e.g., the heat sink can be fabricated/constructed from a materials such as aluminum/silicon/copper/carbon nanotube-copper composite or a two-dimensional crystal material (e.g., graphene) or diamond). By switching the voltage polarity of the heat sink, a moving ionized gas cloud can disperse the heat from the Super System on Chip and/or System-on-a-Chip.

However, it is desirable that an array of tips emit electrons at a much lower voltage (e.g., 10 volts). An array of nanoscaled tungsten tips can be fabricated/constructed on tungsten substrate. The nanoscaled tungsten tips can be surrounded by an insulator. The nanoscaled tungsten tip can be decorated with a monolayer of a suitable material (e.g., diamond deposited by low temperature electron cyclotron resonance-chemical vapor deposition (ECR-CVD) or gold deposited by RF magnetron sputtering) of proper bandgap/electronic structure to enable electrons to emit at a much lower voltage (e.g., at 10 volts) and escape through the hole.

Details of the above active (mini) cooler for heat dissipation/thermal management have been described/disclosed (e.g., FIGS. 20A-20C) in U.S. Non-Provisional patent application Ser. No. 17/803,756 entitled "SYSTEM & METHOD FOR MACHINE LEARNING BASED AND AUGMENTED REALITY BASED USER APPLICATION", filed on Nov. 14, 2022 and in its related U.S. non-provisional patent applications (with all benefit provisional patent applications) are incorporated in its entirety herein with this application.

Alternatively, an active (mini) cooler may include a micro-electrical-mechanical-system based cooler for heat dissipation/thermal management.

Alternatively, a passive cooler may include microchannels and/or microjets for heat dissipation/thermal management, wherein the microchannels and/or microjets can be thermally coupled with a heatsink. Alternatively, a passive cooler may include monolithically integrated (on-chip) microchannels for heat dissipation/thermal management.

Details of the microchannels and/or microjets based cooler for heat dissipation/thermal management have been described/disclosed in U.S. Non-Provisional patent application Ser. No. 17/803,388 entitled "SUPER SYSTEM ON CHIP", filed on Jun. 15, 2022 and in its related U.S. non-provisional patent applications (with all benefit provisional patent applications) are incorporated in its entirety herein with this application.

Alternatively, high-efficiency nanostructured $50A^0$ thick $Sb_2Te_3/10A^0$ thick $Bi_2Te_3$-based thin-film superlattices thermoelectric cooler (TEC)/microrefrigerator (1 mm×3 mm) can also be utilized to cool a hot spot (or hot spots) within the Super System on Chip and/or System-on-a-Chip. However, significant thermoelectric cooler (TEC)/microrefrigerator efficiency can be gained by fabricating a quantum wire/quantum dot, transitioning from a two-dimensional superlattice.

Furthermore, to enable surround sound, one or more piezoelectric speakers (based on piezoelectric transducers), a low noise, high voltage amplifier and a digital signal processor can be integrated behind a display component 860.

Alternatively, mechanical touch pressures on piezoelectric transducers can enable a new immersive touch screen and haptic feedback interface.

Furthermore, the voice processing module can be coupled with computer implementable instructions (which can be stored either (i) locally with the Super System on Chip (including optically enabled Super System on Chip) and/or the System-on-a-Chip or (ii) in a remote/cloud server (which can be accessed by the Super System on Chip and/or the System-on-a-Chip over the internet from the remote/cloud server) to understand and process an audio signal in natural language.

For example, by eavesdropping on the user's communication, the Super System on Chip (including optically enabled Super System on Chip) and/or the System-on-a-Chip can anticipate the user's need for emergency healthcare and then recommend the fastest route to the emergency section of a nearby hospital by synthesizing data (anonymously searching the internet) regarding traffic, road and weather condition. If another healthcare facility is cheaper with a special/faster offer, the Super System on Chip (including optically enabled Super System on Chip) and/or the System-on-a-Chip can alert the user and it can automatically contact the user's family in this emergency, without any input from the user.

Thus, the Super System on Chip (including optically enabled Super System on Chip) and/or the System-on-a-Chip can be self-learning and sensor-aware and/or context aware.

Sensor-aware enables coupling with sensors, visualizing and exploring spatial-temporal data from static and mobile sensors. Sensor-aware also provides cross-filtering and details-on-demand interactions, which can allow a user to investigate data at different levels of details from spatial-temporal data.

For example, in sensor-aware computing, a user may receive sensor data in real-time or near real-time from a remotely located real property.

Context-aware is a type of computing in which situational and environmental information about a user is used to anticipate immediate needs and proactively offer enriched, situation-aware and usable content, functions and experiences. In context-ware computing, a user's activities and locations can be important.

For example, in context-aware computing, a user may not receive any communication, while the user is driving a vehicle. For example, context awareness may eliminate unwanted interruptions or actively notify a user of an incoming call by adjusting the ringer and vibrate settings. It may have the ability to relay the user's contextual information to the caller when the user can be generally unavailable based on the intelligence learned from the user's call history.

For example, the Super System on Chip (including optically enabled Super System on Chip) and/or the System-on-a-Chip can be self-learning and communicatively interfaced with one or more computer implementable instructions (software) such as:
  (i) a first set of computer implementable instructions to process the audio signal (the audio signal can be a voice signal or the audio signal includes a voice signal),
  (ii) a second set of computer implementable instructions to analyze and/or interpret contextual data (which can include a social graph and health data of a user), depending on the context of information,
  (iii) a third set of computer implementable instructions in self-learning, wherein the third set of computer implementable instructions includes (i) machine learning or (ii) artificial neural network algorithm (which may include a collection of declarative knowledge based computer implementable instructions to enable common sense),
  (iv) a fourth set of computer implementable instructions in self-learning that is at least based on a text, an image, a video and an experience/gained experience. Furthermore, this fourth set of computer implementable instructions can also include computer vision or Vision Transformer (ViT). (a Vision Transformer is a model for image classification that utilizes a transformer like architecture over patches of an image. An image is split into fixed-size patches, each of patches is then linearly embedded, position embeddings are also added—the resulting sequence of vectors is fed into a standard Transformer encoder. It may require higher computing power and may be useful for processing data, (natural) language, a raw image and a video). Such a fourth set of computer implementable instructions can enable a self-learning chatbot, wherein the self-learning chatbot can be coupled with natural language processing (and/or a collection of declarative knowledge to enable common sense).

It should be noted that to enable the intelligent subscriber subsystem 340 or the intelligent appliance 880 self-learning (which can learn by itself), at least in part, the above second set of computer implementable instructions and/or the above third set of computer implementable instructions and/or the above fourth set of computer implementable instructions may be required.

Such computer implementable instructions (software) can be stored either (i) locally with the Super System on Chip (including optically enabled Super System on Chip) and/or the System-on-a-Chip or (ii) in a remote/cloud server (which can be accessed by the Super System on Chip and/or the System-on-a-Chip over the internet from the remote/cloud server).

Details of the intelligent algorithm have been described/disclosed in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

However, a machine learning algorithm or an artificial neural network algorithm/deep learning algorithm (stored locally or in a remote/cloud server) may include a generative artificial intelligence/physics-inspired generative artificial intelligence model.

It should be noted that a neural network may be considered as a multi-layer perception, wherein each synapse learns a number named a weight and each neuron applies a mathematical function to a sum of its inputs. But in Kolmogorov-Arnold based neural network architecture (KANN) each synapse learns a function and the neurons sum the outputs of these functions. Kolmogorov-Arnold based neural network architecture places learnable activation functions along the edges and the nodes sum it up, as opposed to fixed activation functions on the nodes in a traditional neural network/multi-layer perception.

But they are generally based on a transformer model or a diffusion model (e.g., Poisson flow generative model++ (PFGM++)) and can be broadly classified as an artificial neural network algorithm/deep learning algorithm-which may be augmented with an evolutionary based algorithm and/or a game theory based algorithm and/or Poisson flow generative model++.

Non-equilibrium statistical physics inspired iterative a forward diffusion process can slowly destroy structure in a data distribution. Similarly, a reverse diffusion process can restore structure in data, yielding a highly flexible and tractable generative model.

A game theory based algorithm may enable consensual interactions within a transformer model or a diffusion model for accuracy and reproducibility of output data.

Poisson flow generative model++ can couple a diffusion model with Poisson's equation. Poisson flow generative model++ relies on physics-inspired formulations (e.g., based on the laws of electromagnetism/weak nuclear force/strong nuclear force/gravitational force or Coulomb's law). Poisson flow generative model++ may enable smaller training data sets than diffusion models, less error-prone and requiring fewer computational steps.

However, utilizing smaller/compact versions of the above algorithms/models may enable a (personal) artificial intelligence based self-learning assistant on the intelligent subscriber subsystem 340 or on the intelligent appliance 880 itself and enable to preserve data privacy and personalize for a user at a reduced computing resource.

But fully expanded versions of the above algorithms/models may require extensive computing resources in a cloud and the inputs/outputs of the computing resources in a cloud can be communicatively interfaced with the intelligent subscriber subsystem 340 or the intelligent appliance 880.

An evolutionary based algorithm is a heuristic-based approach to solving problems that cannot be easily solved in polynomial time and it is a kind of Monte-Carlo method. An evolutionary based algorithm generally utilizes mechanisms inspired by biological evolution (e.g., reproduction, mutation, recombination and selection).

Generally, game theory can be classified into two categories: (a) non-cooperative game, where a decision-making unit treats the other participants as competitors and (b) a cooperative game, where a group of decision-making units decide to undertake a decision together to achieve their shared objectives.

In game theory, individuals/groups/units become players, when their respective decisions coupled with the decisions made by other players, produce an outcome/output. The options available to players to bring about particular outcomes are called as strategies, which are linked to outcomes/outputs by a mathematical function that specifies the consequences of the various combinations of strategy choices by all players in a game.

A coalition refers to the formation of sub-sets of players' options under coordinated strategies. In game theory, the core is the set of feasible allocations that cannot be improved upon by a coalition. An imputation $X=\{x_1, x_2 \ldots x_n\}$ is in the core of an n-person game if and only if for each subset, S of N:

$$\sum_{i=1}^{n} x_i \geq V(S)$$

where V(s) is the characteristic function V of the subset S indicating the amount (reward) that the members of S can be sure of receiving, if they act together and form a coalition (or the amount of S can get without any help from players who are not in S). Above equation states that an imputation x is the core (that X is undominated), if and only if for every coalition S, the total of the received by the players in S (according to X) is at least as large a V(S). The core (C) can also be defined by the equation below as the set of stable imputations:

$$C: \left\{ x = (x_1, \ldots, x_n) : \sum_{i \in N} x_i = V(N) \text{ and } \sum_{i \in S} x_i \geq V(S), \forall S \subset N \right\}$$

The imputation x is unstable through a coalition S, if the equation below is true, otherwise is stable.

$$V(S) > \sum_{i \in s} x_i$$

The core (C) can consist of many points. The size of the core can be taken as a measure of stability or how likely a negotiated agreement is prone to be upset. To determine the maximum penalty (cost) that a coalition in the network can be sure of receiving, the linear programming problem represented by the equation below can be used, when maximize $x_1+x_2+x_3+ \ldots +x_n$ $$\sum_{i \in C} x_i \leq V(C) \forall\, C \subset N \text{ subject to } (x_1, x_2, \ldots, x_n) \geq 0$$

Thus, as outlined above, a game theory based algorithm can account for any conflict and produce accurate and reproducible output data Generally, all transformers have the same primary components: (i) Tokenizers, which convert text into tokens, (ii) A single embedding layer-converting tokens and positions of such tokens into vector representations, (iii) Transformer layers carrying out repeated transformations on the above vector representations-extracting linguistic information. These can consist of alternating attention and feedforward layers, (Optionally) (iv) Un-embedding layer that can convert the final vector representations back into a probability distribution over the tokens. Transformer layers can be encoder type or decoder-type or in some cases even both. Transformers typically undergo self-supervised learning involving unsupervised pretraining followed by supervised fine-tuning.

A special type of transformer-a Vision Transformer (ViT) and an evolutionary based algorithm have been disclosed in (a) U.S. Non-Provisional patent application Ser. No. 17/803, 388 entitled "SUPER SYSTEM ON CHIP", filed on Jun. 15, 2022.

Furthermore, a Vision Transformer can be communicatively interfaced with an algorithm to convert an image to a three-dimensional image to a text, then to an audio signal (e.g., voice), which can be stored on a remote/cloud server or even locally on the intelligent subscriber subsystem 340 itself or on the intelligent appliance 880 itself, if the electrical power consumption is not a problem.

Additionally, an algorithm to convert an image to a three-dimensional image to a text, then to an audio signal can be communicatively interfaced with a computational camera and thus may enable a pedestrian to see around the corner, before crossing a road. However, to image around the corner, a computational camera may require a high output power pulsed laser and a two-dimensional array of single photon avalanche detectors. Furthermore, utilizing (i) a machine learning algorithm or (ii) an artificial neural network algorithm/deep learning algorithm coupled with a transformer model or a diffusion model, a text can be converted to a video. Additionally, utilizing Poisson flow generative model++ may enable superior image reconstruction.

Various embodiments of the intelligent subscriber subsystem 340 can be integrated with the intelligent appliance 880. Similarly, various embodiments of the intelligent appliance 880 can be integrated with the intelligent subscriber subsystem 340.

The Super System on Chip (including optically enabled Super System on Chip) and/or System-on-a-chip can be coupled with a first artificial eye or a second artificial eye. The first artificial eye can include light activated and/or electrically activated switches. The second artificial eye can include an array of photodiodes/optical capacitors.

For example, the artificial eye can be fabricated/constructed utilizing a very large scale integration of the atomic scaled switches. Photocurrent is induced in a photoconductive layer (which is coupled between a metal electrode and a solid-electrolyte electrode) by light irradiation. The photocurrent reduces metal ions with positive charges in the solid-electrolyte electrode and this precipitates as metal atoms to form an atomic scaled metal connection between the metal electrode and the solid-electrolyte electrode-operating as an atomic scaled switch, turned on by light irradiation and/or an applied electrical activation (e.g., voltage).

Instead of a photoconducting layer, an array of (fast light) responsive photodiodes (e.g., made of graphene or tungsten diselenide or a suitable (fast light) responsive two-dimensional material) or an array of optical capacitors (e.g., made of p+ silicon substrate/silicon dioxide/a perovskite material with a large photoconductive response/semi-transparent metal electrode, wherein light is incident through the semi-transparent metal electrode) can be utilized also. The optical capacitor can respond dynamically to light intensities.

It should be noted that an array of (fast light) responsive photodiodes coupled with phase transition/phase change material (electrically/optically controlled) based switches can enable a fast responsive artificial eye.

Generally, a phase transition material is a solid material, wherein its lattice structure can change from a particular solid crystalline form to another solid crystalline form, still remaining crystal-graphically solid. Generally, a phase change material is a material, wherein its phase can change from (i) a solid to liquid or (ii) an amorphous to crystalline structure or (iii) crystalline structure to amorphous. The first artificial eye or the second artificial eye can be coupled with a neural processor/Super System on Chip (including optically enabled Super System on Chip).

Details of the artificial eye have been described/disclosed in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

Furthermore, the Super System on Chip (including optically enabled Super System on Chip) can be coupled with a neuromorphic visual system. A neuromorphic visual system including optical resistive random access memory (ORRAM) based synaptic devices in a two-dimensional array can emulate/approximate basic functions of the human visual system beyond visible light.

For example, an optical resistive random access memory (ORRAM) based synaptic device can include an (i) optically (laser beam) coupled capacitor of an oxide semiconductor material (e.g., amorphous indium-gallium-zinc oxide or molybdenum oxide) or (ii) optically (laser beam) coupled field effect transistor of a two-dimensional material (e.g., molybdenum disulfide ($MoS_2$) or graphene) or a hetrostructure of two distinct two-dimensional materials. An optically (laser beam) coupled capacitor of an oxide semiconductor material can be a sandwich structure of a top transparent electrode (e.g., indium tin oxide)/middle oxide semiconductor material (e.g., amorphous indium-gallium-zinc oxide or molybdenum oxide)/a bottom non-transparent electrode on a substrate.

Optical (laser beam) coupling can be realized from a laser beam (propagated via an optical waveguide) diffracted by gratings etched onto an optical waveguide of an optical switch (e.g., a Mach-Zehnder interferometer type optical switch).

The optical switch (laser beam switching) can include a phase change material or a phase transition material and it can be activated by a distinct pump optical signal of another wavelength or an electrical signal (e.g., voltage or current).

To increase the intensity of a laser beam, the oxide semiconductor material can be fabricated/constructed nanoscaled in size and placed near a plasmonic nanoantenna.

Similarly, to increase the intensity of laser beam, a source metal and a drain metal of the field effect transistor of a two-dimensional material/hetrostructure of two distinct two-dimensional materials can be fabricated/constructed to form a plasmonic nanoantenna.

Details of a plasmonic nanoantenna have been described/disclosed in FIGS. 12H-12O of U.S. Non-Provisional patent application Ser. No. 16/602,966 entitled "OPTICAL BIO-MODULE TO DETECT DISEASES AT AN EARLY ONSET", filed on Jan. 6, 2020 and in its related U.S. non-provisional patent applications (with all benefit provisional patent applications) are incorporated in its entirety herein with this application.

Thus, a neuromorphic visual system can include (i) an optically (laser beam) coupled capacitor/field effect transistor, (ii) an optical switch and (iii) a plasmonic nanoantenna.

Applications of the Super System on Chip (including optically enabled Super System on Chip) are listed below:

Artificial Intelligence (AI): The Super System on Chip (including optically enabled Super System on Chip) may be suited for artificial intelligence applications because they can mimic the way that neurons in the human brain store and process information and they could be faster and more energy efficient.

Machine Learning (ML): The Super System on Chip may also be used to accelerate machine learning algorithms. Machine learning algorithms are used to train AI models to perform specific tasks, such as image recognition or natural language processing and they could make it possible to train artificial intelligence models more quickly and efficiently.

Edge Computing: The Super System on Chip may also be used to develop edge computing devices. Edge computing is a distributed computing paradigm that brings computation and data storage closer to the devices, where the data is generated. This may reduce latency and improve performance for applications such as real-time video processing and sensor fusion. Other Applications: The Super System on Chip may be used to develop new types of memory devices, logic circuits and analog circuits.

Internet of Things (IoT) Device: The Super System on Chip may be used develop Internet of Things devices that are more energy-efficient and can process data more quickly.

Medical Device: The Super System on Chip may be used to develop medical devices that can monitor patients' health in near real-time and provide personalized care.

Self-Driving Car: The Super System on Chip may be used to develop self-driving cars that can make faster and more accurate decisions in near real-time.

Furthermore, the Super System on Chip (including optically enabled Super System on Chip) can be coupled with a radio (wireless) transceiver integrated circuit (e.g., 5G/higher than 5G bandwidth radio (wireless) transceiver integrated circuit).

The Super System on Chip (including optically enabled Super System on Chip) and/or System-on-a-chip can be coupled with an intelligent algorithm, which includes a digital security protection (DSP) algorithm submodule, a natural language processing algorithm submodule and an application specific algorithm submodule (the application specific algorithm submodule is coupled with a public/consortium/private blockchain). The application specific algorithm submodule and a knowledge database (the knowledge database is coupled with a public/consortium/private blockchain) are coupled with a computer vision algorithm submodule, a pattern recognition algorithm submodule, a data mining algorithm submodule, Big Data analysis algorithm submodule, a statistical analysis algorithm submodule, a fuzzy logic (including neuro-fuzzy) algorithm submodule an artificial neural network/artificial intelligence algorithm submodule, a machine learning (including deep learning/meta-learning and self-learning) algorithm submodule, a predictive analysis algorithm submodule, a prescriptive algorithm module and a software agent algorithm submodule.

The fusion of a neural network algorithm and fuzzy logic algorithm is neuro-fuzzy, which can enable both learning as well as approximation of uncertainties. The neuro-fuzzy algorithm can use fuzzy inference engine (with fuzzy rules) for modeling uncertainties, which is further enhanced through learning the various situations with a radial basis function. The radial basis function consists of an input layer, a hidden layer and an output layer with an activation function of hidden units. A normalized radial basis function with unequal widths and equal heights can be written as:

$$\psi_i(x)(\text{softmax}) = \frac{\exp(h_i)}{\sum_{i=1}^{n} \exp(h_i)}$$

$$h_i = \left(-\sum_{i=1}^{2} \frac{(X_i - u_{il})^2}{2\sigma_i^2}\right)$$

X is the input vector, uil is the center of the ith hidden node (i=1, ..., 12) that is associated with the lth (l=1,2) input vector, σi is a common width of the ith hidden node in the layer and softmax (hi) is the output vector of the ith hidden node. The radial basis activation function is the softmax activation function. First, the input data is used to determine the centers and the widths of the basis functions for each hidden node. Second, it is a procedure to find the output layer weights that minimizes a quadratic error between predicted values and target values. Mean square error can be defined as:

$$MSE = \frac{1}{N}\sum_{k=1}^{N}\left((TE)_k^{exp} - (TE)_k^{cal}\right)^2$$

The connections between various algorithm submodules of the intelligent algorithm can be like synaptic networks to enable deep learning/meta-learning and self-learning of the intelligent algorithm. Meta-learning can enable a machine to have some human-level mental agility. It may be useful for achieving machine intelligence at human-level.

Details of the intelligent algorithm have been described/disclosed in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

Furthermore, a set of computer implementable instructions in intelligent algorithm(s) including self-learning may include the following:
 (i) a first set of computer implementable instructions to augment a digital data onto an image/video,
 (ii) a second set of computer implementable instructions to output a social graph of the user, wherein the social graph comprises appointment calendar, chat log and e-mail of the user,
 (iii) a third set of computer implementable instructions to analyze and/or interpret contextual data (or even health data) of the user.
 (iv) a fourth set of computer implementable instructions in self-learning that is at least based on a text, an image, a video and an experience/gained experience.

Furthermore, this fourth set of computer implementable instructions can also include computer vision or Vision Transformer. (a Vision Transformer is a model for image classification that utilizes a transformer like architecture over patches of an image. An image is split into fixed-size patches, each of patches is then linearly embedded, position embeddings are also added—the resulting sequence of vectors is fed into a standard Transformer encoder. It may require higher computing power and may be useful for processing data, (natural) language, raw images and video).

Such a fourth set of computer implementable instructions can enable a self-learning chatbot, wherein the self-learning chatbot can be coupled with natural language processing and/or a collection of declarative knowledge (as discussed in the previous paragraphs).

It should be noted that contextual data may include a social graph of the user.

Details of the social graph have been described/disclosed in U.S. Non-Provisional patent application Ser. No. 17/803,388 entitled "SUPER SYSTEM ON CHIP", filed on Jun. 15, 2022 and in its related U.S. non-provisional patent applications (with all benefit provisional patent applications) are incorporated in its entirety herein with this application.

To collect contextual data (which can even include health data) of the user, a sensor or biosensor/biological lab-on-a-chip (LOC) (coupled/interfaced with the Super System on Chip (including optically enabled Super System on Chip) and/or the System-on-a-Chip on a printed circuit board or multi-chip module level) may be used.

Furthermore, it may be necessary to collect both in-vivo and in-vitro health data user utilizing both a sensor or biosensor/biological lab-on-a-chip (LOC) and a bioobject (a bioobject can be implanted inside a human body or transiting through a human body via heartbeat assisted movements).

Generally, a bioobject can be enclosed within a protective biocompatible sealed package, which can include a tiny processor/microcontroller (e.g., ARM Cortex™-M4 ST Microelectronics STM32L4), a tiny memory (e.g., 8-Mbit Infineon ferroelectric random access memory CY15B108QI) and a tiny radio module/radio transceiver (e.g., Microchip Technology/Microsemi ZL70323MNJ). In transiting through a human body, it may also include a tiny transmitting light source (e.g., a microscaled light emitting diode (microLED)), a tiny light detection sensor in a suitable wavelength range (e.g., a complementary metal oxide semiconductor (CMOS) sensor or a single photon avalanche diode (SPAD) for low light detection or an array of single photon avalanche diodes for low light detection), a flat metamaterial (metasurface) lens, a bandapss thin-film optical filter (which may be integrated onto the above light sensor to filter out the transmitting light) and an accelerometer (e.g., Analog Devices ADXL363).

Such a bioobject (about 25 mm long and 15 mm in diameter) implanted inside a human body or transiting through a human body (e.g., FIGS. 12A, 12B, 12C and 13)

has been described/disclosed in U.S. Non-Provisional patent application Ser. No. 17/803,388 entitled "SUPER SYSTEM ON CHIP", filed on Jun. 15, 2022 and in its related U.S. non-provisional patent applications (with all benefit provisional patent applications) are incorporated in its entirety herein with this application.

For example, if an elderly user living alone in a home, suddenly experiences a heart attack, a biosensor/biological lab-on-a-chip on the elderly user can detect such health problem and call 911 emergency automatically with the location GPS coordinates of the elderly user, without any intervention of the elderly user.

Such computer implementable instructions (software) can be stored either (i) locally with the Super System on Chip (including optically enabled Super System on Chip) and/or the System-on-a-Chip or (ii) in a remote/cloud server (which can be accessed by the Super System on Chip and/or the System-on-a-Chip over the internet from the remote/cloud server), if electrical power consumption is not an issue.

The third set of computer implementable instructions can also understand/interpret an audio signal/voice (e.g., voice signal in natural language), a text and an image input and then provide specific suggestions to the user, based on context.

Thus, the third set of computer implementable instructions (as discussed earlier) can interpret or analyze contextual data, depending on the context of information. Generally, the third set of computer implementable instructions may include (i) a machine learning algorithm or (ii) an artificial neural network algorithm/deep learning algorithm. However, a machine learning algorithm or an artificial neural network algorithm/deep learning algorithm may include a generative artificial intelligence/physics-inspired generative artificial intelligence model. But they are generally based on a transformer model or a diffusion model and can be broadly classified as an artificial neural network algorithm/deep learning algorithm—which may be augmented with an evolutionary based algorithm and/or a game theory based algorithm. Thus, they may enable a (personal) artificial intelligence based self-learning assistant.

Further details of the intelligent algorithm(s) have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016, (which resulted in a U.S. Pat. No. 9,923,124, issued on Mar. 20, 2018) and in its related U.S. non-provisional patent applications (with all benefit provisional patent applications) are incorporated in its entirety herein with this application.

Furthermore, a super-capacitor (e.g., manufactured by www.cap-xx.com) and/or proton exchange membrane micro fuel-cell can enhance the operational time of a battery/solar cell/micro fuel-cell/wired power supply component.

A foldable/stretchable display component can be constructed from a graphene sheet and/or an organic light-emitting diode connecting/coupling/interacting with a printed organic transistor and a rubbery conductor (e.g., a mixture of carbon nanotube/gold conductor and rubbery polymer) with a touch/multi-touch sensor. The foldable/stretchable display component can be rollable or reconfigurable/morphable in size.

Details of a foldable/stretchable/rollable display component have been described/disclosed in FIG. 14B of U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016.

Further details of the foldable/stretchable/rollable display component have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016, (which resulted in a U.S. Pat. No. 9,923,124, issued on Mar. 20, 2018) and in its related U.S. non-provisional patent applications (with all benefit provisional patent applications) are incorporated in its entirety herein with this application.

Details of a display component reconfigurable/morphable in size have been described/disclosed in FIGS. 18A-18B of U.S. Non-Provisional patent application Ser. No. 16/602,966 entitled "OPTICAL MODULE TO DETECT DISEASES AT AN EARLY ONSET", filed on Jan. 6, 2020.

Further details of the display component reconfigurable/morphable in size have been described/disclosed in U.S. Non-Provisional patent application Ser. No. 16/602,966 entitled "OPTICAL BIOMODULE TO DETECT DISEASES AT AN EARLY ONSET", filed on Jan. 6, 2020 and in its related U.S. non-provisional patent applications (with all benefit provisional patent applications) are incorporated in its entirety herein with this application.

The intelligent appliance 880 includes a voice-to-text-to-voice processing module and module specific software. (e.g., Crisp Sound is real-time audio signal processing software for echo cancellation, background noise reduction, speech enhancement and equalization), a video compression module and module specific software, a photo-editing software module and a software module for automatically uploading content to a remote/cloud server.

The intelligent appliance 880 can be much thinner than 20 mm, if both the display and battery components are thinner.

A thinner photonic crystal display component can be fabricated/constructed as follows: optically pumping different-sized photonic crystals, whereas the photonic crystals can individually emit blue, green and red light based on their inherent sizes. Optical pumping can be generated from optical emission by electrical activation of semiconductor quantum-wells. Blue, green and red light can be then multiplexed/combined to generate white light.

Further details of the photonic crystal display component have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016, (which resulted in a U.S. Pat. No. 9,923,124, issued on Mar. 20, 2018) and in its related U.S. non-provisional patent applications (with all benefit provisional patent applications) are incorporated in its entirety herein with this application.

A thinner organic battery component can be fabricated/constructed as follows: an organic battery utilizes push-pull organic molecules, wherein after an electron transfer process, two positively charged molecules are formed which are repelled by each other like magnets. By installing a molecular switch, an electron transfer process can proceed in the opposite direction. Thus, forward and backward switching of an electron flow can form the basis of an ultra-thin, light weight and power efficient organic battery, based on electrical charge storage in organic molecules.

The intelligent appliance 880 can be integrated with a miniature surround sound (e.g., a micro-electrical-mechanical-system based silicon microphone component-Analog ADMP 401 or an equivalent component from www.akustica.com) module and module specific software, a miniature power efficient projection (e.g., a holographic/micromirror projector) module and module specific software, an infrared transceiver module and module specific software and a biometric sensor (e.g., a fingerprint/retinal scan) module and module specific software.

A projection module can be miniaturized by utilizing one tilt-able 1 mm diameter single crystal mirror. The mirror deflects a laser (blue, green and red) beam by rapidly switching its angle of orientation, building up a picture pixel by pixel.

An array of (at least four) front-facing cameras can provide stereo views and motion parallax (apparent difference in a direction of movement produced relative to its environment). Each camera can create a low dynamic range depth map. However, an array of cameras can create a high dynamic range depth map; thus, the intelligent appliance 880 can enable three-dimensional video conferencing.

The intelligent appliance 880 has multiple radio modules with multiple antennas. These multiple radio modules with multiple antennas can be simplified by a software-defined radio. Augmented reality allows computer-generated content to be superimposed over a live camera-view in the real world. The intelligent appliance 880 can be integrated with augmented reality to enrich the user's experience and need.

The intelligent appliance 880 can be coupled with an augmented reality apparatus/augmented reality personal assistant apparatus.

Details of an augmented reality apparatus have been described/disclosed in FIGS. 51A, 51B, 51C, 51D, 52A, 52B, 52C, 52D and 53 in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019.

Further details of the augmented reality apparatus have been described/disclosed in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

The augmented reality personal assistant apparatus can include a camera sensor (wherein the camera sensor can provide a two-dimensional/three-dimensional image/video, wherein the camera sensor can be electro-optically coupled with one or more microlenses to image surrounding areas) and a display component (or a holographic display component).

Furthermore, a camera sensor can include a tunable focal length liquid lens. A sealed transparent (to an optical/viewing axis) optical cell can contain two immiscible (e.g., water and oil) liquids, having equal physical (not optical) densities. A pair of piezoelectric sensors/motors can be mechanically coupled (perpendicular to the optical/viewing axis) with the sealed transparent (optical cell). By applying voltage inputs to each piezoelectric sensor/motor, mechanically coupled with the sealed transparent (optical cell), the geometrical shape of one of the immiscible liquids can be changed rapidly-making a variable/tunable focal length (liquid) lens. Instead of a pair of piezoelectric sensors/motors, a pair of vanadium dioxide based piezoelectric sensors/motors can be used. Vanadium dioxide is an insulator at a room temperature, but abruptly becomes an electrical (but, not thermal) conductor at about 67° C. This temperature driven phase transition from insulator-to-metal (IMT) occurs in a time scale of milliseconds (even nanoseconds). Furthermore, vanadium dioxide (lattice) crystal also undergoes a temperature driven structural phase transition, whereby when heated the crystal rapidly contracts along one axis, while expanding along the other two axes. Thus, vanadium dioxide can enable a miniaturized piezoelectric sensor/motor. The heating of the vanadium dioxide to actuate as a miniaturized piezoelectric sensor/motor can be done with a heating pad. Furthermore, as vanadium dioxide absorbs light, it converts into heat, thus the actuation can be triggered opto-thermally.

Alternatively, the camera sensor can be replaced/augmented by a computational camera sensor, wherein the computational camera sensor includes a laser and a photodiode (e.g., a PIN photodiode/avalanche photodiode/single photon avalanche detector).

Details of the computational camera sensor (e.g., FIGS. 3L-3Z) have been described/disclosed in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

The augmented reality personal assistant apparatus can also include a voice processing module (generally, a module such as a voice processing module can consist of one or more electronic components) to process a voice command or an audio signal.

Details of an augmented reality personal assistant apparatus have been described/disclosed in FIGS. 17A-17C of U.S. Non-Provisional patent application Ser. No. 16/602,966 entitled "OPTICAL BIOMODULE TO DETECT DISEASES AT AN EARLY ONSET", filed on Jan. 6, 2020.

Further details of the augmented reality personal assistant apparatus have been described/disclosed in U.S. Non-Provisional patent application Ser. No. 16/602,966 entitled "OPTICAL BIOMODULE TO DETECT DISEASES AT AN EARLY ONSET", filed on Jan. 6, 2020 and in its related U.S. non-provisional patent applications (with all benefit provisional patent applications) are incorporated in its entirety herein with this application.

The intelligent appliance 880 can acquire information on a barcode/RFID/near-field communication tag on a product by utilizing its radio module. The intelligent appliance 880 is aware of its location via its indoor/outdoor position module (within the radio module and module specific software 640) and it can search for a price/distribution location. Thus, the intelligent appliance 880 can enable real-world physical search.

The intelligent appliance 880 can enable content over-IP (e.g., Skype service) via an ambient Wi-Fi/Wi-Max network, thus disrupting the traditional carrier controlled cellular business model.

Near-field communication has a short range of about 35 mm-making it an ideal choice for a contact-less (proximity) application. A near-field communication module (with an antenna) and module specific software 680 can allow the user to learn/exchange/transfer/share/transact in a contact-less (proximity) application in real-time. A standalone near-field communication enabled micro-subsystem (e.g., a SD/SIM card form factor) can integrate an IP/micro IP/light weight IP address module and module specific software 500, the storage/memory module and module specific software 780, the near-field communication module (with an antenna) and module specific software 680 and the software module 700. To exchange/transfer/share/transact content, the radio module and module specific software 640 can be integrated with a standalone near-field communication enabled micro subsystem. To enhance the security of the standalone near-field communication enabled micro-subsystem, the sensor module (e.g., a 0.2 mm thick fingerprint sensor component (manufactured by Seiko Epson) reads an electric current on the user's fingertip contact or a sensor component is uniquely synchronized with another sensor component) and module specific software 820 can be integrated. Furthermore, an advanced biometric (fingerprint) sensor module can be fabricated/constructed by combining a silica colloidal crystal with rubber, wherein the silica colloidal crystal can be dissolved in dilute hydrofluoric (HF) acid-leaving air voids in the rubber, thus creating an elastic photonic crystal. An elastic photonic crystal emits an intrinsic color, displaying three-dimensional shapes of ridges, valleys and pores of a fingerprint, when pressed. The central processor module and module specific software 760 can be utilized to compare with the user's captured/stored fingerprint data. Non-matching fingerprint data would render the standalone near-field communication enabled micro-subsystem unusable in case of abuse/fraud/theft.

The intelligent appliance 880 can include a sketch pad electronic module and a stylus, wherein the sketch pad electronic module includes an electronic circuitry for capacitive coupling, a transparent input matrix component and a write-erase switch.

Details of the sketch pad electronic module have been described/disclosed in U.S. Non-Provisional patent application Ser. No. 13/448,378 entitled "SYSTEM AND METHOD FOR MACHINE LEARNING BASED USER APPLICATION", filed on Apr. 16, 2012 and in its related U.S. non-provisional patent applications (with all benefit provisional patent applications) are incorporated in its entirety herein with this application.

The intelligent appliance 880 can also include a personal awareness assistant electronic module, wherein the personal awareness electronic module includes a microphone and/or an audio recorder.

The personal awareness assistant electronic module categorizes information or data received by the personal awareness assistant electronic module into a database.

Details of the personal awareness assistant electronic module have been described/disclosed in U.S. Non-Provisional patent application Ser. No. 13/448,378 entitled "SYSTEM AND METHOD FOR MACHINE LEARNING BASED USER APPLICATION", filed on Apr. 16, 2012 and in its related U.S. non-provisional patent applications (with all benefit provisional patent applications) are incorporated in its entirety herein with this application.

Five critical contactless (proximity) applications are: (a) product/service discovery/initiation, (b) peer-to-peer exchange/transfer/share/transaction, (c) machine-to-machine exchange/transfer/share/transaction, (d) remote access of an appliance/subsystem/system/terminal and (e) access authentication.

Product/Service Discovery/Initiation

The standalone near-field communication enabled micro-subsystem, in contactless proximity of another near-field communication enabled appliance/subsystem/system/terminal, receives a URL (website) to (a) provide information about a product/service, (b) receive direct and/or peer-to-peer marketing (e.g., coupon/advertisement/promotion/brand loyalty program) and (c) monitor/measure the effectiveness of a marketing campaign.

Peer-To-Peer Exchange/Transfer/Share/Transaction

The user can share social network/business profile/microloan/microcontent in contactless proximity of the near-field communication enabled appliance/subsystem/system/terminal of another user.

Machine-To-Machine Exchange/Transfer/Share/Transaction

The user can transact money/microloan/microcontent in contactless proximity of a near-field communication enabled appliance/subsystem/system/terminal.

An example, the standalone near-field communication enabled micro-subsystem can enable printing a stored photo, in contactless proximity of a near-field communication enabled printer and displaying a stored movie, in contactless proximity of a near-field communication enabled TV.

A near-field communication enabled TV can be fabricated/constructed similarly to the intelligent appliance 880.

Another example, the standalone near-field communication enabled micro-subsystem can enable purchasing a travel ticket, in contactless proximity of a near-field communication enabled ticket appliance/subsystem/system/terminal. Such a ticket can be verified and/or located by an indoor position module without need for human input.

Another example, a near-field communication enabled a printer module integrated with an electro-mechanical weighing module, an electro-mechanical postage dispensing module and a software module for calculating the postage price based on weight, distance, priority level and delivery method can enable purchasing postage efficiently.

Remote (Appliance/Subsystem/System/Terminal) Access

The user's profile, bookmarks, address book, preferences, settings, applications and contents of an appliance/subsystem/system/terminal could be stored securely in the standalone near-field communication enabled micro-subsystem, in contactless proximity of a near-field communication enabled appliance/subsystem/system/terminal, it will load an original version of the user's profile, bookmarks, address book, preferences, settings, applications and content.

Access Authentication

The user can utilize the standalone near-field communication enabled micro-subsystem, in contactless proximity of a near-field, communication enabled appliance/subsystem/system/terminal to enable authentication of an appliance/subsystem/system/terminal.

The standalone near-field communication enabled micro-subsystem (as discussed above) can be integrated (by inserting into an electro-mechanical socket) with the intelligent appliance 880.

Direct marketing (e.g., coupon/advertisement/promotion/brand loyalty program) exists via AdMob and Groupon. A static social network exists via MySpace and Facebook. The primary motivation of the user is social connections with other users on a social network website. However, a web based social network can limit human bonds.

The standalone near-field communication coupled micro-subsystem/intelligent appliance can enable an off-line social exchange and direct and/or peer-to-peer marketing.

A personalized social network can utilize an augmented identity (e.g., Recognizr) in addition to a profile. A personalized social network can keep track of information/discussion/interests, which are important to the user/users and make such information/discussion/interests available to the user/users when the user/users are either online or off-line.

Direct marketing can be segmented by demographics/geographical locations (e.g., gender/marital status/age/religion/interests/education/work-position/income/credit profile/net asset/zip code). However, adding real-time geographical location to direct marketing can be useful (e.g., the user close to a stadium and minutes before an event can purchase a ticket and after an event can receive direct marketing based on the user's interests/preferences/patterns. This is personalized marketing).

Personalization can be enhanced by the intelligence rendering software module 700 (e.g., a machine learning/ iterative learn-by-doing/natural learning algorithm in a software module). The intelligent software agent (a do-engine) can search the internet automatically and recommend to the user a product/service/content based on the user's interests/preferences/patterns. Integration of the user's social network profile, the user's interests/preferences/patterns, the user's real-time geographical location, data/information/images from the objects 720 and interaction (of the objects 720s with the intelligent subscriber subsystem 340 and the intelligent appliance 880) collectively can embed physical reality into internet space and internet reality into a physical space thus, it can enrich the user's experience and need.

Figure 7:
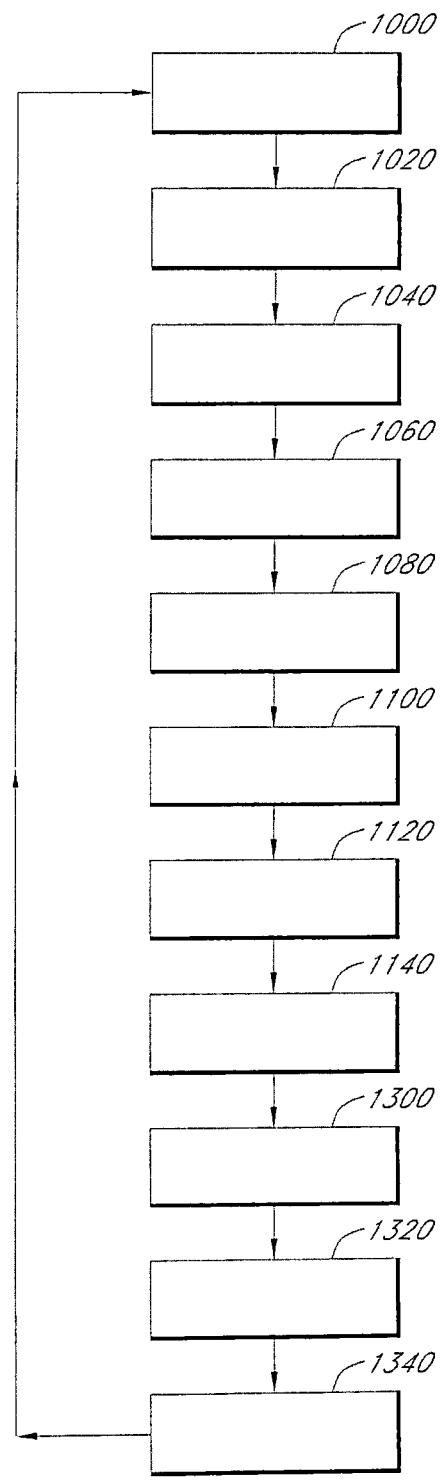
FIG. 7 illustrates a method flow-chart of an intelligent, location based and personalized social network, according to another embodiment of the present invention.

FIG. 7 illustrates a method flow-chart enabling an intelligent, location based and personalized social network, which can be realized by including at least the following steps: (a) authenticating the user 1000, (b) understanding the user's profile (an augmented identity is preferred) 1020, (c) remembering the user's need 1040, (d) remembering the user's conversation 1060, (e) reminding the user's need 1080, (f) determining the user's location (real-time is preferred) 1100, (g) searching the internet for the user's need (the intelligent software agent is preferred) 1120, (h) recommending a product/service best suited for the user's need 1140, (i) developing a learning algorithm 1300 (e.g., a machine learning/iterative learning-by-doing/natural learning algorithm in the software module 700) from a plurality of the users' activities, (j) utilizing a learning algorithm 1320 and (k) re-iterating all previous steps from (a) to (j) in a loop cycle 1340.

Figure 8:
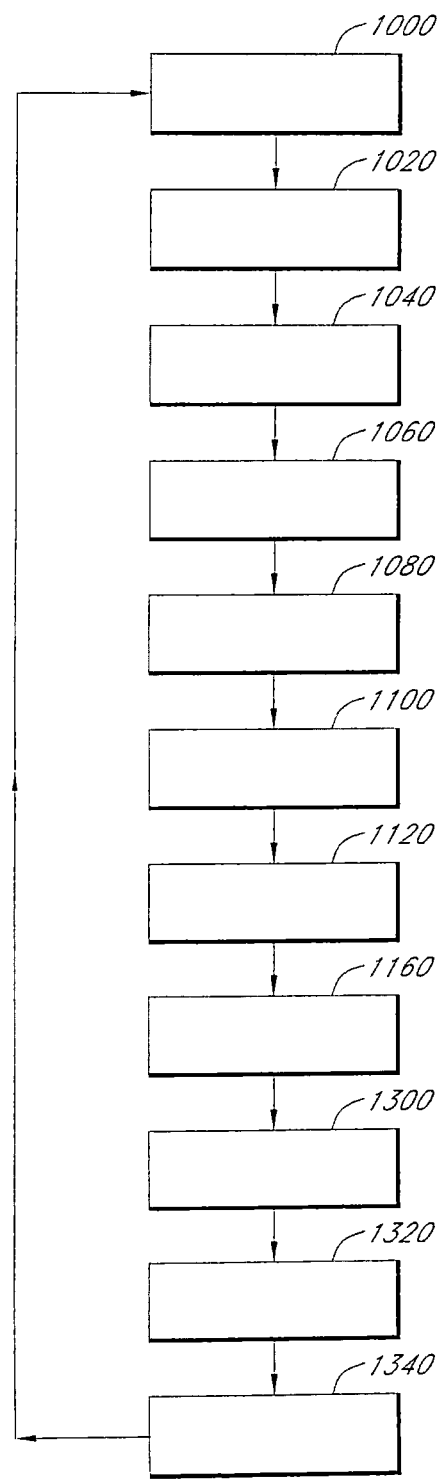
FIG. 8 illustrates a method flow-chart of intelligent, location based, and personalized direct marketing, according to another embodiment of the present invention.

FIG. 8 illustrates a method flow-chart enabling intelligent, location based and personalized direct marketing (e.g., coupon/advertisement/promotion/brand loyalty program) by including at least the following steps: (a) authenticating the user 1000, (b) understanding the user's profile (an augmented identity is preferred) 1020, (c) remembering the user's need 1040, (d) remembering the user's conversation 1060, (e) reminding the user's need 1080, (f) determining the user's location (real-time is preferred) 1100, (g) searching the internet for the user's need (the intelligent software agent is preferred) 1120, (h) delivering direct marketing material (e.g., coupon/advertisement/promotion/brand loyalty program) based on the user's need 1160, (i) developing the learning algorithm 1300 (e.g., a machine learning/iterative learning-by-doing/natural learning algorithm in the software module 700) from the plurality of users' activities, (j) utilizing the learning algorithm 1320 and (k) re-iterating all previous steps from (a) to (j) in a loop cycle 1340.

A method of enabling intelligent, location based and personalized peer-to-peer marketing (e.g., coupon/advertisement/promotion/brand loyalty program) can be realized by including at least the steps: (a) authenticating the user 1000, (b) understanding the first user's profile (an augmented identity is preferred) 1020, (c) authenticating a second user 1000A, (d) understanding the second user's profile (an augmented identity is preferred) 1020A, (e) determining the first user's location (real-time is preferred) 1100, (f) determining the second user's location (real-time is preferred) 1100A, (g) communicating and/or sharing with a plurality of users for a collective need (an augmented identity is preferred) 1180, (h) determining the users' locations (real-time is preferred) 1100B, (i) delivering marketing material (e.g., coupon/advertisement/promotion/brand loyalty program) from the first user to the second user and/or users, seeking marketing material (e.g., coupon/advertisement/promotion/brand loyalty program) 1160A, (j) developing the learning algorithm 1300 (e.g., a machine learning/iterative learning-by-doing/natural learning algorithm in the software module 700) from a plurality of the users' activities, (k) utilizing the learning algorithm 1320 and (o) re-iterating all previous steps from (a) to (k) in a loop cycle 1340.

A method of enabling an intelligent, location based and personalized peer-to-peer microloan transaction can be realized by including at least the steps: (a) authenticating the user 1000, (b) understanding the first user's profile (an augmented identity is preferred) 1020, (c) authenticating a second user 1000A, (d) understanding the second user's profile (an augmented identity is preferred) 1020A, (e) determining the first user's location (real-time is preferred) 1100, (f) determining the second user's location (real-time is preferred) 1100A, (g) communicating and/or sharing with a plurality of the users for a collective need (an augmented identity is preferred) 1180, (h) determining the users' locations (real-time is preferred) 1100B, (i) determining legal parameters of a microloan 1200, (j) agreeing on legal parameters of the microloan 1220, (k) establishing a security protocol between the first user and the second user and/or users, seeking the microloan 1240, (l) delivering the microloan from the first user to the second user and/or users, seeking the microloan 1160B, (m) developing the learning algorithm 1300 (e.g., a machine learning/iterative learning-by-doing/natural learning algorithm in the software module 700) from a plurality of the users' activities, (n) utilizing the learning algorithm 1320 and (o) re-iterating all previous steps from (a) to (n) in a loop cycle 1340.

A method of enabling an intelligent, location based and personalized peer-to-peer microcontent transaction can be realized by including at least the steps: (a) authenticating the user 1000, (b) understanding the first user's profile (an augmented identity is preferred) 1020, (c) authenticating a second user 1000A, (d) understanding the second user's profile (an augmented identity is preferred) 1020A, (e) determining the first user's location (real-time is preferred) 1100, (f) determining the second user's location (real-time is preferred) 1100A, (g) communicating and/or sharing with a plurality of users for a collective need (an augmented identity is preferred) 1080, (h) determining the users' locations (real-time is preferred) 1100B, (i) determining legal parameters of microcontent transfer 1200 (j) agreeing on legal parameters of the microcontent transfer 1220, (k) establishing a security protocol between the first user and the second user and/or users, seeking the microcontent transfer 1240, (l) delivering the microcontent from the first user to the second user and/or users, seeking the microcontent 1160C, (m) developing the learning algorithm 1300 (e.g., a machine learning/iterative learning-by-doing/natural learning algorithm in the software module 700) from a plurality of the users' activities, (n) utilizing the learning algorithm 1320 and (o) re-iterating all previous steps from (a) to (n) in a loop cycle 1340.

Figure 9:
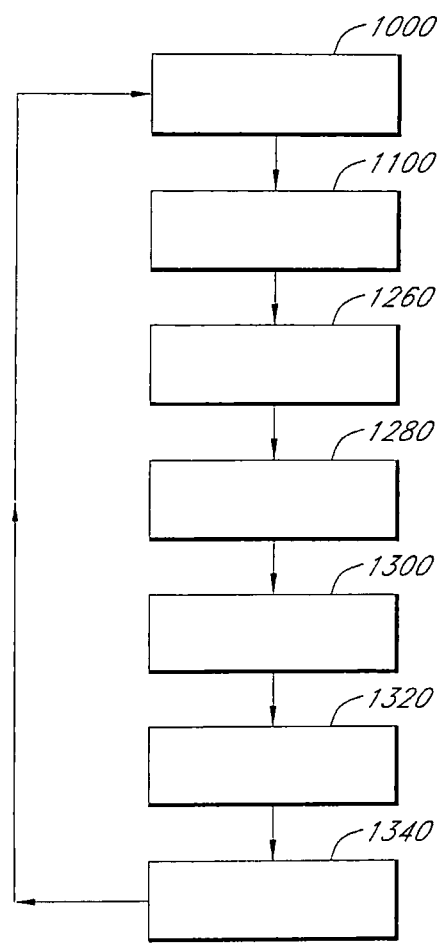
FIG. 9 illustrates a method flow-chart of intelligent, location based and personalized secure contactless (proximity) internet access authentication, according to another embodiment of the present invention.

FIG. 9 illustrates a method flow-chart enabling intelligent, location based and personalized secure contactless (proximity) internet access authentication can be realized by including at least the steps of: (a) authenticating the user 1000, (b) determining the first user's location (real-time is preferred) 1100, (b) coming in the proximity of a near-field enabled appliance/subsystem/system/terminal 1260, (c) authenticating the user for the internet 1280, (d) developing the learning algorithm 1300 (e.g., a machine learning/iterative learning-by-doing/natural learning algorithm in the software module 700) from a plurality of users' activities, (e) utilizing the learning algorithm 1320 and (f) re-iterating all previous steps from (a) to (e) in a loop cycle 1340.

An intelligent software agent can also search the internet automatically and recommend spontaneously in an ambient manner to the user a product/service/content based on the user's interests/preferences/patterns. The intelligence rendering software algorithm in the software module 700, allows the intelligent subscriber subsystem 340 and the intelligent appliance 880 to adapt/learn/relearn the user's interests/preferences/patterns, thereby rendering intelligence.

For example, a bedroom clock connects/couples/interacts with the intelligent subscriber subsystem 340 and/or the intelligent appliance 880 to automatically check on a traffic pattern/flight schedule via the internet, before deciding whether to fiddle with an alarm time without human input. When a rechargeable toothbrush detects a cavity in the teeth, it sends a signal through its electrical wiring and connects/couples/interacts with the intelligent subscriber subsystem 340 and/or the intelligent appliance 880, automatically accesses a location based/assisted dentist's electronic appointment book for a consultation without human input.

The intelligent appliance 880 can include or couple with a spatial computing system. A spatial computing system can generally include virtual reality (VR) application, augmented reality application, mixed reality application (MR), digitized items with sensors (e.g., voice/audio control, eye tracking, hand/body tracking a camera sensor, a haptic feedback system, a LiDAR sensor for measuring distances with laser light and making three-dimensional representation in line of sight and in non-line of sight, Global Positioning System (GPS) and a geolocation sensor), real-time video, robotic system, the Internet of Things, computer implementable artificial intelligence/machine learning instructions/algorithm, computer implementable machine vision instructions/algorithm and computer implementable predictive instructions/algorithm connected via a remote/cloud server-enabling the sensors/machines/motors to couple with each other in near real-time/real-time, thus creating an extended reality (XR) for human to machine and machine to machine interactions.

For example, a digital floor plan of a house can be integrated with a digitally cataloged map of all items (including the connected sensors) in the house, as an elderly person moves through the house, the lights in the elderly person's path will automatically switch on and off, the table will move by itself to improve access to a refrigerator. The furniture will move by itself to protect the elderly person from falling, while simultaneously alerting the family member/911 emergency or an integrated monitoring station.

A spatial computing system can enable physical space to send an input request to a computer and receive an output recommendation from the computer.

The intelligent appliance 880 can integrate a chemical/biosensor module (e.g., to monitor/measure body temperature, % oxygen, heart rhythm blood glucose concentration, carbonyl sulfide gas emission due to a liver/lung disease and a biomarker for a disease parameter) with module specific software.

A zinc oxide nanostructure can detect many toxic chemicals. Also, a quantum cascade DFB/DBR/DR laser (with an emission wavelength in mid-to-far infrared range) can detect a part per billion amount of carbonyl sulfide gas. Wavelength switching of a quantum cascade DFB/DBR/DR laser can be achieved by temperature, utilizing a thin-film resistor/heater, while electrically insulating a laser bias current electrode. Wavelength switching by temperature is a slow (about ten milliseconds) thermal process. However, wavelength switching by electrical currents on multiple segments of a quantum cascade DFB/DBR/DR laser is a rapid (about one millisecond) process. A larger wavelength tuning range can be achieved by an array (a monolithic array is preferred) of multi-segment quantum cascade DFB/DBR/DR lasers. Furthermore, a quantum cascade DFB/DBR/DR laser can emit in terahertz wavelength (85 µm to 150 µm) range, where a metal has a high reflectivity. Thus, a quantum cascade DFB/DBR/DR laser is ideal for metal detection (security).

A compact biomarker-on-a-chip to monitor/measure a disease parameter can be fabricated/constructed by analyzing a change in reflectance and/or a Raman shift and/or surface electric current due to a disease-related biomarker presence (with a specific antibody at about a picogram per mL concentration) on a surface of a two-dimensional/three-dimensional photonic crystal of dielectric material. Confirmation of a single biomarker is not conclusive for the onset/presence of a disease. Identifications of many biomarkers are necessary to predict the onset/presence of a disease. However, a two-dimensional/three-dimensional photonic crystal of dielectric material, incident with a multi-wavelength (blue, green and red) light source can be utilized for simultaneous identifications of many biomarkers of a disease. A multi-wavelength (blue, green and red) light source can be fabricated/constructed as follows: optically pumping different-sized photonic crystals, whereas the photonic crystals can individually emit blue, green and red light based on their inherent sizes. Optical pumping can be generated from optical emission by electrical activation of semiconductor quantum-wells. Blue, green and red light can be multiplexed/combined to generate white light. A Raman shift scattered by the biomarker requires an expensive high-performance laser. However, a Raman sensor (requires an inexpensive CD laser and a wavelength tunable filter) can monitor/measure a Raman shift due to a disease-related biomarker presence. A biomarker molecule can induce a change in surface induced electric current when it binds to an atomically thin graphene surface (graphene's electronic sensitivity to biomolecular adsorption). A thin graphene surface may contain graphene oxide.

Alternatively, a surface-enhanced Raman spectroscopy (SERS) based Raman probe can be adopted, utilizing a substrate (e.g., a graphene/graphene oxide substrate), a miniature spectrophotometer and a laser (e.g., a 785 nm laser) to detect a presence of a disease-related biomarker.

A surface-enhanced Raman spectroscopy specific laser can be (i) a single-longitudinal mode laser or (ii) a distributed feedback (DFB)/distributed Bragg reflection (DBR) diode laser or (ii) a volume Bragg-grating (VBG) frequency-stabilized diode laser.

A surface-enhanced Raman spectroscopy specific miniature spectrophotometer can be a spectrophotometer-on-a-chip, which is based on cascaded series of arrayed waveguide grating routers (AWGR).

The substrate can have an array or a network of three-dimensional (metal) structures or three-dimensional protruded optical nanoantennas to enhance surface-enhanced Raman spectroscopy based Raman signal.

Details of a three-dimensional (metal) structure(s) have been described/disclosed in U.S. Non-Provisional patent application Ser. No. 16/602,966 entitled "OPTICAL BIO-MODULE TO DETECT DISEASES AT AN EARLY ONSET", filed on Jan. 6, 2020 and in its related U.S. non-provisional patent applications (with all benefit provisional patent applications) are incorporated in its entirety herein with this application.

Details of a three-dimensional (metal) structure(s) have been described/disclosed in U.S. Non-Provisional patent application Ser. No. 15/731,577 entitled "OPTICAL BIO-MODULE TO DETECT DISEASES AT AN EARLY ONSET", filed on Jul. 3, 2017 and in its related U.S. non-provisional patent applications (with all benefit provisional patent applications) are incorporated in its entirety herein with this application.

Details of a three-dimensional (metal structure(s)) have been described/disclosed in U.S. Non-Provisional patent application Ser. No. 13/663,376 entitled "OPTICAL BIOMODULE TO DETECT DISEASES", filed on Oct. 29, 2012 and in its related U.S. non-provisional patent applications (with all benefit provisional patent applications) are incorporated in its entirety herein with this application.

Examples of three-dimensional protruded optical nanoantennas have been described/disclosed in FIGS. 12H-12O3 of U.S. Non-Provisional patent application Ser. No. 16/602,906 entitled "OPTICAL BIOMODULE TO DETECT DISEASES AT AN EARLY STAGE", filed on Jan. 6, 2019.

Further details of the three-dimensional protruded optical nanoantennas have been described/disclosed in U.S. Non-Provisional patent application Ser. No. 16/602,906 entitled "OPTICAL BIOMODULE TO DETECT DISEASES AT AN EARLY STAGE", filed on Jan. 6, 2019 and in its related U.S. non-provisional patent applications (with all benefit provisional patent applications) are incorporated in its entirety herein with this application.

However, surface-enhanced Raman spectroscopy based hot spot is generally less than 10 nm and a biomarker (e.g., bacteria/virus) is generally much larger in diameter than 10 nm. This size mismatch can yield poor reliability in the detection of a biomarker.

A volume-enhanced Raman spectroscopy (VERS) based Raman probe signal of a biomarker can be obtained within a fluidic container, utilizing paramagnetic magnetic nanoparticles, Raman active molecules (wherein each Raman active molecule is functionalized with a biomarker selective/specific biomarker binder), a miniature spectrophotometer and a laser.

Alternatively, silver nanoparticles labeled with Raman active molecules (wherein each Raman active molecule is functionalized with a biomarker selective/specific biomarker binder) can be mixed with a biomarker. This mixture can propagate through a fluidic channel (alternatively, the fluidic channel can have an array of angled (about 70-degree angle) silver nanorods, without the need of silver nanoparticles in the first place) at the focus of a laser to generate surface-enhanced Raman spectroscopy signal by the Raman active molecules.

In general, a Raman probe can include either a surface-enhanced Raman spectroscopy based Raman probe or a volume-enhanced Raman spectroscopy (VERS) based Raman probe.

Alternative to Raman sensor/Raman probe, a Förster resonance energy transfer (FRET) based probe can be utilized, which includes a laser, a photodetector and an optical filter. Furthermore, Förster resonance energy transfer signal may be enhanced significantly in presence of one or more (or an array of) three-dimensional (metal) structures or protruded optical nanoantennas, optimized for (i) donor's absorption-emission spectrum and (ii) acceptor's absorption-emission spectrum.

Details of the Förster resonance energy transfer based probe have been described/disclosed in U.S. Non-Provisional patent application Ser. No. 16/602,966 entitled "OPTICAL BIOMODULE TO DETECT DISEASES AT AN EARLY ONSET", filed on Jan. 6, 2020 and in its related U.S. non-provisional patent applications (with all benefit provisional patent applications) are incorporated in its entirety herein with this application.

Further details of the Förster resonance energy transfer based probe (e.g., FIGS. 57I-57K) have been described/disclosed in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

The above Raman sensor/Raman probe/Förster resonance energy transfer based probe may detect a presence of a disease-related biomarker in a virus laden pandemic.

Alternative to the above Raman sensor/Raman probe/Förster resonance energy transfer based probe, an electrochemical cell with an array of electrodes (wherein the electrochemical cell is further integrated/included with a microfluidic channel to separate plasma/serum from whole blood) can be utilized to measure electrical impedance to detect a presence of a disease-related biomarker in a virus laden pandemic.

Details of an electrochemical cell have been described/disclosed in U.S. Non-Provisional patent application Ser. No. 16/602,966 entitled "OPTICAL BIOMODULE TO DETECT DISEASES AT AN EARLY ONSET", filed on Jan. 6, 2020 and in its related U.S. non-provisional patent applications (with all benefit provisional patent applications) are incorporated in its entirety herein with this application.

The above Raman sensor/Raman probe/Förster resonance energy transfer based probe can enable location based autonomous reporting/autonomous contact tracing, when it is coupled with the intelligent appliance 880 and/or a wearable device to measure health parameters (e.g., body temperature, oxygen saturation, heart rate and blood pressure).

Details of a wearable device have been described/disclosed in U.S. Non-Provisional patent application Ser. No. 16/602,404 entitled "SYSTEM AND METHOD OF. AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

Furthermore, an array of graphene biosensors can detect many biomarkers of a disease thus, enabling a personalized ultra-compact diagnostic module, which can be connected/coupled/interacted with the intelligent subscriber subsystem 340 and/or the intelligent appliance 880.

A biological lab-on-a-chip is a module that integrates a few bioanalytical functions on a single chip to perform point-of-care disease diagnostics. A miniature biological lab-on-a-chip module manufactured by Ostendum (www.ostendum.com) can be integrated (by inserting into an electromechanical cavity) with the intelligent appliance 880 to perform point-of-care disease diagnostics reliably, quickly and economically. Such a lab result can be transmitted from the intelligent appliance 880 to a location based/assisted physician for interpretation without human input. Furthermore, electrically powered by a nano-generator, zinc oxide nanowires fabricated on gallium nitride/indium gallium nitride/aluminum gallium nitride can be a nanolight source for a biological lab-on-a-chip.

The biological lab-on-a-chip can include (i) a light source (e.g., a laser of a suitable wavelength and/or (ii) a photodetector (or a light sensor) to detect a suitable wavelength and/or (iii) an optical filter to transmit/block a suitable wavelength and/or (iv) a microfluidic channel to propagate/separate/store a biological fluid (e.g., serum/plasma) containing a disease biomarker (e.g., a microRNA (miRNA)-tiny RNA is on average about 22 nucleotides long or an exosome) and a complementary disease biomarker binder (e.g., a sequence of oligonucleotides), wherein the complementary disease biomarker binder can bind/couple with the disease biomarker.

The complementary disease biomarker binder can also include one or more fluorophores. Furthermore, two fluorophores (in about 10 nm proximity) can be designed to obtain Förster resonance energy transfer.

The microfluidic channel can also include an array of three-dimensional protruded optical nanoantennas (NOAs) to enhance Förster resonance energy transfer/efficiency, if properly designed.

Examples of three-dimensional protruded optical nanoantennas have been described/disclosed in FIGS. 12H-12O3 of U.S. Non-Provisional patent application Ser. No. 16/602, 906 entitled "OPTICAL BIOMODULE TO DETECT DISEASES AT AN EARLY STAGE", filed on Jan. 6, 2019.

Further details of the three-dimensional protruded optical nanoantennas have been described/disclosed in U.S. Non-Provisional patent application Ser. No. 16/602,906 entitled "OPTICAL BIOMODULE TO DETECT DISEASES AT AN EARLY STAGE", filed on Jan. 6, 2019 and in its related U.S. non-provisional patent applications (with all benefit provisional patent applications) are incorporated in its entirety herein with this application.

The microfluidic channel can also include a substrate of two or more materials-including, but not limited to a metamaterial (e.g., Epsilon-Near-Zero (ENZ) metamaterial) of exceptional optical properties.

Alternatively, the biological lab-on-a-chip can include a nanopore based DNA/RNA sequencing biomodule which includes a molecular system (including nucleotides-nucleotides which make up DNA utilizing adenine (A), thymine (T), cytosine (C) and guanine (G). In RNA, the thymine is replaced with uracil (U) or amino acids) to be sensed, a nanohole/nanoscaled hole (for passing the molecular system to be sensed) of about less than 10 nm in diameter (however, the nanohole/nanoscaled hole is typically about 1.5 nm in diameter) and an electronic circuit electrically coupled with the nanohole/nanoscaled hole to measure electrical signals related to the movement of the nucleotides or amino acids through the nanohole/nanoscaled hole.

The above nanopore based DNA/RNA sequencing biomodule can enable location based autonomous reporting/autonomous contact tracing, when it is coupled with the intelligent appliance 880 and/or a wearable device to measure health parameters (e.g., body temperature, oxygen saturation, heart rate and blood pressure).

Details of a nanopore based DNA/RNA sequencing biomodule have been described/disclosed in U.S. Non-Provisional patent application Ser. No. 13/663,376 entitled "OPTICAL BIOMODULE TO DETECT DISEASES", filed on Oct. 29, 2012 and in its related U.S. non-provisional patent applications (with all benefit provisional patent applications) are incorporated in its entirety herein with this application.

Holographic images of the user's genes/proteins can be stored in the intelligent appliance 880 and such holographic images can enable a physician/surgeon to design a personalized medical and/or surgical treatment.

Furthermore, the intelligent appliance 880 can store a user's encrypted heath data, coupled with a blockchain. The intelligent appliance 880 can transmit the user's encrypted health data (coupled with a blockchain) to a medical professional (e.g., a doctor).

Details of a user's encrypted health data, coupled with a blockchain have been described/disclosed in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

Furthermore, the intelligent appliance 880 coupled with the biological lab-on-a-chip can be utilized for a cloud based healthcare system (e.g., telemedicine or telehealth, which is the distribution of health-related services and information over the internet without any physical presence).

An example of a cloud based healthcare system has been described/disclosed in FIGS. 3G1 & 3G2 of U.S. Non-Provisional patent application Ser. No. 16/873,634 entitled "SYSTEM AND METHOD FOR MACHINE LEARNING AND AUGMENTED REALITY BASED USER APPLICATION", filed on May 26, 2020.

Further details of the cloud based healthcare system have been described/disclosed in U.S. Non-Provisional patent application Ser. No. 16/873,634 entitled "SYSTEM AND METHOD FOR MACHINE LEARNING AND AUGMENTED REALITY BASED USER APPLICATION", filed on May 26, 2020 and in its related U.S. non-provisional patent applications (with all benefit provisional patent applications) are incorporated in its entirety herein with this application.

Many software modules, as discussed in the above paragraphs can consume significant electrical power due to computational complexities. Alternatively, many software modules can be processed at a remote/cloud server. Software modules can be embedded within the intelligent subscriber subsystem 340 and/or the intelligent appliance 880, if electrical power consumption and/or thermal management are feasible. Effective thermal management is critical to fabricate and construct a high-performance intelligent appliance 880. Thermal resistance must be minimized at all material interfaces and materials with closely matching thermal expansion coefficients must be used.

Graphene can be viewed as a plane of carbon atoms extracted from a graphite crystal. Multiple-atomic layers of graphene are easier to fabricate than a single-atomic layer graphene and multiple-atomic layers of graphene retain thermal conductivity of a single-atomic layer graphene. A nanoscaled graphene heat pipe can be utilized to cool a hot spot (or hot spots) within the intelligent appliance 880. For efficient thermal management, a heat sink/heat spreader of graphene/diamond/aluminum nitride/copper/aluminum/silicon/material with closely matching thermal expansion coefficients can be attached (e.g., to the central processor module 760) by utilizing an interface heat transfer material (e.g., Indigo™ www.enerdynesolutions.com). However, a significant (about 10×) heat transfer of a heat sink/heat spreader can be gained by creating a nanostructured (e.g., zinc oxide nanostructures fabricated by microreactor assisted nanomaterial deposition process) surface on the heat sink/heat spreader. Furthermore, microchannels can be fabricated by a laser machining method onto the heat sink/heat spreader for passive air and/or active (air/liquid/micro-scale ion cloud) cooling.

A microscaled ion cloud can be generated as follows: on one side of graphene based microchannels is a carbon nanotube negative electrode, when a negative voltage is switched on, electrons jump from a negative electrode toward a positive electrode, colliding with air molecules near a hot spot (or hot spots) thus, dissipating heat and producing a microscale cloud of positively charged ions. A microscale cloud of positively charged ions drifts towards a present negative electrode. However, before it reaches the present negative electrode, voltage is switched on to another negative electrode at a different position. Forward and reverse wind of a microscale cloud of positively charged ions (created by changing the positions of negative electrodes) can cool a hot spot (or hot spots) within the intelligent appliance 880. Alternatively, high-efficiency nanostructured $50A^0$ thick $Sb_2Te_3$/$10A^0$ thick $Bi_2Te_3$-based thin-film superlattices thermoelectric cooler (TEC)/microrefrigerator (1 mm×3 mm) can also be utilized to cool a hot spot (or hot spots) within the intelligent appliance 880. However, significant thermoelectric cooler (TEC)/microrefrigerator efficiency can be gained by fabricating a quantum wire/quantum dot, transitioning from a two-dimensional superlattice.

Furthermore, the intelligent appliance 880 can be charged via resonant electromagnetic inductive coupling energy transfer without a physical wire.

Aluminum/magnesium alloys have small building blocks-called nanocrystal grains with crystal defects. Nanocrystal grains with crystal defects are mechanically stronger than perfect aluminum/magnesium crystals. The intelligent appliance 880's outer package can be constructed from a nano-engineered aluminum/magnesium alloy, liquid Metal® alloy (www.liquidmetal.com), a carbon-polymer composite (carbon fiber embedded with a molten polymer injection mold) and magnesium metal. Furthermore, an antenna can be fabricated/constructed from a carbon fiber—that is embedded with a metal/conducting polymer.

Figure 10:
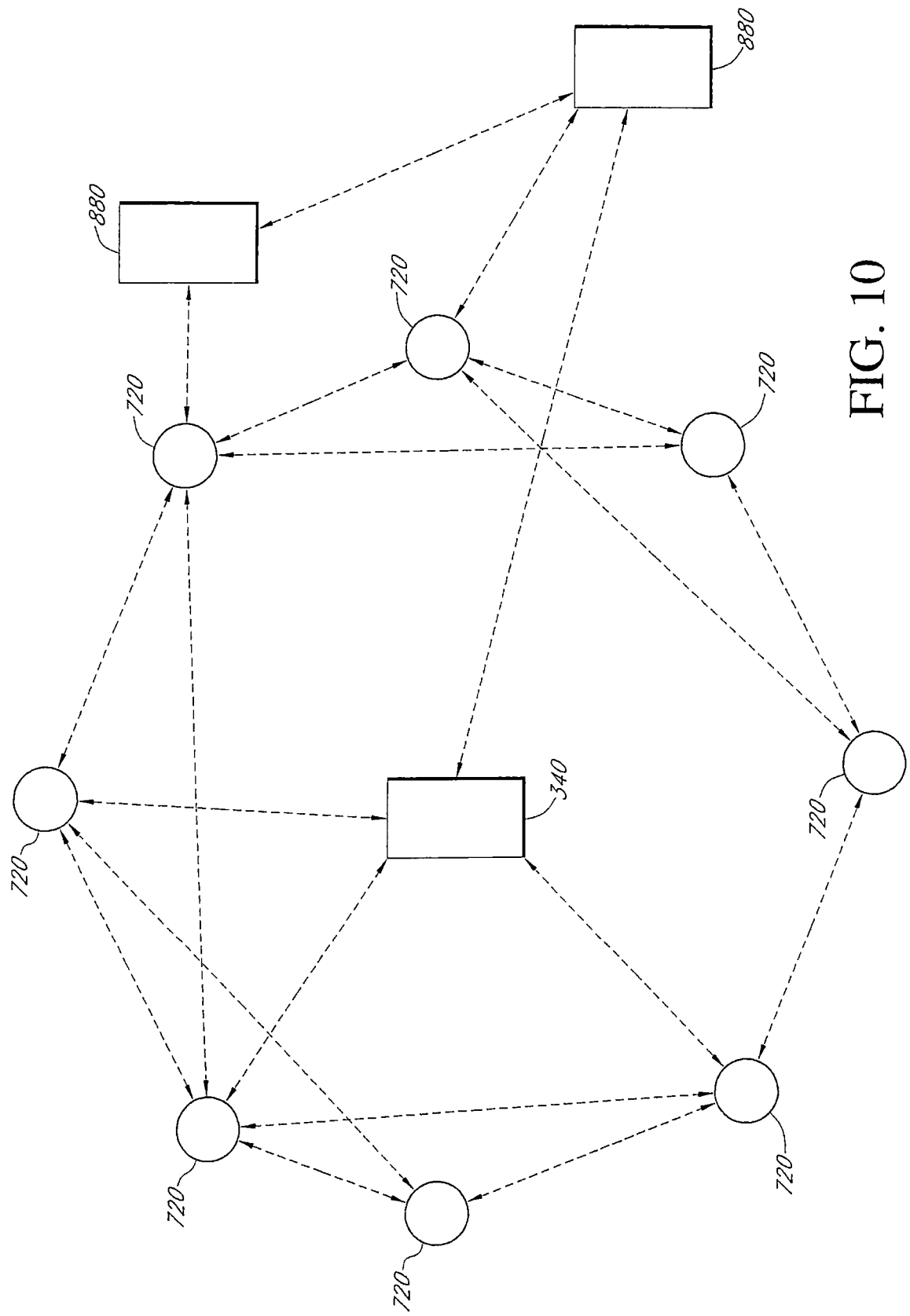
FIG. 10 illustrates connections/couplings/interactions between the object 720 (including with another object 720), the intelligent subscriber subsystem 340 and the intelligent appliance 880, according to another embodiment of the present invention.

FIG. 10 illustrates a block diagram of connections/couplings/interactions (via electrical/optical/radio/sensor/biosensor communication network(s)) between the object(s) 720 with the intelligent subscriber subsystem(s) 340 and the intelligent appliance(s) 880, utilizing internet protocol version 6 (IPv6) and its subsequent versions. The context-awareness is (according to the user's situational context), personalized (tailored to the user's need), adaptive (changes in response to the user's need) and anticipatory (can anticipate the user's desire).

The intelligent subscriber subsystem 340 and the intelligent appliance 880 are both context-aware (inferred from the user's past/present activities, extracted from the user's content/data and explicit in the user's profile) and/or sensor-aware (inferred from data/image/patterns from the object(s) 720). It should be noted that 5G/higher than 5G bandwidth radio (wireless) transceiver integrated circuits can be fast enough to secure data from an array of sensors without lag times. The lack of lag times can enable a user to physically interact with any remote environment (including haptic sensors). But full sensory immersion needed for collaborative telepresence will require lag times substantially much smaller than those acceptable for video calls; however, a predictive artificial intelligence (PAI) algorithm (stored in a non-transitory storage media of the intelligent subsystem) can be utilized to eliminate a user's perception of time lags. Thus, the intelligent subscriber subsystem 340 and/or the intelligent appliance 880 can provide collaborative telepresence, when the intelligent subscriber subsystem 340 and/or the intelligent appliance 880 is coupled with (or includes) 5G/higher than 5G bandwidth radio (wireless) transceiver and a predictive artificial intelligence algorithm to eliminate a user's perception of time lag.

Figure 11:
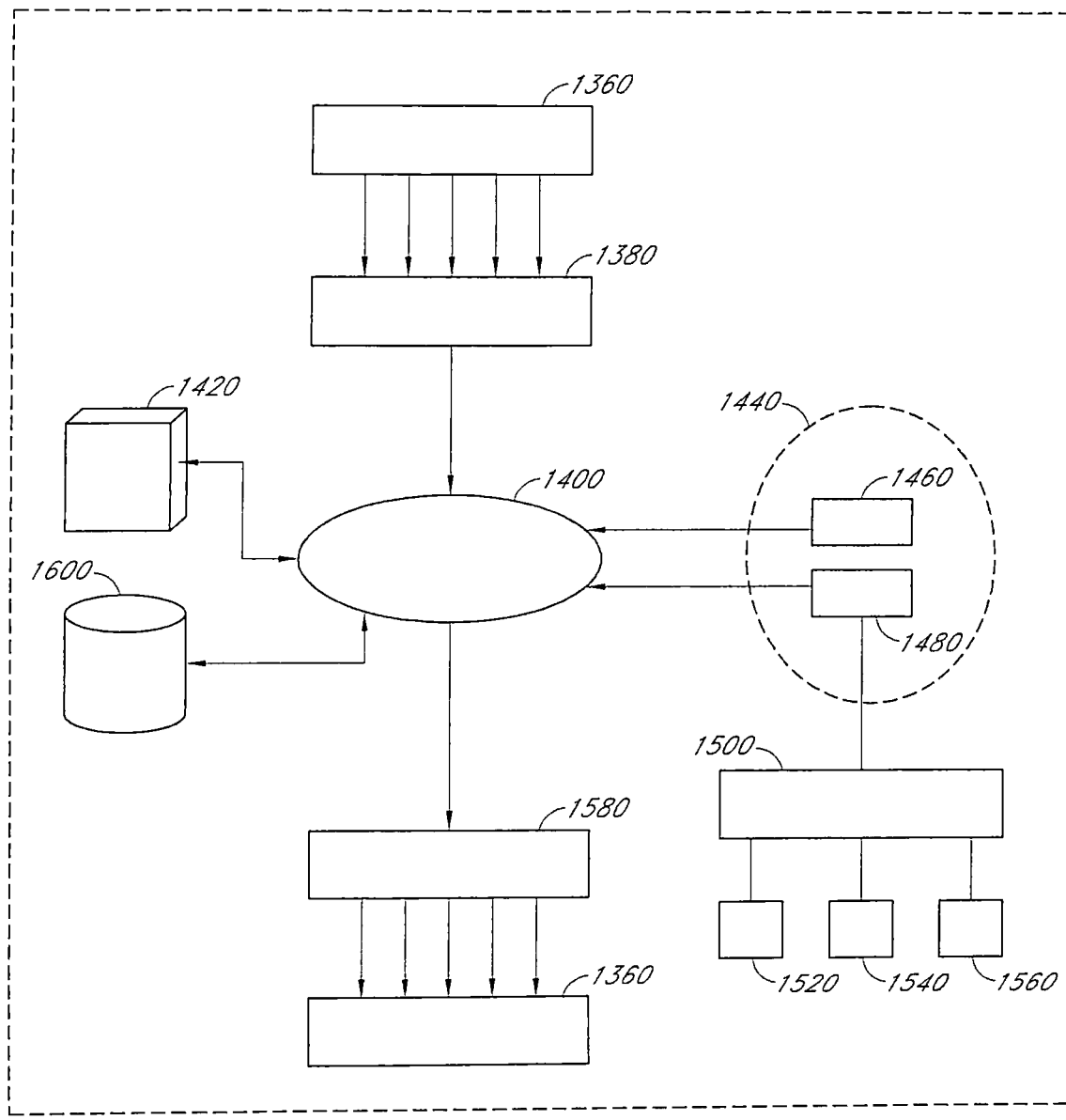
FIG. 11 illustrates a method flow-chart enabling task execution by a software agent, according to another embodiment of the present invention.

FIG. 11 illustrates a method flow-chart enabling a task execution by a software agent. An incoming task is communicated from a communication channel 1360, to an incoming queuing element 1380, to an execution manager 1400. The execution manager 1400 gains information from (and shares with) a transient knowledge element 1420 and a data base element 1600. The execution manager 1400 further gains information from a permanent knowledge element 1440, which includes an attribute element 1460 and a capability element 1480. The capability element 1480 is connected to a task element 1500, which is further connected to a rule element 1520, a method element 1540 and a knowledge source element 1560. Executed/processed tasks from the execution manager 1400 are communicated to an outgoing queuing task controller 1580 to the communication channel 1360.

Furthermore, the intelligent appliance 880 can be coupled with an augmented reality apparatus/augmented reality personal assistant apparatus and/or augmented reality application (app).

Additionally, an augmented reality apparatus/augmented reality personal assistant apparatus can include/integrate one or more computational camera sensors for three-dimensional viewing and sensing of a surrounding area.

A computational camera sensor can generally include a laser and a photodiode, wherein the photodiode can be a PIN photodiode, an avalanche photodiode or a single photon avalanche detector.

Details of the computational camera sensor (e.g., FIGS. 3L-3Z) have been described/disclosed in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

An augmented reality application can enable a user to share location based near real-time/real-time snapshots/holographic snapshots of the contextual world (or contextual situation) around the user-a way of viewing the world through someone else's eyes on his/her way to a place/event.

For example, the user is watching the 2016 NBA final game between the Cleveland Cavaliers v. Golden State Warriors, the user (along with his/her personalized social graph and/or social geotag of geographical data (latitude & longitude) with videos, photographs, websites, e-mails and status updates) may color enhance/edit/geofilter/geotag/personalize the near real-time/real-time snapshots/holographic snapshots of Lebron James blocking the shot of the Golden State Warriors' Andre Iguodala like "unbelievable-superman/batman performance by Lebron James" by either text input or text command in natural language or voice command in natural language from the intelligent appliance 880.

Furthermore, color enhanced/edited/geofiltered/geotagged/personalized holographic snapshots of an individual player can enable a location based Pokemon Go like video game of an individual player.

Details of the augmented reality based application have been described/disclosed in U.S. Non-Provisional patent application Ser. No. 16/873,634 entitled "SYSTEM AND METHOD FOR MACHINE LEARNING AND AUGMENTED REALITY BASED USER APPLICATION", filed on May 26, 2020 and in its related U.S. non-provisional patent applications (with all benefit provisional patent applications) are incorporated in its entirety herein with this application.

Details of the augmented reality device/apparatus have been described/disclosed in U.S. Non-Provisional patent application Ser. No. 16/602,404 entitled "SYSTEM AND METHOD OF AMBIENT/PERVASIVE USER/HEALTHCARE EXPERIENCE", filed on Sep. 28, 2019 and in its related U.S. non-provisional patent applications (with all benefit provisional patent applications) are incorporated in its entirety herein with this application.

Details of the augmented reality personal assistant apparatus have been described/disclosed in U.S. Non-Provisional patent application Ser. No. 14/120,835 entitled "AUGMENTED REALITY PERSONAL ASSISTANT APPARATUS", filed on Jul. 1, 2014, (which resulted in a U.S. Pat. No. 9,823,737, issued on Nov. 21, 2017) and in its related U.S. non-provisional patent applications (with all benefit provisional patent applications) are incorporated in its entirety herein with this application.

Figure 12:
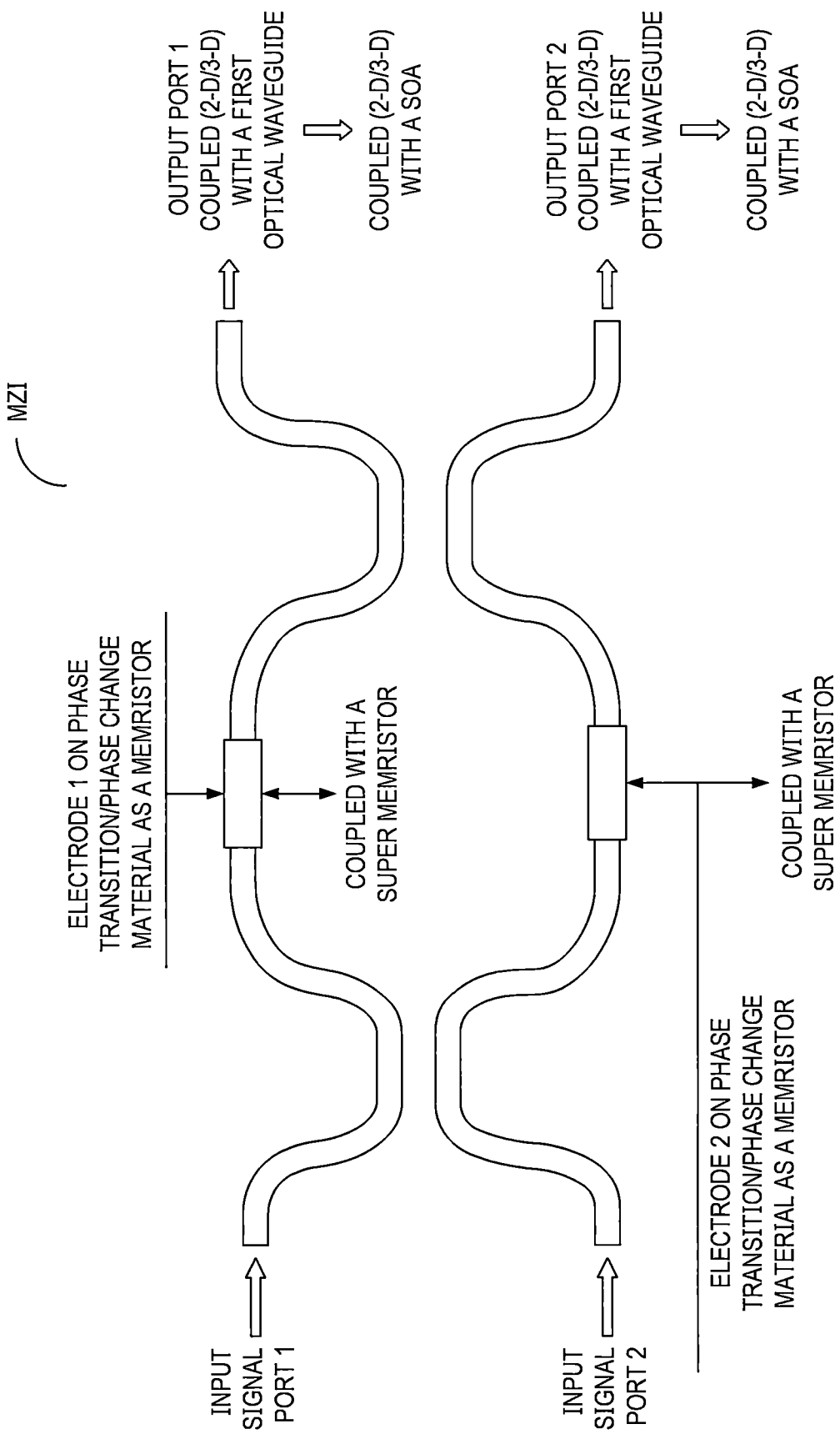
FIGS. 12-14 illustrate three embodiments of a (optically enabled) Super System on Chip. It should be noted that FIGS. 12-13 are reproduced from U.S. Non-Provisional patent application Ser. No. 17/803,388 entitled "SUPER SYSTEM ON CHIP", filed on Jun. 15, 2022.

FIG. 12 illustrates an embodiment of a (optically enabled) Super System on Chip. Specifically, (an optically enabled) Super System on Chip's input/output can be coupled by a Mach-Zehnder interferometer, wherein the Mach-Zehnder interferometer can include a phase transition material or a phase change material or a polymeric material (wherein a phase transition material is electrically and/or optically controlled, but a phase change material is electrically or optically controlled), wherein the Mach-Zehnder interferometer can be coupled by a low-loss first optical (routing) waveguide in either two-dimensions/three-dimensions, wherein the low-loss first optical waveguide can be coupled by a semiconductor optical amplifier (for nonlinear optical processing) in either two-dimensions/three-dimensions. It should be noted that a three-dimensional arrangement can include a vertical coupling.

It should be noted that memristors can be replaced by super memristors. Each super memristor can include (i) a resistor, (ii) a capacitor and (iii) a memristor (e.g., a phase transition/phase change material based memristor).

A phase transition material based memristor can be electrically and/or optically controlled. But a phase change material based memristor can be electrically or optically controlled.

A super memristor can generally mimic a set of neural activities (such as simple spikes, bursts of spikes and self-sustained oscillations with a DC voltage as an input signal)- which can be used for a neuromorphic/neural processing/computing architecture. Furthermore, each super memristor can be electrically/optically controlled.

Figure 13:
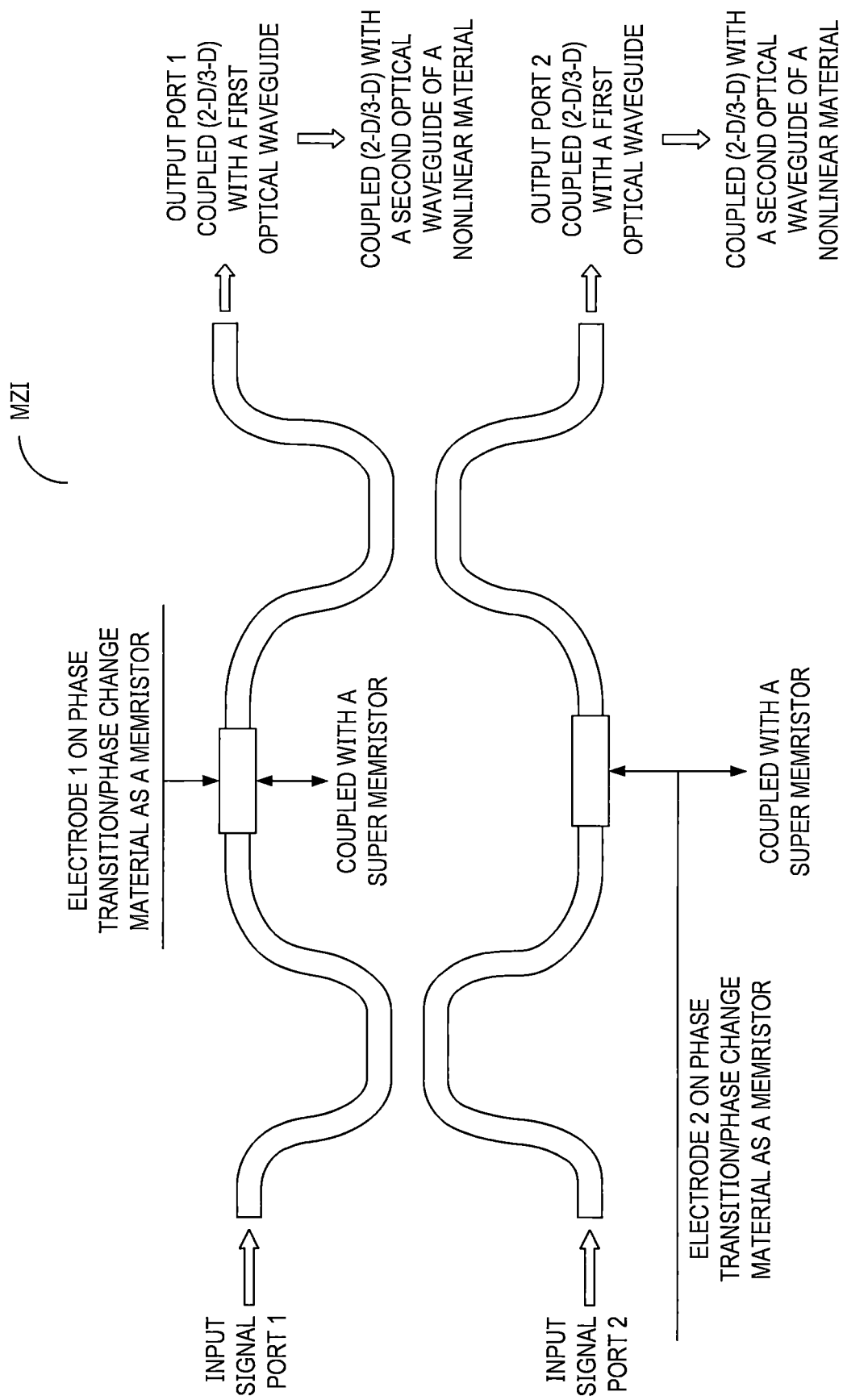

It should be noted that the semiconductor optical amplifier can be replaced by a second optical waveguide containing a nonlinear optical material (e.g., chalcogenide $As_2S_3$) for nonlinear optical processing. This is generally illustrated in FIG. 13.

Figure 14:
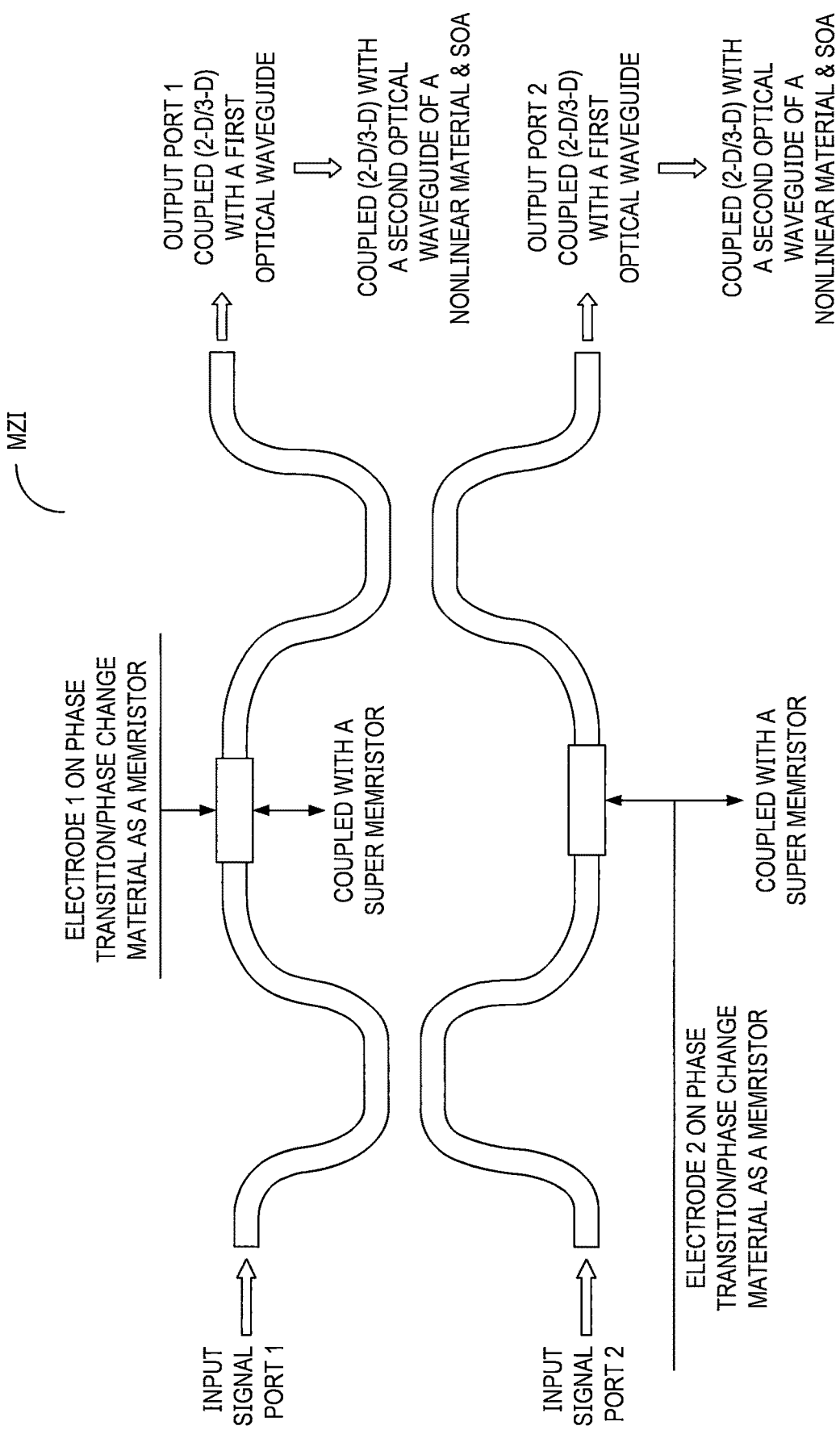

Furthermore, the semiconductor optical amplifier can also include a second optical waveguide containing a nonlinear optical material for advanced nonlinear optical processing. This is generally illustrated in FIG. 14.

Figure 15:
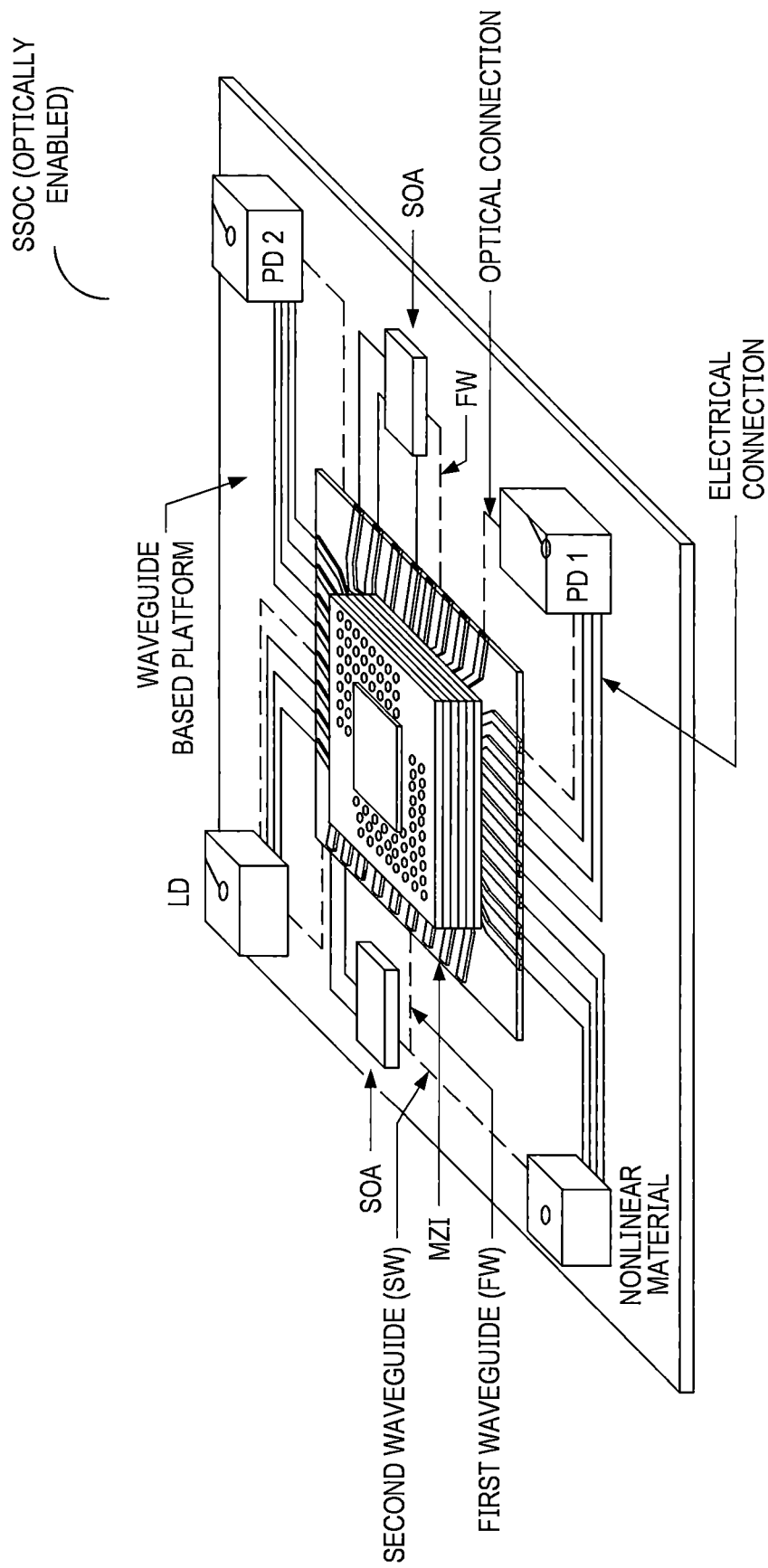
FIG. 15 illustrates a block diagram of a (optically enabled) Super System on Chip in a two-dimensional (2-D) arrangement.

FIG. 15 illustrates a two-dimensional representation of a (optically enabled) Super System on Chip, wherein an input and/or an output of the (optically enabled) Super System on Chip can be coupled with a Mach-Zehnder interferometer, wherein then the Mach-Zehnder interferometer can be coupled with a first optical waveguide (FW) in a two-dimensional arrangement, wherein the first optical waveguide can be coupled optically with a semiconductor optical amplifier. Furthermore, the first optical waveguide can be coupled optically with a second optical waveguide in the two-dimensional arrangement, wherein the second optical waveguide may include a nonlinear optical material. The (optically enabled) Super System on Chip can be coupled optically with a laser (LD) and one or more photodiodes (PDs), denoted as PD1 and PD2 in FIG. 15. It should be noted there are both (i) optical connections via optical waveguides and (ii) electrical connections in FIG. 15.

It should be noted that a semiconductor optical amplifier can be replaced by an optical resonator.

It should be noted that the above two-dimensional representation of the (optically enabled) Super System on Chip (in FIG. 15) can be also realized in a three-dimensional arrangement (wherein the three-dimensional arrangement can include a vertical coupling via precision chip/wafer level bonding or via an optical equivalent of an electrical via hole).

In general, the Super System on Chip can be communicatively interfaced with (i) a first set of computer implementable instructions to process the audio (signal) input, (ii) a second set of computer implementable instructions to analyze and/or interpret contextual data, depending on the context of data and (iii) a third set of computer implementable instructions in artificial neural networks, wherein the artificial neural networks may further include either a transformer model or a diffusion model (which may be further augmented with an evolutionary based algorithm and/or a game theory based algorithm and/or Poisson flow generative model++based algorithm).

It should be noted that the second set of computer implementable instructions and the third set of computer implementable instructions may enable (i) self-learning and/or (ii) a (personal) artificial intelligence based self-learning assistant. (e.g., FIG. 16).

Furthermore, the first set of computer implementable instructions, the second set of computer implementable instructions and the third set of computer implementable instructions can be stored either (i) locally with the Super System on Chip (including optically enabled Super System on Chip) and/or the System-on-a-Chip or (ii) in a remote/cloud server (which can be accessed by the Super System on Chip and/or the System-on-a-Chip over the internet from the remote/cloud server).

Figure 16:
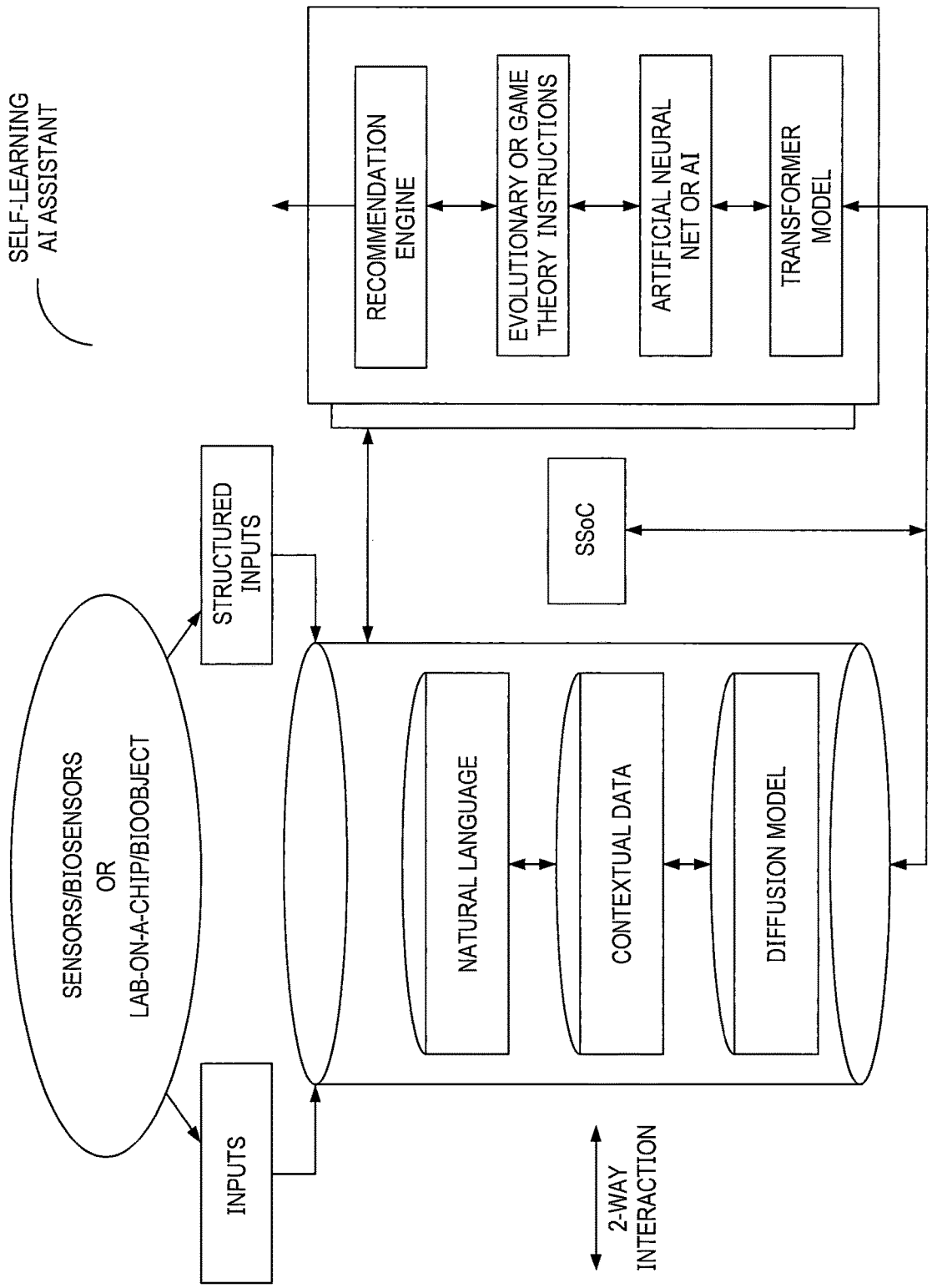
FIG. 16 illustrates an embodiment of a (personal) artificial intelligence based self-learning assistant in a block diagram.

FIG. 16 illustrates an embodiment of a (personal) artificial intelligence based self-learning assistant in a block diagram, wherein a sensor/biosensor/biological lab-on-a-chip/bioobject's data input, audio (signal) input in natural language and contextual data are fed into an artificial neural network to analyze and/or interpret (i) sensor data, (ii) audio (signal) input in natural language and (iii) contextual data.

The artificial neural network may further include a transformer model or a diffusion model (which may be further augmented with an evolutionary based algorithm and/or a game theory based algorithm and/or Poisson flow generative model++ based algorithm).

For example, an autonomous artificial intelligence agent can plan a vacation with high accuracy rate on each step of a multistep process or very good error correction to get anything valuable out of an autonomous artificial intelligence agent that has to take lots of steps. This is contrary to standard artificial intelligence based processes that are run only when a user triggers them and only to accomplish a specific result and then standard artificial intelligence based processes stop. Characteristics of an autonomous artificial intelligence agent are (i) autonomy, (2) continuous learning and (3) reactive and proactive in an environment.

Furthermore, (i) the artificial neural networks (including Kolmogorov-Arnold based neural network architecture and evolutionary algorithm based instructions), (ii) natural language processing and (iii) a collection of declarative knowledge based computer implementable instructions (to enable common sense) can be used to design an autonomous artificial intelligence agent.

An autonomous artificial intelligence agent is a set of computer implementable instructions (an algorithm) and it can have multimodal inputs via text, video and voice.

An autonomous artificial intelligence can analyze the collected data (e.g., from sensors/biosensors) to make informed decisions and take an action or a series of actions to achieve its goals.

An autonomous artificial intelligence can be stored in a non-transitory storage media, located either locally on the intelligent subsystem or in the cloud server.

Thus, the (personal) artificial intelligence based self-learning assistant may be able to recommend useful information proactively without asking/searching for such information explictly (via a Recommendation Engine).

Following FIG. 16, the (personal) artificial intelligence based self-learning assistant can include one or more computer implementable instructions including in artificial neural networks (which can include a transformer model or a diffusion model and may also be augmented with evolutionary based instructions and/or game theory based instructions and/or Poisson flow generative model++ based instructions. Thus, one or more computer implementable instructions can be stored either (i) locally with the Super System on Chip (including optically enabled Super System on Chip) and/or the System-on-a-Chip or (ii) in a remote/cloud server (which can be accessed by the Super System on Chip and/or the System-on-a-Chip over the internet from the remote/cloud server) for the following:

Anticipate a user's needs based on context (e.g., based on an audio signal in natural language or text),
Help with daily tasks/reminders,
Schedule meetings,
Edit photos/images based on context,
Identify photos/images,
Help with nighttime imaging (photography),
Help with smart selfie blurs,
Help with smart selfie blurs with an augmented reality image,
Create custom emojis based on context,
Translate voice memos into another language,
Translate voice memos into text/email into another language,
Generate/phone call on behalf of a user,
Generate/send voicemails on behalf of a user,
Generate/send emails on behalf of a user,
Generate/send contacts on behalf of a user,
Generate/summarize daily voice memos,
Generate/summarize daily action notes,
Remind of daily meetings, based email/voicemail context,
Suggest cooking recipe based on the food images,
Suggest future action items based on context,
Share live events (e.g., Lebron James blocking the shot of the Golden State Warriors' Andre Iguodala),
Annotate/comment on live events (e.g., Lebron James blocking the shot of the Golden State Warriors' Andre Iguodala—with annotation "Witnessing Greatness"),
Share annotated/commented live events,
Compose custom text, images and videos based on context,
Compose custom songs based on context,
Compose similar songs by listening/understanding/audio processing a particular song,
Generate immersive concerts based on context,
Generate immersive games based on context,
Generate/summarize information from the internet search based on a user preference/interest (including an implied preference/interest) without having to open and read multiple links on the internet,
Generate/enable a tipping point alert of any expected virus propagation or any expected natural disaster (e.g., an earthquake or a fire),
Generate immersive digital companion,
Constantly learn from data and interaction with a user and sensors-including implicit feedback from a user, Infer user interests-including implicit interests and enable proactive assistance utilizing contextual reasoning. For example, detect health related problems/issues of a user based on inputs from biosensors (placed on or implanted on a user) and call 911 emergency automatically with the GPS coordinates of a user, without any intervention of a user,
Besides the internet, the (personal) artificial intelligence based self-learning assistant can search/scan other resources such as various search engines (e.g., Bing, Google, Yahoo and Yelp), expert databases, data from existing Question & Answer forums (e.g., ChaCha) and answers drawn from real-time applications that will ask relevant people if they know answer. What makes the Question & Answer forums powerful is that they keep track of each and every question and answer pairing ever asked and every answer ever given. For example, as noted before if an elderly user living alone in a home, suddenly experiences a heart attack, a biosensor/biological lab-on-a-chip on the elderly user can detect such health problem and call 911 emergency automatically with the location coordinates of the elderly user, without any intervention of the elderly user.

The (personal) artificial intelligence (which can be sensor-aware and/or context-aware) based self-learning assistant (an interface for computer implementable instructions) may be considered as a digital personal assistant (DPA), (which can be sensor-aware and/or context-aware) and then coupled/communicatively interfaced with a chatbot interface (that generally mimics human level natural conversation) and one or more computer implementable instructions (stored in one or more non-transitory storage media, located either locally on the intelligent subsystem or in a cloud server) to provide a recommendation (including an implied/inferred/interpreted recommendation) based on a user's interest/preference that was received at the intelligent subsystem. A chatbot interface with natural language processing and semantic analyzer may allow having a natural conversation, as opposed to using an inherent keyboard for everything. Semantic analysis is a subfield of natural language processing that attempts to understand the meaning of natural language of the given text, while considering the context, logical structuring of sentences and grammar. Semantic analyzer can understand the context of natural language and/or detect emotion/sarcasm and extract valuable information from unstructured data, achieving human-level accuracy. Utilizing library learning (e.g., the library induction from language observations (LILO) and/or the action domain acquisition (ADA)) the chatbot can learn, perceive, reason and represent human level natural conversation. The library induction from language observations-a neurosymbolic framework that can synthesize, compress and document computer codes and it can utilize a large language model (LLM) to cut and combine codes into libraries of readable and reusable algorithms. Similarly, the action domain acquisition (natural language that guides artificial intelligence based algorithm for multi-step task planning) can enable sequential decision making with artificial intelligence based algorithms.

Furthermore, the (personal) artificial intelligence based self-learning assistant can be communicatively interfaced with one or more computer implementable instructions (stored in one or more non-transitory storage media, located either locally on the intelligent subsystem or in a cloud server) to learn through an audio signal (e.g., voice) (via computer implementable instructions in natural language understanding/processing—stored in one or more non-transitory storage media, located either locally on the intelligent subsystem or in a cloud server), text, video, sensor data (e.g., from a sensor/biosensor) and (gained) experience by solving iterative problems.

Furthermore, the (personal) artificial intelligence based self-learning can enhance utility of the (personal) artificial intelligence based self-learning assistant in audio signal enabled intelligent (self-learning) computing and enable the following: Sentiment analysis, Learning/adapting to user preference and intent (including an implied/inferred/interpreted intent), Understanding user behavior pattern and responding proactively.

The (personal) artificial intelligence based self-learning assistant can be communicatively interfaced with an autonomous artificial intelligence agent, (e.g., it can plan a vacation) with high accuracy rate on each step of a multistep process or very good error correction to get anything valuable out of an autonomous artificial intelligence agent that has to take lots of steps. This is contrary to standard artificial intelligence based processes that are run only when a human triggers them and only to accomplish a specific result and then standard artificial intelligence based processes stop. Characteristics of an autonomous artificial intelligence agent are (i) autonomy, (2) continuous learning and (3) reactive and proactive in an environment.

The (personal) artificial intelligence based self-learning assistant communicatively interfaced with an autonomous artificial intelligence agent can book on the next flight for a user, when the (personal) artificial intelligence based self-learning assistant finds out from the internet and other resources that the previous flight is canceled. The (personal) artificial intelligence based self-learning assistant can then communicate with a user's family about the delay in arrival, or newly booked flight and then notify/reorder the airport shuttle/taxicab accordingly to pick up a user from the airport.

The (personal) artificial intelligence based self-learning assistant interfaced with an autonomous artificial intelligence agent can enable an intelligent and intuitive internet search interface (Product/Service Matching/Searching a Buyer/User based on a User Profile, as opposed to traditional time-consuming internet search (e.g., on Google/Bing/Yahoo).

Details of an intelligent and intuitive internet search interface have been described/disclosed (e.g., FIG. 1) in U.S. Non-Provisional Patent Application No. U.S. Non-Provisional patent application Ser. No. 16/873,033 entitled "SYSTEM AND METHOD FOR MACHINE LEARNING AND AUGMENTED REALITY BASED USER APPLICATION", filed on Jan. 18, 2020 and in its related U.S. non-provisional patent applications (with all benefit provisional patent applications) are incorporated in its entirety herein with this application.

PREFERRED EMBODIMENTS & SCOPE OF THE INVENTION

As used in the above disclosed specifications, the above disclosed specifications "/" has been used to indicate an "or".

As used in the above disclosed specifications and in the claims, the singular forms "a", "an", and "the" include also the plural forms, unless the context clearly dictates otherwise.

As used in the above disclosed specifications, the term "includes" means "comprises". Also, the term "including" means "comprising".

As used in the above disclosed specifications, the term "couples" or "coupled" does not exclude the presence of an intermediate element(s) between the coupled items.

Any dimension in the above disclosed specifications is by way of an approximation only and not by way of any limitation.

As used in the above disclosed specifications, a hardware module/module is defined as an integration of critical electrical/optical/radio/sensor components and circuits (and algorithms or computer implementable instructions, if needed) to achieve a desired property of a hardware module/module.

As used in the above disclosed specifications, a computational camera sensor is generally equivalent to a Light Detection and Ranging (LiDAR) device in meaning and in practice.

As used in the above disclosed specifications, an algorithm is defined as an organized set of computer implementable instructions to achieve a desired task.

As used in the above disclosed specifications, a software module is defined as a collection of consistent algorithms to achieve a desired task. A software module or an algorithm, as used in the above disclosed specifications can be stored in a cloud server or locally on the device/subsystem.

As used in the above disclosed specifications, real-time means near real-time in practice.

Any example in the above disclosed specifications is by way of an example only and not by way of any limitation. Having described and illustrated the principles of the disclosed technology with reference to the illustrated embodiments, it will be recognized that the illustrated embodiments can be modified in any arrangement and detail without departing from such principles. The technologies from any example can be combined in any arrangement with the technologies described in any one or more of the other examples. Alternatives specifically addressed in this application are merely exemplary and do not constitute all possible examples. Claimed invention is disclosed as one of several possibilities or as useful separately or in various combinations. See Novozymes A/S v. DuPont Nutrition Biosciences APS, 723 F3d 1336, 1347.

The best mode requirement "requires an inventor(s) to disclose the best mode contemplated by him/her, as of the time he/she executes the application, of carrying out the invention." " . . . [T]he existence of a best mode is a purely subjective matter depending upon what the inventor(s) actually believed at the time the application was filed." See Bayer AG v. Schein Pharmaceuticals, Inc. The best mode requirement still exists under the America Invents Act (AIA). At the time of the invention, the inventor(s) described preferred best mode embodiments of the present invention. The sole purpose of the best mode requirement is to restrain the inventor(s) from applying for a patent, while at the same time concealing from the public preferred embodiments of their inventions, which they have in fact conceived. The best mode inquiry focuses on the inventor(s)' state of mind at the time he/she filed the patent application, raising a subjective factual question. The specificity of disclosure required to comply with the best mode requirement must be determined by the knowledge of facts within the possession of the inventor(s) at the time of filing the patent application. See Glaxo, Inc. v. Novopharm Ltd., 52 F.3d 1043, 1050 (Fed. Cir. 1995). The above disclosed specifications are the preferred best mode embodiments of the present invention. However, they are not intended to be limited only to the preferred best mode embodiments of the present invention.

Embodiment by definition is a manner in which an invention can be made or used or practiced or expressed. "A tangible form or representation of the invention" is an embodiment.

Numerous variations and/or modifications are possible within the scope of the present invention. Accordingly, the disclosed preferred best mode embodiments are to be construed as illustrative only. Those who are skilled in the art can make various variations and/or modifications without departing from the scope and spirit of this invention. It should be apparent that features of one embodiment can be combined with one or more features of another embodiment to form a plurality of embodiments. The inventor(s) of the present invention is not required to describe each and every conceivable and possible future embodiment in the preferred best mode embodiments of the present invention within the context of a predictable technological field. See SRI Int'l v. Matsushita Elec. Corp. of America, 775F.2d 1107, 1121, 227 U.S.P.Q. (BNA) 577, 585 (Fed. Cir. 1985) (enbanc).

The scope and spirit of this invention shall be defined by the claims and the equivalents of the claims only. The exclusive use of all variations and/or modifications within the scope of the claims is reserved. The general presumption is that claim terms should be interpreted using their plain and ordinary meaning without improperly importing a limitation from the specification into the claims. See Continental Circuits LLC v. Intel Corp. (Appeal Number 2018-1076, Fed. Cir. Feb. 8, 2019) and Oxford Immunotec Ltd. v. Qiagen, Inc. et al., Action No. 15-cv-13124-NMG. Unless a claim term is specifically defined in the preferred best mode embodiments, then a claim term has an ordinary meaning, as understood by a person with an ordinary skill in the art, at the time of the present invention. Plain claim language will not be narrowed, unless the inventor(s) of the present invention clearly and explicitly disclaims broader claim scope. See Sumitomo Dainippon Pharma Co. v. Emcure Pharm. Ltd., Case Nos. 17-1798; -1799; -1800 (Fed. Cir. Apr. 16, 2018) (Stoll, J). As noted long ago: "Specifications teach. Claims claim". See Rexnord Corp. v. Laitram Corp., 274 F.3d 1336, 1344 (Fed. Cir. 2001). The rights of claims (and rights of the equivalents of the claims) under the Doctrine of Equivalents-meeting the "Triple Identity Test" (a) performing substantially the same function, (b) in substantially the same way and (c) yielding substantially the same result. See Crown Packaging Tech., Inc. v. Rexam Beverage Can Co., 559 F.3d 1308, 1312 (Fed. Cir. 2009)) of the present invention are not narrowed or limited by the selective imports of the specifications (of the preferred embodiments of the present invention) into the claims.

While "absolute precision is unattainable" in patented claims, the definiteness requirement "mandates clarity." See Nautilus, Inc. v. Biosig Instruments, Inc., 527 U.S., 134 S. Ct. 2120, 2129, 110 USPQ2d 1688, 1693 (2014). Definiteness of claim language must be analyzed NOT in a vacuum, but in light of:

(a) The content of the particular application disclosure, (b) The teachings of any prior art and (c) The claim interpretation that would be given by one possessing the ordinary level of skill in the pertinent art at the time the invention was made. (Id.).

See Orthokinetics, Inc. v. Safety Travel Chairs, Inc., 806 F.2d 1565, 1 USPQ2d 1081 (Fed. Cir. 1986).

There are a number of ways the written description requirement is satisfied. Applicant(s) does not need to describe every claim element exactly, because there is no such requirement (MPEP § 2163). Rather to satisfy the written description requirement, all that is required is "reasonable clarity" (MPEP § 2163.02). An adequate description may be made in any way through express, implicit or even inherent disclosures in the application, including word, structures, figures, diagrams and/or equations (MPEP §§ 2163(I), 2163.02). The set of claims in this invention generally covers a set of sufficient number of embodiments to conform to written description and enablement doctrine. See Ariad Pharm., Inc. v. Eli Lilly & Co., 598 F.3d 1336, 1355 (Fed. Cir. 2010), Regents of the University of California v. Eli Lilly & Co., 119 F.3d 1559 (Fed. Cir. 1997) & Amgen Inc. v. Chugai Pharmaceutical Co. 927 F.2d 1200 (Fed. Cir. 1991).

Furthermore, Amgen Inc. v. Chugai Pharmaceutical Co. exemplifies Federal Circuit's strict enablement requirements. Additionally, the set of claims in this invention is intended to inform the scope of this invention with "reasonable certainty". See Interval Licensing, LLC v. AOL Inc. (Fed. Cir. Sep. 10, 2014). A key aspect of the enablement requirement is that it only requires that others will not have to perform "undue experimentation" to reproduce it. Enablement is not precluded by the necessity of some experimentation, "[t]he key word is 'undue', not experimentation." Enablement is generally considered to be an important factor for determining the scope of claim protection allowed. The scope of enablement must be commensurate with the scope of the claims. However, enablement does not require that an inventor disclose every possible embodiment of his invention. The scope of the claims must be less than or equal to the scope of enablement. See Promega v. Life Technologies Fed. Cir., December 2014, Magsil v. Hitachi Global Storage Fed. Cir. August 2012.

The term "means" was not used nor intended nor implied in the disclosed preferred best mode embodiments of the present invention. Thus, the inventor(s) has not limited the scope of the claims as a mean plus function.

An apparatus claim with functional language is not an impermissible "hybrid" claim; instead, it is simply an apparatus claim including functional limitations. Additionally, "apparatus claims are not necessarily indefinite for using functional language . . . [f]unctional language may also be employed to limit the claims without using the means-plus-function format." See National Presto Industries, Inc. v. The West Bend Co., 76 F. 3d 1185 (Fed. Cir. 1996), R.A.C.C. Indus. v. Stun-Tech, Inc., 178 F.3d 1309 (Fed. Cir. 1998) (unpublished), Microprocessor Enhancement Corp. v. Texas Instruments Inc. & Williamson v. Citrix Online, LLC, 792 F.3d 1339 (2015).

In conclusion, it is intended that the scope of the invention is not limited by this detailed specification with preferred embodiments, but rather by claims appended hereto.

I claim:

1. An intelligent subsystem,
wherein the intelligent subsystem is operable with a wireless network or Zigbee,
wherein the intelligent subsystem is sensor-aware and/or context-aware,
wherein the intelligent subsystem comprises:
(a) a first radio transceiver;
wherein the first radio transceiver comprises one or more first electronic components,
(b) a microphone;
(c) a voice processing module to process an audio signal; and
wherein the voice processing module comprises one or more second electronic components,
wherein the audio signal is a voice command,
(d) a System-on-a-Chip (SoC),
wherein the System-on-a-Chip (SoC) comprises:
one or more (i) processor-specific electronic integrated circuits (EICs) and (ii) first sets of computer implementable instructions,
wherein at least one of the one or more processor-specific electronic integrated circuits (EICs) comprises one or more central processors,
wherein the System-on-a-Chip (SoC) has one or more multipliers of matrices,
wherein at least one of the one or more first sets of computer implementable instructions is (i) embedded computer implementable instructions and (ii) processed on the System-on-a-Chip (SoC),
wherein the System-on-a-Chip (SoC) is coupled with the voice processing module,
wherein the intelligent subsystem is communicatively interfaced with:
(i) a second set of computer implementable instructions to process the audio signal,
(ii) a third set of computer implementable instructions to provide a recommendation inferred from an interest or a preference, that was received at the intelligent subsystem, wherein the third set of computer implementable instructions comprises natural language processing (NLP),
(iii) a fourth set of computer implementable instructions in artificial neural networks (ANN),
wherein the artificial neural networks (ANN) include a transformer model based computer implementable instructions or a diffusion model based computer implementable instructions and
(iv) a fifth set of computer implementable instructions to analyze and interpret contextual data,
wherein the second set of computer implementable instructions, the third set of computer implementable instructions, the fourth set of computer implementable instructions and the fifth set of computer implementable instructions are stored in one or more non-transitory storage media, located either locally on the intelligent subsystem or in a cloud server.

2. The intelligent subsystem according to claim 1, is a user cloud based subsystem or a cloud based subsystem.

3. The intelligent subsystem according to claim 1, wherein the System-on-a-Chip (SoC) further comprises one or more on-sensor processing circuits, wherein at least one of the one or more on-sensor processing circuits includes one or more digital signal processors (DSPs).

4. The intelligent subsystem according to claim 1, wherein the System-on-a-Chip (SoC) is further thermally coupled with an active cooler or a passive cooler.

5. The intelligent subsystem according to claim 1, further comprises (i) a touch sensor and a display and/or (ii) a computational camera or a metasurface lens, wherein the computational camera comprises a laser and a photodiode, wherein the metasurface lens comprises one or more patterned structures of a material, wherein at least one of the one or more patterned structures of the material has a dimension less than 20,000 nm.

6. The intelligent subsystem according to claim 5, wherein the touch sensor includes one or more microfluidic channels.

7. The intelligent subsystem according to claim 5, wherein the display is selected from the group consisting of a photonic crystal display, an array of microLEDs based display, a metasurface based display and a holographic display, wherein the photonic crystal display includes one or more first nanoscaled structures, wherein the holographic display comprises a spatial light modulator (SLM) or a diffractive optical element (DOE), wherein the metasurface based display comprises one or more second nanoscaled structures.

8. The intelligent subsystem according to claim 5, wherein the display is a foldable display or a rollable display.

9. The intelligent subsystem according to claim 5, wherein the display comprises one or more pixels, wherein at least one of the one or more pixels includes a camera sensor.

10. The intelligent subsystem according to claim 5, wherein the display comprises one or more piezoelectric transducer based speakers.

11. The intelligent subsystem according to claim 1, further comprises (i) an intelligent camera or (ii) a neuromorphic event camera or (iii) a hyperspectral camera, wherein the intelligent camera includes one or more digital signal processors (DSPs), wherein the neuromorphic event camera comprises one or more optoelectronic synapse based light sensors, wherein an output of at least one of the one or more optoelectronic synapse based light sensors is a stream of events, wherein the output of at least one of the one or more optoelectronic synapse based light sensors is encoded in a change of brightness, wherein the hyperspectral camera comprises an array of photodiodes.

12. The intelligent subsystem according to claim 11, wherein the intelligent camera is further communicatively interfaced with a sixth set of computer implementable instructions to classify an image, wherein the sixth set of computer implementable instructions includes (i) machine learning or (ii) the artificial neural networks (ANN), wherein the sixth set of computer implementable instructions is stored in the one or more non-transitory storage media, located either locally on the intelligent subsystem or in the cloud server.

13. The intelligent subsystem according to claim 1, is further coupled with a virtual reality (VR) application (app) or an augmented reality (AR) application (app) or a mixed reality (MR) application (app).

14. The intelligent subsystem according to claim 1, is further coupled with a telemedicine application (app) or a peer-to-peer transaction application (app).

15. The intelligent subsystem according to claim 1, is further coupled with (i) a biological lab-on-a-chip (LOC) or (ii) a biomodule or (iii) a bioobject,
wherein the biological lab-on-a-chip (LOC) comprises a photodetector or a light sensor, wherein the biomodule comprises a nanoscaled hole on a substrate and an electronic circuit, wherein the nanoscaled hole on the substrate is less than 10 nanometers in diameter,
wherein the electronic circuit is electrically coupled with the nanoscaled hole on the substrate to measure an electrical signal related to movement of nucleotides or amino acids,
wherein the bioobject comprises a microcontroller and a second radio transceiver, wherein the second radio transceiver comprises one or more third electronic components, wherein the bioobject is implanted within a human body or transiting through the human body.

16. The intelligent subsystem according to claim 1, wherein the fourth set of computer implementable instructions further comprises an evolutionary algorithm based computer implementable instructions or a game theory algorithm based computer implementable instructions.

17. The intelligent subsystem according to claim 1, wherein the fourth set of computer implementable instructions further comprises Kolmogorov-Arnold based neural network architecture (KANN) or Poisson flow generative model++ (PFGM++).

18. The intelligent subsystem according to claim 1, wherein the intelligent subsystem is further communicatively interfaced with a seventh set of computer implementable instructions to convert (i) an image to the audio signal or (ii) a text to a video, wherein the seventh set of computer implementable instructions is stored in the one or more non-transitory storage media, located either locally on the intelligent subsystem or in the cloud server.

19. The intelligent subsystem according to claim 1, is further communicatively interfaced with an eighth set of computer implementable instructions in self-learning at least based on a text, an image, a video and an experience, wherein the eighth set of computer implementable instructions is stored in the one or more non-transitory storage media, located either locally on the intelligent subsystem or in the cloud server.

20. The intelligent subsystem according to claim 1, is further communicatively interfaced with a self-learning chatbot, wherein the self-learning chatbot includes a ninth set of computer implementable instructions in natural language processing (NLP), wherein the ninth set of computer implementable instructions is stored in the one or more non-transitory storage media, located either locally on the intelligent subsystem or in the cloud server.

21. The intelligent subsystem according to claim 1, is further communicatively interfaced with an autonomous artificial intelligence (AI) agent, wherein the autonomous artificial intelligence (AI) agent is a tenth set of computer implementable instructions, wherein the tenth set of computer implementable instructions includes natural language processing (NLP), wherein the tenth set of computer implementable instructions is stored in the one or more non-transitory storage media, located either locally on the intelligent subsystem or in the cloud server.

22. An intelligent subsystem,
wherein the intelligent subsystem is operable with a wireless network or Zigbee,
wherein the intelligent subsystem is sensor-aware and/or context-aware,
wherein the intelligent subsystem comprises:
(a) a first radio transceiver;
wherein the first radio transceiver comprises one or more first electronic components,
(b) a microphone;
(c) a voice processing module to process an audio signal; and
wherein the voice processing module comprises one or more second electronic components,
wherein the audio signal is a voice command,
(d) a System-on-a-Chip (SoC),
wherein the System-on-a-Chip (SoC) comprises:
one or more (i) processor-specific electronic integrated circuits (EICs), (ii) on-sensor processing circuits and (iii) first sets of computer implementable instructions,
wherein at least one of the one or more processor-specific electronic integrated circuits (EICs) comprises one or more graphic processors,
wherein at least one of the one or more on-sensor processing circuits includes one or more first digital signal processors (DSPs),
wherein the System-on-a-Chip (SoC) has one or more multipliers of matrices,
wherein at least one of the one or more first sets of computer implementable instructions is (i) embedded computer implementable instructions and (ii) processed on the System-on-a-Chip (SoC),
wherein the System-on-a-Chip (SoC) is coupled with the voice processing module,
wherein the intelligent subsystem is communicatively interfaced with:
(i) a second set of computer implementable instructions to process the audio signal,
(ii) a third set of computer implementable instructions to provide a recommendation inferred, from an interest or a preference, that was received at the intelligent subsystem, wherein the third set of computer implementable instructions comprises natural language processing (NLP),
(iii) a fourth set of computer implementable instructions in artificial neural networks (ANN),
wherein the artificial neural networks (ANN) include a transformer model based computer implementable instructions or a diffusion model based computer implementable instructions and
(iv) a fifth set of computer implementable instructions to analyze and interpret contextual data,
wherein the second set of computer implementable instructions, the third set of computer implementable instructions, the fourth set of computer implementable instructions and the fifth set of computer implementable instructions are stored in one or more non-transitory storage media, located either locally on the intelligent subsystem or in a cloud server.

23. The intelligent subsystem according to claim 22, is a user cloud based subsystem or a cloud based subsystem.

24. The intelligent subsystem according to claim 22, wherein the System-on-a-Chip (SoC) is further thermally coupled with an active cooler or a passive cooler.

25. The intelligent subsystem according to claim 22, further comprises (i) a touch sensor and a display and/or (ii) a computational camera or a metasurface lens, wherein the computational camera comprises a laser and a photodiode, wherein the metasurface lens comprises one or more patterned structures of a material, wherein at least one of the one or more patterned structures of the material has a dimension less than 20,000 nm.

26. The intelligent subsystem according to claim 25, wherein the touch sensor includes one or more microfluidic channels.

27. The intelligent subsystem according to claim 25, wherein the display is selected from the group consisting of a photonic crystal display, an array of microLEDs based display, a metasurface based display and a holographic display, wherein the photonic crystal display includes one or more first nanoscaled structures, wherein the metasurface based display comprises one or more second nanoscaled structures.

28. The intelligent subsystem according to claim 25, wherein the display is a foldable display or a rollable display.

29. The intelligent subsystem according to claim 25, wherein the display comprises one or more pixels, wherein at least one of the one or more pixels includes a camera sensor.

30. The intelligent subsystem according to claim 25, wherein the display comprises one or more piezoelectric transducer based speakers.

31. The intelligent subsystem according to claim 22, further comprises (i) an intelligent camera or (ii) a neuromorphic event camera or (iii) a hyperspectral camera, wherein the intelligent camera includes one or more second digital signal processors (DSPs), wherein the neuromorphic event camera comprises one or more optoelectronic synapse based light sensors, wherein an output of at least one of the one or more optoelectronic synapse based light sensors is a stream of events, wherein the output of at least one of the one or more optoelectronic synapse based light sensors is encoded in a change of brightness, wherein the hyperspectral camera comprises an array of photodiodes.

32. The intelligent subsystem according to claim 31, wherein the intelligent camera is further communicatively interfaced with a sixth set of computer implementable instructions to classify an image, wherein the sixth set of computer implementable instructions includes (i) machine learning or (ii) the artificial neural networks (ANN), wherein the sixth set of computer implementable instructions is stored in the one or more non-transitory storage media, located either locally on the intelligent subsystem or in the cloud server.

33. The intelligent subsystem according to claim 22, is further coupled with a virtual reality (VR) application (app) or an augmented reality (AR) application (app) or a mixed reality (MR) application (app).

34. The intelligent subsystem according to claim 22, is further coupled with a telemedicine application (app) or a peer-to-peer transaction application (app).

35. The intelligent subsystem according to claim 22, is further coupled with (i) a biological lab-on-a-chip (LOC) or (ii) a biomodule or (iii) a bioobject,
wherein the biological lab-on-a-chip (LOC) comprises a photodetector or a light sensor,
wherein the biomodule comprises a nanoscaled hole on a substrate and an electronic circuit, wherein the nanoscaled hole on the substrate is less than 10 nanometers in diameter, wherein the electronic circuit is electrically coupled with the nanoscaled hole on the substrate to measure an electrical signal related to movement of nucleotides or amino acids,
wherein the bioobject comprises a microcontroller and a second radio transceiver, wherein the second radio transceiver comprises one or more third electronic components, wherein the bioobject is implanted within a human body or transiting through the human body.

36. The intelligent subsystem according to claim 22, wherein the fourth set of computer implementable instructions further comprises an evolutionary algorithm based computer implementable instructions or a game theory algorithm based computer implementable instructions.

37. The intelligent subsystem according to claim 22, wherein the fourth set of computer implementable instructions further comprises Kolmogorov-Arnold based neural network architecture (KANN) or Poisson flow generative model++ (PFGM++).

38. The intelligent subsystem according to claim 22, wherein the intelligent subsystem is further communicatively interfaced with a seventh set of computer implementable instructions to convert (i) an image to the audio signal or (ii) a text to a video, wherein the seventh set of computer implementable instructions is stored in the one or more non-transitory storage media, located either locally on the intelligent subsystem or in the cloud server.

39. The intelligent subsystem according to claim 22, is further communicatively interfaced with an eighth set of computer implementable instructions in self-learning at least based on a text, an image, a video and an experience, wherein the eighth set of computer implementable instructions is stored in the one or more non-transitory storage media, located either locally on the intelligent subsystem or in the cloud server.

40. The intelligent subsystem according to claim 22, is further communicatively interfaced with a self-learning chatbot, wherein the self-learning chatbot includes a ninth set of computer implementable instructions in natural language processing (NLP), wherein the ninth set of computer implementable instructions is stored in the one or more non-transitory storage media, located either locally on the intelligent subsystem or in the cloud server.

41. The intelligent subsystem according to claim 22, is further communicatively interfaced with an autonomous artificial intelligence (AI) agent, wherein the autonomous artificial intelligence (AI) agent is a tenth set of computer implementable instructions, wherein the tenth set of computer implementable instructions includes natural language processing (NLP), wherein the tenth set of computer implementable instructions is stored in the one or more non-transitory storage media, located either locally on the intelligent subsystem or in the cloud server.

42. An intelligent subsystem,
wherein the intelligent subsystem is operable with a wireless network or Zigbee,
wherein the intelligent subsystem is sensor-aware and/or context-aware,
wherein the intelligent subsystem comprises:
(a) a first radio transceiver;
wherein the first radio transceiver comprises one or more first electronic components,
(b) a microphone;
(c) a voice processing module to process an audio signal; and
wherein the voice processing module comprises one or more second electronic components,
wherein the audio signal is a voice command,
(d) a System-on-a-Chip (SoC),
wherein the System-on-a-Chip (SoC) comprises:
one or more (i) processor-specific electronic integrated circuits (EICs), (ii) on-sensor processing circuits and (iii) first sets of computer implementable instructions,
wherein at least one of the one or more processor-specific electronic integrated circuits (EICs) comprises (i) one or more central processors and (ii) one or more graphic processors,
wherein at least one of the one or more on-sensor processing circuits includes one or more first digital signal processors (DSPs), wherein the System-on-a-Chip (SoC) has one or more multipliers of matrices, wherein at least one of the one or more first sets of computer implementable instructions is (i) embedded computer implementable instructions and (ii) processed on the System-on-a-Chip (SoC), wherein the System-on-a-Chip (SoC) is coupled with the voice processing module, wherein the intelligent subsystem is communicatively interfaced with:

(i) a second set of computer implementable instructions to process the audio signal, (ii) a third set of computer implementable instructions to provide a recommendation inferred from an interest or a preference, that was received at the intelligent subsystem, wherein the third set of computer implementable instructions comprises natural language processing (NLP), (iii) a fourth set of computer implementable instructions in artificial neural networks (ANN), wherein the artificial neural networks (ANN) include a transformer model based computer implementable instructions or a diffusion model based computer implementable instructions and (iv) a fifth set of computer implementable instructions to analyze and interpret contextual data, wherein the second set of computer implementable instructions, the third set of computer implementable instructions, the fourth set of computer implementable instructions and the fifth set of computer implementable instructions are stored in one or more non-transitory storage media, located either locally on the intelligent subsystem or in a cloud server.

43. The intelligent subsystem according to claim 42, is a user cloud based subsystem or a cloud based subsystem.

44. The intelligent subsystem according to claim 42, wherein the System-on-a-Chip (SoC) is further thermally coupled with an active cooler or a passive cooler.

45. The intelligent subsystem according to claim 42, further comprises (i) a touch sensor and a display and/or (ii) a computational camera or a metasurface lens, wherein the computational camera comprises a laser and a photodiode, wherein the metasurface lens comprises one or more patterned structures of a material, wherein at least one of the one or more patterned structures of the material has a dimension less than 20,000 nm.

46. The intelligent subsystem according to claim 45, wherein the touch sensor includes one or more microfluidic channels.

47. The intelligent subsystem according to claim 45, wherein the display is selected from the group consisting of a photonic crystal display, an array of microLEDs based display, a metasurface based display and a holographic display, wherein the photonic crystal display includes one or more first nanoscaled structures, wherein the metasurface based display comprises one or more second nanoscaled structures.

48. The intelligent subsystem according to claim 45, wherein the display is a foldable display or a rollable display.

49. The intelligent subsystem according to claim 45, wherein the display comprises one or more pixels, wherein at least one of the one or more pixels includes a camera sensor.

50. The intelligent subsystem according to claim 45, wherein the display comprises one or more piezoelectric transducer based speakers.

51. The intelligent subsystem according to claim 42, further comprises (i) an intelligent camera or (ii) a neuromorphic event camera or (iii) a hyperspectral camera, wherein the intelligent camera includes one or more second digital signal processors (DSPs), wherein the neuromorphic event camera comprises one or more optoelectronic synapse based light sensors, wherein an output of at least one of the one or more optoelectronic synapse based light sensors is a stream of events, wherein the output of at least one of the one or more optoelectronic synapse based light sensors is encoded in a change of brightness, wherein the hyperspectral camera comprises an array of photodiodes.

52. The intelligent subsystem according to claim 51, wherein the intelligent camera is further communicatively interfaced with a sixth set of computer implementable instructions to classify an image, wherein the sixth set of computer implementable instructions includes (i) machine learning or (ii) the artificial neural networks (ANN), wherein the sixth set of computer implementable instructions is stored in the one or more non-transitory storage media, located either locally on the intelligent subsystem or in the cloud server.

53. The intelligent subsystem according to claim 42, is further coupled with a virtual reality (VR) application (app) or an augmented reality (AR) application (app) or a mixed reality (MR) application (app).

54. The intelligent subsystem according to claim 42, is further coupled with a telemedicine application (app) or a peer-to-peer transaction application (app).

55. The intelligent subsystem according to claim 42, is further coupled with (i) a biological lab-on-a-chip (LOC) or (ii) a biomodule or (iii) a bioobject, wherein the biological lab-on-a-chip (LOC) comprises a photodetector or a light sensor, wherein the biomodule comprises a nanoscaled hole on a substrate and an electronic circuit, wherein the nanoscaled hole on the substrate is less than 10 nanometers in diameter, wherein the electronic circuit is electrically coupled with the nanoscaled hole on the substrate to measure an electrical signal related to movement of nucleotides or amino acids, wherein the bioobject comprises a microcontroller and a second radio transceiver, wherein the second radio transceiver comprises one or more third electronic components, wherein the bioobject is implanted within a human body or transiting through the human body.

56. The intelligent subsystem according to claim 42, wherein the fourth set of computer implementable instructions further comprises an evolutionary algorithm based computer implementable instructions or a game theory algorithm based computer implementable instructions.

57. The intelligent subsystem according to claim 42, wherein the fourth set of computer implementable instructions further comprises Kolmogorov-Arnold based neural network architecture (KANN) or Poisson flow generative model++ (PFGM++).

58. The intelligent subsystem according to claim 42, wherein the intelligent subsystem is further communicatively interfaced with a seventh set of computer implementable instructions to convert (i) an image to the audio signal or (ii) a text to a video, wherein the seventh set of computer implementable instructions is stored in the one or more non-transitory storage media, located either locally on the intelligent subsystem or in the cloud server.

59. The intelligent subsystem according to claim 42, is further communicatively interfaced with an eighth set of computer implementable instructions in self-learning at least based on a text, an image, a video and an experience, wherein the eighth set of computer implementable instructions is stored in the one or more non-transitory storage media, located either locally on the intelligent subsystem or in the cloud server.

60. The intelligent subsystem according to claim 42, is further communicatively interfaced with a self-learning chatbot, wherein the self-learning chatbot includes a ninth set of computer implementable instructions in natural language processing (NLP), wherein the ninth set of computer implementable instructions is stored in the one or more non-transitory storage media, located either locally on the intelligent subsystem or in the cloud server.

61. The intelligent subsystem according to claim 42, is further communicatively interfaced with an autonomous artificial intelligence (AI) agent, wherein the autonomous artificial intelligence (AI) agent is a tenth set of computer implementable instructions, wherein the tenth set of computer implementable instructions includes natural language processing (NLP), wherein the tenth set of computer implementable instructions is stored in the one or more non-transitory storage media, located either locally on the intelligent subsystem or in the cloud server.

62. The intelligent subsystem according to claim 42, is further coupled with an optical access network.

* * * * *